United States Patent
Morita

(10) Patent No.: US 10,712,411 B2
(45) Date of Patent: Jul. 14, 2020

(54) BULK MAGNET STRUCTURE AND BULK MAGNET SYSTEM FOR NMR

(71) Applicant: NIPPON STEEL & SUMITOMO METAL CORPORATION, Tokyo (JP)

(72) Inventor: Mitsuru Morita, Tokyo (JP)

(73) Assignee: NIPPON STEEL CORPORATION, Tokyo (JP)

( * ) Notice: Subject to any disclaimer, the term of this patent is extended or adjusted under 35 U.S.C. 154(b) by 0 days.

(21) Appl. No.: 16/320,703

(22) PCT Filed: Jul. 27, 2017

(86) PCT No.: PCT/JP2017/027347
§ 371 (c)(1),
(2) Date: Jan. 25, 2019

(87) PCT Pub. No.: WO2018/021506
PCT Pub. Date: Feb. 1, 2018

(65) Prior Publication Data
US 2019/0162802 A1    May 30, 2019

(30) Foreign Application Priority Data
Jul. 27, 2016   (JP) ................................. 2016-147152

(51) Int. Cl.
*G01V 3/00*        (2006.01)
*G01R 33/385*      (2006.01)
(Continued)

(52) U.S. Cl.
CPC .......... *G01R 33/3856* (2013.01); *A61B 5/055* (2013.01); *G01R 33/38* (2013.01);
(Continued)

(58) Field of Classification Search
CPC .............. G01R 33/543; G01R 33/5659; G01R 33/3415; G01R 33/36; A61B 5/055
(Continued)

(56) References Cited

U.S. PATENT DOCUMENTS

| | | | |
|---|---|---|---|
| 5,496,798 A | * | 3/1996 | Sakai .................. H05K 9/0077 335/214 |
| 5,795,849 A | | 8/1998 | Hickman |

(Continued)

FOREIGN PATENT DOCUMENTS

| | | |
|---|---|---|
| CN | 101577165 A | 11/2009 |
| CN | 101593597 A | 12/2009 |

(Continued)

OTHER PUBLICATIONS

Fujishiro et al., "Drastic Improvement of the trapped field homogeneity in a superconducting hollow bulk by the insertion of a high-Jc superconducting cylinder for NMR bulk magnets", Supercond. Sci. Technol., vol. 28, 2015 (published online Aug. 18, 2015), pp. 1-8 (8 pages).

(Continued)

*Primary Examiner* — Walter L Lindsay, Jr.
*Assistant Examiner* — Frederick Wenderoth
(74) *Attorney, Agent, or Firm* — Birch, Stewart, Kolasch & Birch, LLP

(57) ABSTRACT

The purpose of the present invention is to make it possible to use a wider uniform magnetic field space and to achieve an additional use mode for a bulk magnet structure. A bulk magnet structure according to the present invention is provided with a plurality of oxide superconducting bulk bodies arranged so that the central axes thereof are on the same line and at least one outer circumferential reinforcing ring fitted to the bulk magnet structure so as to cover the outer circumferential surfaces of the plurality of oxide supercon- (Continued)

ducting bulk bodies. The plurality of oxide superconducting bulk bodies includes a columnar oxide superconducting bulk body and/or a ring-shaped oxide superconducting bulk body. At least one set of adjacent oxide superconducting bulk bodies are spaced apart from each other in the direction of the central axes thereof. The interior of the bulk magnet structure includes a space through which the central axes pass.

20 Claims, 40 Drawing Sheets

(51) Int. Cl.
 *A61B 5/055* (2006.01)
 *H01F 7/20* (2006.01)
 *G01R 33/38* (2006.01)
 *H01F 6/00* (2006.01)
 *H01F 6/04* (2006.01)
 *H01F 6/06* (2006.01)
(52) U.S. Cl.
 CPC ............... *H01F 6/00* (2013.01); *H01F 6/04* (2013.01); *H01F 6/06* (2013.01); *H01F 7/20* (2013.01); *H01F 7/202* (2013.01); *G06T 2207/10088* (2013.01)
(58) Field of Classification Search
 USPC ........................................................ 324/309
 See application file for complete search history.

(56) References Cited

U.S. PATENT DOCUMENTS

| | | | |
|---|---|---|---|
| 7,764,153 | B2 | 7/2010 | Isogami et al. |
| 2002/0000806 | A1* | 1/2002 | Nakamura ......... G01R 33/3815 324/315 |
| 2005/0134414 | A1 | 6/2005 | Wakuda et al. |
| 2007/0052421 | A1 | 3/2007 | Wakuda et al. |
| 2007/0215166 | A1* | 9/2007 | Branton ................. A24B 15/42 15/42 |
| 2011/0309527 | A1* | 12/2011 | Okamoto ............. H01L 21/565 257/782 |
| 2012/0227418 | A1* | 9/2012 | Decker .................. F25B 9/002 62/62 |
| 2012/0231958 | A1 | 9/2012 | Morita et al. |
| 2015/0369885 | A1* | 12/2015 | Ito ...................... G01R 33/3815 505/162 |

FOREIGN PATENT DOCUMENTS

| | | | |
|---|---|---|---|
| EP | 3001432 | A1 | 3/2016 |
| JP | 60-101707 | U | 7/1985 |
| JP | 8-236983 | A | 9/1996 |
| JP | 10-310497 | A | 11/1998 |
| JP | 11-284238 | A | 10/1999 |
| JP | 11-335120 | A | 12/1999 |
| JP | 2002-6021 | A | 1/2002 |
| JP | 2002-221560 | A | 8/2002 |
| JP | 2004-309208 | A | 11/2004 |
| JP | 2007-129158 | A | 5/2007 |
| JP | 2008-034692 | A | 2/2008 |
| JP | 2009-156719 | A | 7/2009 |
| JP | 2013-183090 | A | 9/2013 |
| JP | 2014-53479 | A | 3/2014 |
| JP | 2014-75522 | A | 4/2014 |
| JP | 2014-146760 | A | 8/2014 |
| JP | 2015-167576 | A | 9/2015 |
| JP | 2016-6825 | A | 1/2016 |
| WO | WO 2011/071071 | A1 | 6/2011 |
| WO | WO 2015/015892 | A1 | 2/2015 |

OTHER PUBLICATIONS

International Preliminary Report on Patentability and Written Opinion of the International Searching Authority(Forms PCT/IB/326, PCT/IB/373 and PCT/ISA/237), dated Feb. 7, 2019, for International Application No. PCT/JP2017/027347, with an English Translation of the Written Opinion.
International Search Report, dated Oct. 24, 2017, for International Application No. PCT/JP2017/027347, with an English translation.
Nakamura et al., "Application of a Compact Cryogen-free Superconducting Bulk Magnet to NMR—Evaluation of a Superconducting Bulk Magnet using NMR Signal—", Teion Kogaku (J. Cryo. Soc. Jpn.), vol. 46, No. 3, 2011, pp. 139-148 (10 pages) with English abstract.
Extended European Search Report for corresponding European Application No. 17834508.8, dated Dec. 19, 2019.

* cited by examiner

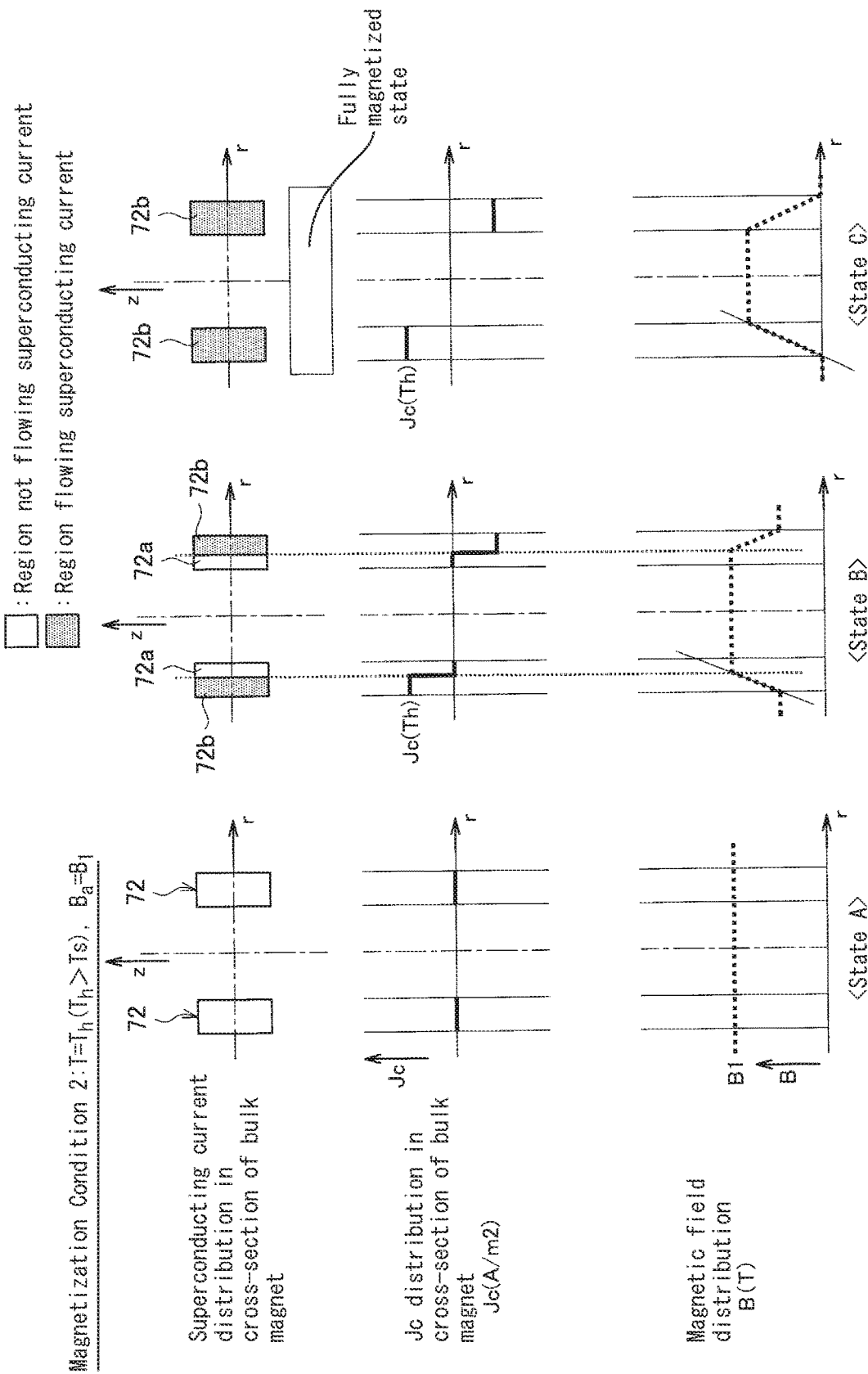

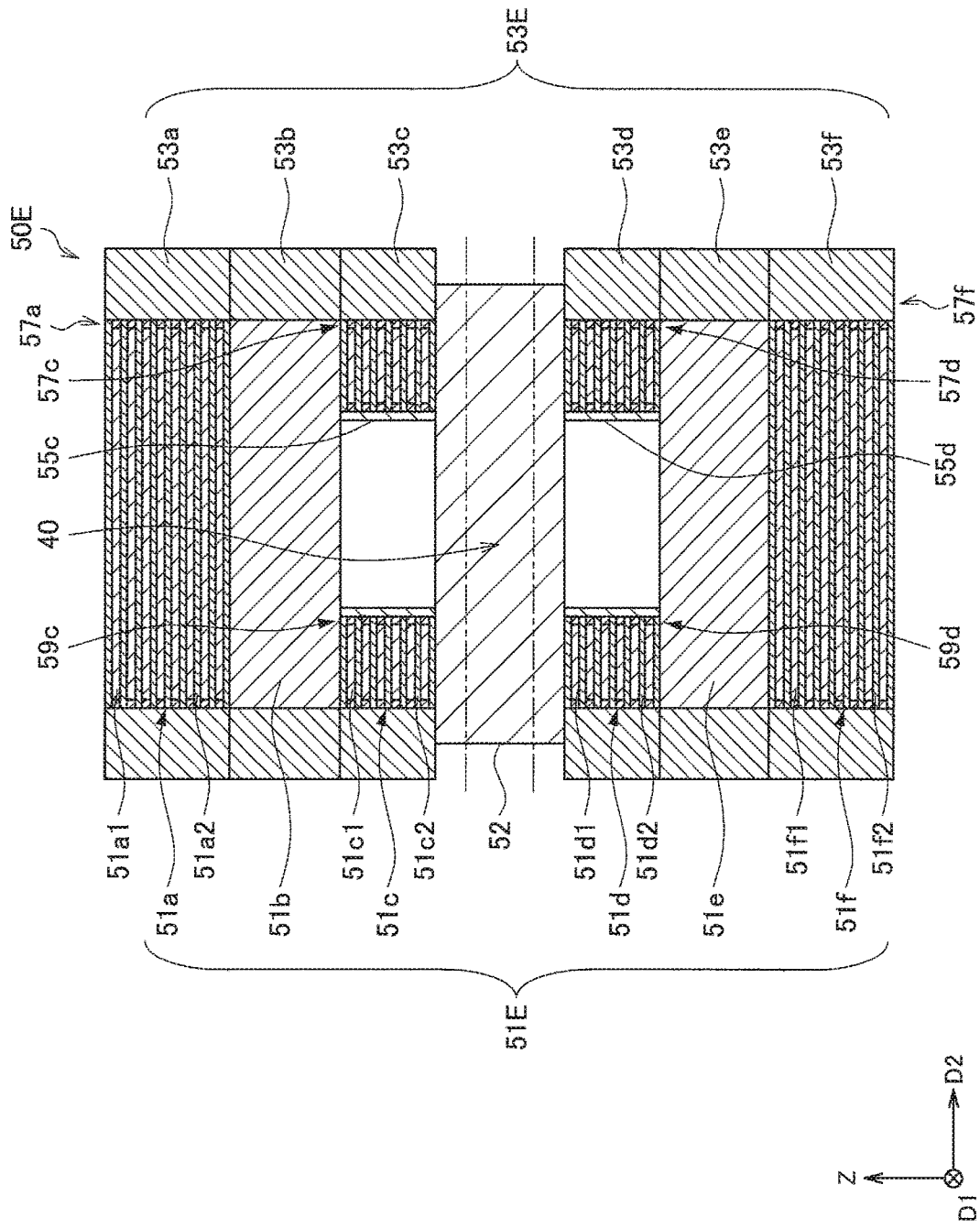

(a)

(b)

BULK MAGNET STRUCTURE AND BULK MAGNET SYSTEM FOR NMR

FIELD

The present invention relates to a bulk magnet structure and a bulk magnet system for NMR.

BACKGROUND

An oxide superconducting bulk body (so-called QMG (registered trademark) bulk body) in which $RE_2BaCuO_5$ phase is dispersed in a monocrystalline $REBa_2Cu_3O_{7-x}$ (RE is a rare earth element) phase has a high critical current density (hereinafter also referred to as "Jc"). Therefore, it can be used as a superconducting bulk magnet excited by cooling in a magnetic field or pulse magnetization and capable of generating a strong magnetic field.

Examples of application fields requiring a strong magnetic field include NMR (Nuclear Magnetic Resonance) and MRI (Magnetic Resonance Imaging). A superconducting bulk magnet to be used for both application fields is required to have a strong magnetic field of several T and high uniformity on the order of ppm.

With respect to NMR application using an oxide superconducting bulk body, there are applications to small (for example, desktop) NMR described in, for example, Patent Documents 1 to 6 and Non-Patent Documents 1 and 2. The fundamental technical ideas of these small NMR applications are as follows. Conventional superconducting magnets for NMR used as magnetizing magnets use superconducting wires, are relatively large, have high uniformity on the order of ppm, and can generate high strength magnetic fields. Inside the room temperature bore of the conventional superconducting magnet for NMR, a bulk magnet structure formed by layering a plurality of ring-shaped oxide superconducting bulk bodies is disposed. By cooling this bulk magnet structure to a superconducting state in a highly uniform magnetic field and then removing the applied magnetic field, the uniform magnetic field generated by the conventional superconducting magnet for NMR is copied to the bulk magnet structure.

In application to such a small NMR, a superconducting magnet for NMR of a wide bore (room temperature bore diameter of 89 mm) is usually used as a magnet for magnetization. Accordingly, in combination with it, a ring-shaped oxide superconducting bulk body having an outer diameter of about 60 mm and an inner diameter of about 30 mm is used. In this case, the magnetization temperature is considerably low, on the order of 40 K, and magnetization is performed under conditions that sufficiently high critical current density (Jc) can be obtained. Specifically, the superconducting current in the cross section of the ring-shaped oxide superconducting bulk body is not in the state of flowing through the entire cross-section (fully magnetized state) but in a state where the superconducting current flows only partially (non-fully magnetized state). By doing so, it is possible to copy a strong magnetic field in the NMR superconducting magnet with a margin. Furthermore, after magnetization, in order to ensure the temporal stability of the magnetic field copied into the ring-shaped oxide superconducting bulk body, the magnet is further cooled from the magnetization temperature to obtain a magnet for small NMR.

Focusing attention on the magnetization methods of Patent Documents 1 to 6 and Non-Patent Documents 1 and 2, for example, Patent Document 1 discloses a method for pulse magnetization and static magnetic field magnetization in an NMR system having a bulk magnet in which ring-shaped oxide superconducting bulk bodies are layered. Patent Document 2 discloses a magnetization method using an NMR system having a bulk magnet in which ring-shaped oxide superconducting bulk bodies are layered such that the magnetic field strength distribution in the central portion has a magnetic field distribution peak at the center of the magnetic field.

Further, Patent Document 3 and Non-Patent Document 1 describe a magnetization method by applying a uniform static magnetic field. In such a magnetization method, a superconducting magnetic field generator having a tubular superconducting body formed by coaxially arranging tubular superconducting bulks having a small magnetic susceptibility on both end faces of a tubular superconducting bulk having a high magnetic susceptibility is used. For example, according to the superconducting magnetic field generator disclosed in Patent Document 3, by designing the magnetic susceptibility and shape of the superconducting bulk so as to satisfy certain conditions, a captured magnetic field having a uniform magnetic field strength in the axial direction of the superconducting body can be formed in the bore of the superconducting body.

Patent Document 4 discloses a superconducting magnetic field generator having a correction coil disposed around a superconducting body made of a tubular superconducting bulk. According to such a superconducting magnetic field generator, when applying a magnetic field to the superconducting body to magnetize it, the applied magnetic field is corrected by the correction coil, whereby a captured magnetic field having a uniform magnetic field strength in the axial direction of the superconducting body can be formed in the bore of the superconducting body.

Patent Document 5 discloses a superconducting magnetic field generator having a superconducting body formed in a tubular shape such that the inner diameter of the center portion in the axial direction is larger than the inner diameter of the end portion. According to such a superconducting magnetic field generator, by setting the inner diameter of the center portion in the axial direction of the tubular superconducting body to be larger than the inner diameter of the end portion, the magnetic field that cancels out the nonuniform magnetic field generated by the magnetization of the superconducting body is formed in the bore of the superconducting body. In Patent Document 5, it is considered that a captured magnetic field having a uniform magnetic field strength in the axial direction of the superconducting body can be formed in the bore of the superconducting body by removing the nonuniform magnetic field in this way.

In Patent Document 6 and Non-Patent Document 2, a magnetization method for obtaining a uniform magnetic field by inserting a tube in which a tape wire material having a high critical current density Jc is spirally wound into a bulk magnet in which ring-shaped oxide superconducting bulk bodies are layered, thereby cancelling the magnetic field component perpendicular to the axial direction.

On the other hand, in application to a small NMR, very strong magnetic field is confined in the compact space of the bulk magnet structure. For this reason, a large electromagnetic stress acts inside the superconducting bulk body. This electromagnetic stress is also called "a hoop stress" because it acts to spread the confined magnetic field. In the case of a strong magnetic field of 5 to 10 T class, the electromagnetic stress may exceed the material mechanical strength of the superconducting bulk body itself. As a result, the superconducting bulk body may break. If the superconducting bulk body breaks, the superconducting bulk body cannot generate a strong magnetic field.

In order to prevent breakage of the superconducting bulk body due to such electromagnetic force, for example, Patent Document 7 discloses that a superconducting bulk magnet is constituted by a columnar superconducting bulk body and a metal ring surrounding the superconducting bulk body. By adopting such a configuration, compressive stress by the metal ring is applied to the superconducting bulk body at the time of cooling, and the compressive stress has an effect of reducing the electromagnetic stress. Therefore, cracking of the superconducting bulk body can be suppressed. Thus, Patent Document 7 shows that breakage of the columnar superconducting bulk body can be prevented.

As another configuration example of the superconducting bulk body for preventing the breakage of the superconducting bulk body, for example, Patent Document 8 discloses a superconducting magnetic field generator in which seven hexagonal superconducting bulk bodies are combined, a reinforcing member made of a fiber reinforced resin or the like is disposed around them, and a support member made of a metal such as stainless steel or aluminum is disposed on the outer circumference of the reinforcing member. Patent Document 9 discloses an oxide superconducting bulk magnet in which ring-shaped bulk superconducting bodies having a thickness in the c-axis direction of the crystal axis of 0.3 to 15 mm are layered. Patent Document 10 discloses a superconducting bulk magnet in which a plurality of ring-shaped superconducting bodies having reinforced outer and inner circumferences are layered. Patent Document 11 discloses a superconducting bulk magnet in which superconducting bodies having a multiple ring structure in the radial direction are layered. Patent Document 12 discloses a bulk magnet in which the outer circumference and the upper and lower surfaces of one bulk body are reinforced.

In addition, as a configuration example of an NMR analysis device magnet with which it is easy to exchange a sample, for example, Patent Document 13 discloses that, in an NMR analysis device magnet in which a magnetic field space is formed by a wound conductor, two similar wound coils having a common center axis are formed with a certain gap therebetween, and access to the magnetic field space is possible from the gap.

PRIOR ART DOCUMENT

Patent Document

[Patent Document 1] Japanese Unexamined Patent Publication (Kokai) No. 2002-006021
[Patent Document 2] Japanese Unexamined Patent Publication (Kokai) No. 2007-129158
[Patent Document 3] Japanese Unexamined Patent Publication (Kokai) No. 2008-034692
[Patent Document 4] Japanese Unexamined Patent Publication (Kokai) No. 2009-156719
[Patent Document 5] Japanese Unexamined Patent Publication (Kokai) No. 2014-053479
[Patent Document 6] Japanese Unexamined Patent Publication (Kokai) No. 2016-6825
[Patent Document 7] Japanese Unexamined Patent Publication (Kokai) No. 11-335120
[Patent Document 8] Japanese Unexamined Patent Publication (Kokai) No. 11-284238
[Patent Document 9] Japanese Unexamined Patent Publication (Kokai) No. 10-310497
[Patent Document 10] Japanese Unexamined Patent Publication (Kokai) No. 2014-75522
[Patent Document 11] International Publication WO 2011/071071
[Patent Document 12] Japanese Unexamined Patent Publication (Kokai) No. 2014-146760
[Patent Document 13] Japanese Unexamined Patent Publication (Kokai) No. 2004-309208

Non-Patent Document

[Non-Patent Document 1] Takashi Nakamura et al: Low Temperature Engineering Vol. 46, No. 3, 2011
[Non-Patent Document 2] Hiroyuki Fujishiro et al; Supercond. Sci. Technol. 28 (2015) 095018

SUMMARY

Problems to be Solved by the Invention

However, in the superconducting bulk bodies and the like disclosed in Patent Documents 1 to 12 and Non-Patent Documents 1 and 2 and the like, the available area of the uniform magnetic field space formed by the bulk magnet structure was limited. In addition, access to the space was restricted to access from the axial direction of the bulk magnet structure. As a result, the way in which the bulk magnet structure could be used was restricted. As a specific example, in the configuration of a conventional solenoid type bulk magnet, it is impossible to process a lateral surface of tubular shape, and it is possible to access the internal uniform magnetic field space only from the upper and lower surfaces. Therefore, there were the following three problems: 1) The antenna for the NMR analysis device needs to take such a form as a saddle type, a birdcage type, and a signal detection efficiency is low, 2) Since it is necessary to place a sample on a cold head of a freezer, the movement for loading and unloading of the sample is reciprocating movement and its mechanism is complicated, and 3) Similarly, since it is necessary to place a sample on a cold head of a freezer, it is difficult to perform a measurement while irradiating the sample with light. In the magnet composed of the wound coil of the superconducting wire as disclosed in Patent Document 13, it is possible to access the magnetic field space from a direction different from the axial direction, but the decrease in the central magnetic field strength becomes large, and in some cases, it may be necessary to include a coil that generates a magnetic field in the opposite direction in order to generate a uniform magnetic field.

The present invention has been made in view of the above problems, and it is an object of the present invention to provide a bulk magnet structure capable of realizing a further mode of use of the bulk magnet structure, and also an object of the present invention to provide a new and improved bulk magnet structure that can utilize a larger and more uniform magnetic field space and to provide a magnet system for NMR using the bulk magnet structure.

Means for Solving the Problems

In order to attain the above object, it is necessary to enable access to the measuring part from the horizontal direction (the direction perpendicular to the axial direction). However, in order to do so at present, as shown in reference 13, a strategy of partial opening has been utilized.

However, as a result of intensive studies, the inventors have found that there is a problem in that partial opening disturbs a magnetic field, and thus precise measurement cannot be carried out. The inventors have found that by spacing apart at least one pair of adjacent oxide superconducting bulk bodies in the central axial direction, in addition to enabling access from the horizontal direction, it is possible to realize a wider uniform magnetic field space, even though the oxide superconducting bulk bodies are spaced apart from each other, and thus the present invention was achieved. In order to attain the above objects, according to one aspect of the present invention, there is provided a bulk magnet structure comprising a plurality of oxide superconducting bulk bodies arranged such that their central axes are on the same line, and at least one outer circumferential reinforcing ring fitted to cover the outer circumferential surfaces of the plurality of oxide superconducting bulk bodies, wherein the plurality of oxide superconducting bulk bodies comprise at least a columnar oxide superconducting bulk body or a ring-shaped oxide superconducting body, and wherein at least one pair of adjacent oxide superconducting bulk bodies are spaced apart in the central axis direction and the bulk magnet structure has a space inside through which the central axis passes.

Note that the oxide superconducting bulk body contains at least a columnar oxide superconducting bulk body or a ring-shaped oxide superconducting bulk body. Therefore, the central axis of the oxide superconducting bulk body corresponds to the central axis of the columnar shape or the ring shape, and may extend in the direction parallel to the layering direction of the oxide bulk bodies The bulk magnet structure has a space inside of which a magnetic field space can be formed by the bulk magnet structure, wherein a sample and/or a device can be mounted, and can enable communication with the outside of the bulk magnet structure (in a direction perpendicular to the layering direction). Further, the central axis of the oxide superconducting bulk body passes through the space.

In order to attain the above objects, according to one aspect of the present invention, there is provided a bulk magnet structure comprising a plurality of oxide superconducting bulk bodies and at least one outer circumferential reinforcing ring fitted to cover the outer circumferential surfaces of the plurality of layered oxide superconductive bulk bodies, and a spacer layered together with the oxide superconducting bulk bodies, wherein the plurality of oxide superconducting bulk bodies comprise at least a columnar oxide superconducting bulk body or a ring-shaped oxide superconducting bulk body, and wherein the spacer has a space formed from at least a portion of the lateral circumferential portion to the interior thereof, and wherein the spacer is layered so that at least the central axis of the bulk magnet structure passes through the space.

Note that the bulk magnet structure is formed by layering oxide superconducting bulk bodies. Therefore, the central axis of the bulk magnet structure may correspond to the central axis of the oxide superconducting bulk body. The central axis of the oxide superconducting bulk body is as described above. Referring to FIG. 25*a*, the central axis of the bulk magnet structure corresponds to long dashed short dashed line drawn on the upper and lower sides of the paper surface, and the layering direction of the bulk magnet structure is parallel to this central axis. A space between the upper and lower oxide superconducting bulk bodies corresponds to the above-described space, and the central axis of the oxide superconducting bulk body passes through the space.

According to one aspect of the present invention, there is provided a bulk magnet structure comprising a plurality of oxide superconducting bulk bodies, at least one outer circumferential reinforcing ring fitted to cover the outer circumferential surfaces of the plurality of layered oxide superconducting bulk bodies, and a space, wherein the plurality of oxide superconducting bulk bodies comprises at least a columnar oxide superconducting bulk body or a ring-shaped oxide superconducting bulk body, and the space is capable of forming a magnetic field space by the bulk magnet structure, placing a sample and/or device and communicating with the outside of the bulk magnet structure (in a direction perpendicular to the layering direction).

The space may penetrate from a portion of the lateral circumferential portion of the bulk magnet structure to another portion of the lateral circumferential portion.

The space may be disposed in a central portion in the layering direction of the bulk magnet structure.

The spacer may be formed by a non-superconducting bulk body, and the non-superconducting bulk body may have a thermal conductivity of 20 W/(m·K) or more.

At least one of the oxide superconducting bulk bodies adjacent to the space in the layering direction of the bulk magnet structure may be the ring-shaped oxide superconducting bulk body.

At least one of the columnar oxide superconducting bulk bodies may be a stack in which a columnar oxide superconducting bulk body and a planar reinforcing plate are alternately arranged.

The material constituting the planar reinforcing plate has a thermal conductivity of 20 W/(m·K) or more and/or a tensile strength at room temperature of 80 MPa or more.

At least one of the ring-shaped oxide superconducting bulk bodies may be a stack in which a ring-shaped oxide superconducting bulk body and a planar ring are alternately arranged.

The material constituting the planar ring may have a thermal conductivity of 20 W/(m·K) or more and/or a tensile strength at room temperature of 80 MPa or more.

The ring-shaped oxide superconducting bulk body may have an inner circumferential reinforcing ring inside the body.

The material constituting the inner circumferential reinforcing ring may have a thermal conductivity of 20 W/(m·K) or more and/or a tensile strength at room temperature of 80 MPa or more.

A second inner circumferential reinforcing ring may be provided between the ring-shaped oxide superconducting bulk body and the inner circumferential reinforcing ring.

The material constituting the second inner circumferential reinforcing ring may have a thermal conductivity of 20 W/(m·K) or more and/or a tensile strength at room temperature of 80 MPa or more.

A second outer circumferential reinforcing ring may be provided between the oxide superconducting bulk body and the outer circumferential reinforcing ring.

The material constituting at least one of the outer circumferential reinforcing ring and the second outer circumferential reinforcing ring has a thermal conductivity of 20 W/(m·K) or more and/or a tensile strength at room temperature of 80 MPa or more.

The oxide superconducting bulk body may contain an oxide having a structure in which $RE_2BaCuO_5$ is dispersed in a monocrystalline $REBa_2Cu_3O_y$ (RE is one or two or more elements selected from rare earth elements, $6.8 \leq y \leq 7.1$).

At least one ring-shaped oxide superconducting bulk body may be disposed on at least one end in the layering direction of the plurality of oxide superconducting bulk bodies constituting the bulk magnet structure.

A plurality of the ring-shaped oxide superconducting bulk bodies may be successively layered from at least one end in the layering direction of the plurality of the oxide superconducting bulk bodies constituting the bulk magnet structure to a central portion in the layering direction of the bulk magnet structure.

At least one ring-shaped oxide superconducting bulk body may be disposed at one end in the layering direction of the plurality of the oxide superconducting bulk bodies constituting the bulk magnet structure, and at least one columnar oxide superconducting bulk body may be disposed at the other end in the layering direction.

In addition, in order to solve the above problems, according to another aspect of the present invention, there is provided a magnet system for NMR comprising a bulk magnet structure described above housed in a vacuum container, a cooling device for cooling the bulk magnet structure, and a temperature controller for adjusting a temperature of the bulk magnet structure.

The oxide superconducting bulk body constituting the bulk magnet structure may be in a magnetized state.

A sample insertion port may be formed at a lateral portion of the vacuum container.

Effect of the Invention

As described above, according to the present invention, it is possible to realize an additional mode of use of a bulk magnet structure, and such a bulk magnet structure provides a wider available uniform magnetic field space. Basically, when forming a magnetic field from above and below the magnet structure in the axial direction, since the bulk magnetic structure can freely access an external space in front-back direction and crosswise direction with respect to the axis, flexibility in shape and arrangement of a measurement sample, electric wave irradiation coil, antenna coil, magnetic field correction coil (room temperature shim) increases. As a specific example, corresponding to the description of [Problems to be Solved by the Invention] ([0017]), 1) it is easy to make the positional relationship such that a sample penetrates a solenoid type detection antenna and a signal detection efficiency determined by the shape of the coil and the sample positional relationship can be enhanced, and a measurement with a higher sensitivity than the conventional NMR analysis device becomes possible. 2) A sample can be exchanged only by moving the sample continuously in one direction from the lateral face, and thus a measurement efficiency can be improved. 3) By allowing access to the sample space from the axial direction (the magnetic field direction) and the direction perpendicular to the axis, it is easy to irradiate a light to a photoactive sample and observe a scattered light and a transmitted light. The above described implementations of mode of use are examples of the effect of the present invention. These effects are achieved by accessibility from a horizontal direction (a perpendicular direction to the axial direction). However, when trying to allow access from the horizontal direction, it was difficult to realize uniformity of the magnetic field. According to the present invention, it is possible to realize a wider uniform magnetic field space in addition to enabling access from the horizontal direction.

BRIEF DESCRIPTION OF DRAWINGS

FIG. 4B is a conceptual diagram of a current distribution and a magnetic field distribution of an oxide superconducting bulk body under magnetization condition 2.

FIG. 24B is a cross-sectional view (viewpoint from a second direction) showing a bulk magnet structure according to the same example.

EMBODIMENTS FOR CARRYING OUT THE INVENTION

Figure 1:
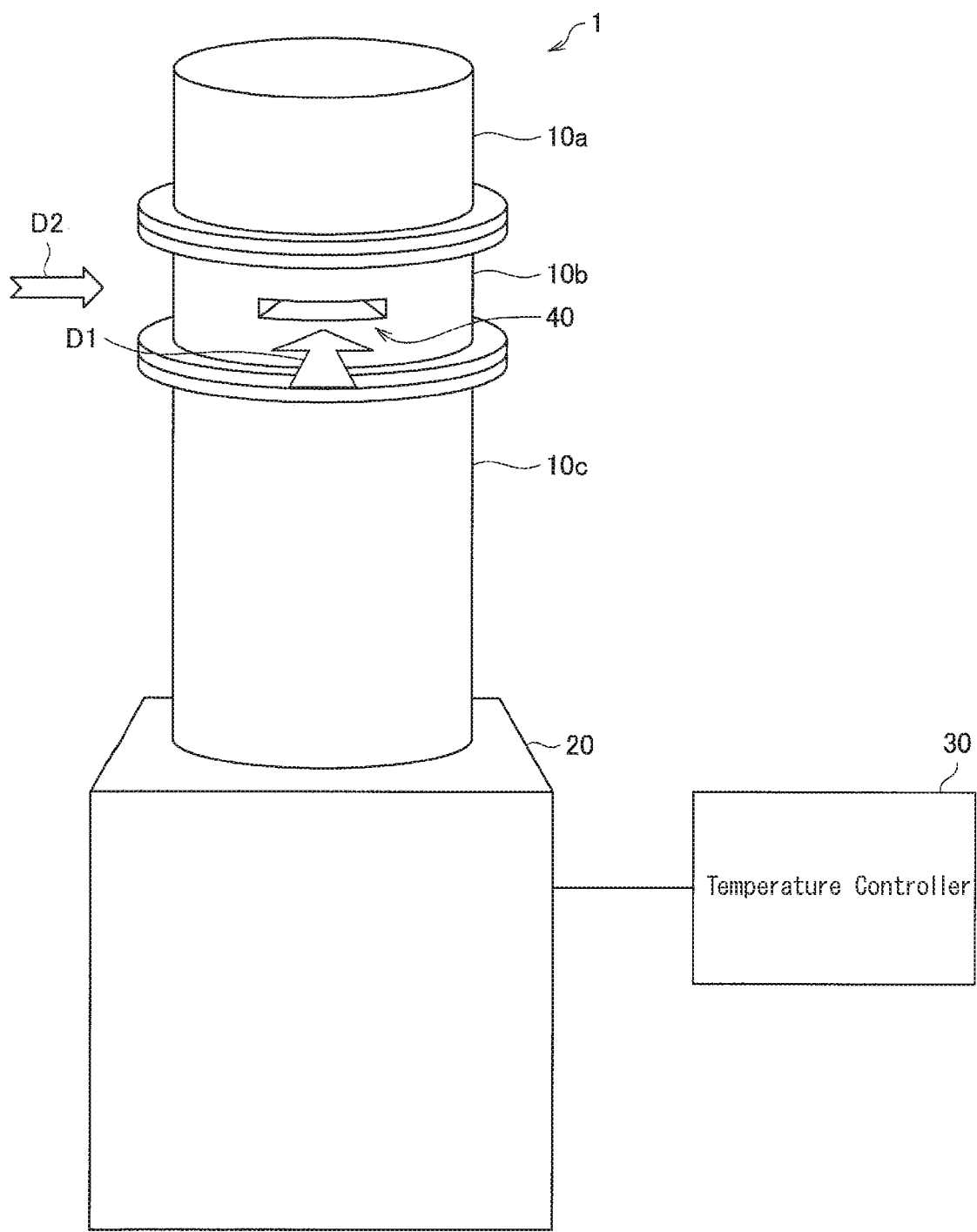
FIG. 1 is a schematic view showing an external appearance of a bulk magnet system for NMR according to this embodiment.

Preferred embodiments of the present invention will now be described in detail with reference to the accompanying drawings. In the present specification and the drawings, the same reference numerals are given to the constituent elements having substantially the same functional configuration to omit redundant explanations.

<Configuration of Oxide Superconducting Bulk Body>

First, the oxide superconducting bulk body used in an embodiment of the present invention will be described. The oxide superconducting bulk body used in this embodiment may desirably have a structure in which a non-superconducting phase typified by a $RE_2BaCuO_5$ phase (211 phase) or the like is dispersed, or preferably finely dispersed in a monocrystalline $REBa_2Cu_3O_{7-x}$ (so-called QMG (registered trademark) Material). The term "monocrystalline" as used herein means not only a perfect mono-crystal but also those having defects that are practically usable, such as low angle grain boundaries. RE in $REBa_2Cu_3O_{7-x}$ phase (123 phase) and $RE_2BaCu_5$ phase (211 phase) is a rare earth element consisting of Y, La, Nd, Sm, Eu, Gd, Dy, Ho, Er, Tm, Yb, Lu and combinations thereof. The 123 phase including La, Nd, Sm, Eu or Gd is out of the stoichiometric composition of 1:2:3, and Ba may partially be substituted in the site of RE in some cases. Also, in the 211 phase which is the non-superconducting phase, La and Nd are somewhat different from Y, Sm, Eu, Gd, Dy, Ho, Er, Tm, Yb and Lu, and it is known that they may lead a non-stoichiometric composition ratio of metal elements or a different crystal structure.

Substitution of Ba element as described above tends to lower the critical temperature. Also, substitution of Ba element tends to be suppressed in an environment with a lower oxygen partial pressure.

The 123 phase is formed by a peritectic reaction of the 211 phase with a liquid phase composed of a composite oxide of Ba and Cu.

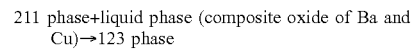
211 phase+liquid phase (composite oxide of Ba and Cu)→123 phase

Then, the temperature at which the 123 phase can be formed (Tf: 123 phase generation temperature) by this peritectic reaction generally relates to an ionic radius of the RE element, and Tf decreases as the ion radius decreases. In addition, Tf tends to decrease with a low oxygen atmosphere and Ag addition.

A material in which the 211 phase is finely dispersed in the monocrystalline 123 phase can be formed because unreacted 123 grains are left in the 123 phase when the 123 phase grows crystal. That is, the oxide superconducting bulk body is formed by the following reaction.

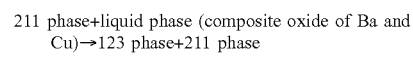
211 phase+liquid phase (composite oxide of Ba and Cu)→123 phase+211 phase The fine dispersion of the 211 phase in the oxide superconducting bulk body is extremely important from the viewpoint of Jc improvement. By adding a trace amount of at least one of Pt, Rh or Ce, grain growth of the 211 phase in the semi-molten state (a state composed of the 211 phase and the liquid phase) is suppressed, and as a result, the 211 phase in the material is miniaturized to about 1 μm. From the viewpoints of the amount at which the miniaturization effect appears and the material cost, it is desired that the addition amount is 0.2 to 2.0% by mass for Pt, 0.01 to 0.5% by mass for Rh, 0.5 to 2.0% by mass for Ce. A part of the added Pt, Rh or Ce is solid-solved in the 123 phase. In addition, an element which cannot be solid-solved forms a composite oxide with Ba or Cu to be scattered in the material.

Further, the bulk oxide superconducting body constituting the magnet needs to have a high critical current density (Jc) even in a magnetic field. In order to satisfy this requirement, it is necessary to be a monocrystalline 123 phase which does not include a high angle grain boundary which leads to a superconductively weak bond. In order to have even higher Jc characteristics, a pinning center for stopping the movement of the magnetic flux is required. The finely dispersed 211 phase functions as this pinning center, and thus it is preferable that a large number of the 211 phases are finely dispersed. As mentioned earlier, Pt, Rh and Ce have a function to promote miniaturization of the 211 phase. In addition, the possibility of $BaCeO_3$, $BaSiO_3$, $BaGeO_3$, $BaSnO_3$ or the like as a pinning site is known. In addition, a non-superconducting phase such as 211 phase mechanically strengthens the superconducting body by being finely dispersed in the 123 phase which is easy to cleave, and it also plays an important role to make the bulk material usable.

Figure 23:
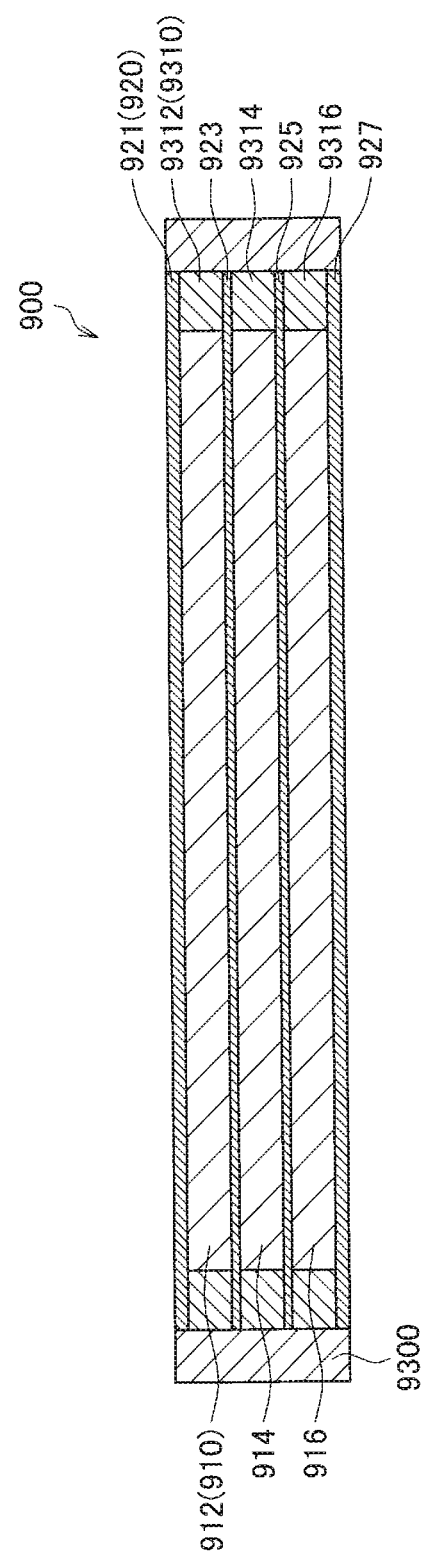
FIG. 23 shows a partial cross-sectional view of a bulk magnet formed by a columnar stack according to a second configuration example of a columnar stack, taken along the center axis of the bulk magnet.

From the viewpoint of Jc characteristics and mechanical strength, the ratio of 211 phase in 123 phase is preferably 5 to 35% by volume. In addition, the material generally contains 5 to 20% by volume of voids (air bubbles) of about 50 to 500 μm. When Ag is added, Ag or Ag compound of about 1 to 500 μm in size is included in an amount from more than 0% by volume to no more than 25% by volume, depending on the added amount. FIG. 23.

In addition, when oxygen deficiency amount (x) in the material after crystal growth is about 0.5, a semiconductor-like temperature-dependent change in resistivity are exhibited. By annealing this in each RE system at 350° C. to 600° C. for about 100 hours in an oxygen atmosphere, oxygen will be incorporated into the material, and the oxygen deficiency amount (x) becomes 0.2 or less, and good superconducting properties are exhibited. At this time, a twin crystal structure is formed in the superconducting phase. However, the material including this aspect will be referred to as a monocrystalline state in the specification.

Note that the "oxide superconducting bulk body" in the present specification means an oxide superconducting bulk body partly or entirely containing an oxide superconducting bulk body having an oxide microstructure for expressing the above-described superconducting properties For example, the "oxide superconducting bulk body" can encompass a bulk body entirely made of an oxide superconductor (i.e., "bulk body") and a stack composed of a combination of an oxide superconducting bulk body and a non-superconducting bulk body (i.e., "stack").

In the present specification, the "bulk body" is generally described as meaning an oxide superconducting bulk body, but when it is not necessary to particularly distinguish the "bulk body" from the "stack", they are collectively referred to as "bulk body" in some cases. In addition, when merely described as "bulk body" or the like, the shape thereof (ring shape or columnar shape) is not limited.

Next, a bulk magnet system for NMR using the bulk magnet structure according to this embodiment will be described.

<Configuration of Bulk Magnet System for NMR>

Figure 2:
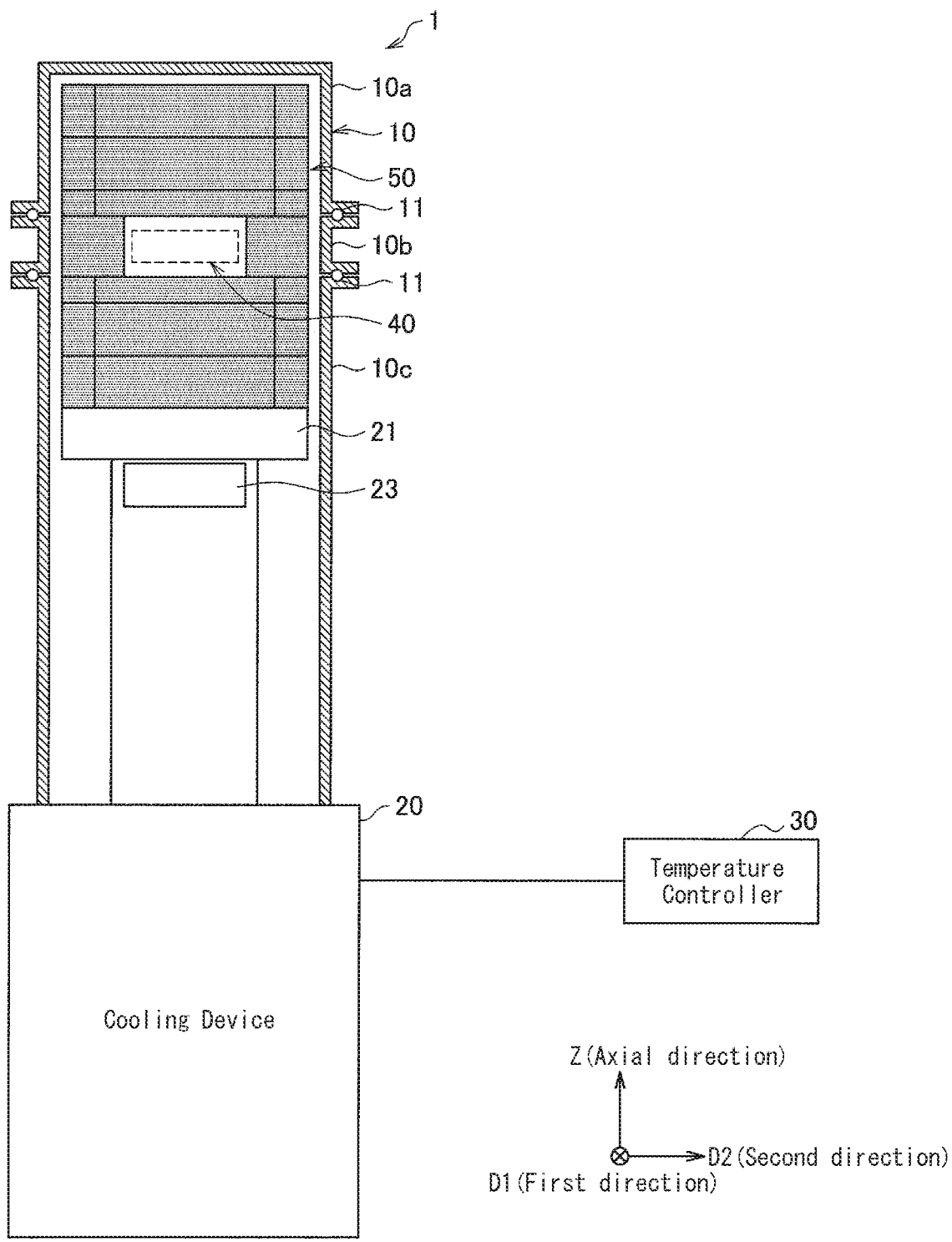
FIG. 2 is an explanatory diagram showing a schematic configuration of a bulk magnet system for NMR according to the same embodiment.

FIG. 1 and FIG. 2 are a schematic view showing an appearance of a bulk magnet system 1 for NMR (hereinafter also simply referred to as "system 1") according to this embodiment, and an explanatory view of a schematic configuration thereof. As shown in FIGS. 1 and 2, the system 1 according to the present embodiment comprises a vacuum heat insulation container 10 in which a bulk magnet structure 50 is housed, a cooling device 20, and a temperature controller 30.

The bulk magnet structure 50 is disposed in the vacuum heat insulation container 10 in a state of being placed on the cold head 21 of the cooling device 20. As a result, the bulk magnet structure 50 is thermally connected to the cooling device 20 such that the bulk magnet structure 50 can be cooled by the cooling device 20. Further, the cold head 21 is provided with a heater 23 for raising a temperature of the bulk magnet structure 50. Further, one or more of temperature sensors (not shown) for measuring temperatures inside the container may be installed in the vacuum heat insulation container 10. The temperature sensor may be installed, for example, at the upper part of the vacuum heat insulation container 10 or in the vicinity of the cold head 21 on which the bulk magnet structure 50 is placed. Further, after disposing the bulk magnet structure 50 on the cold head 21, wrapping a radiant heat insulating sheet (for example, an aluminum vapor deposited film and a spacer stack) around the bulk magnet structure 50 is desirable from the viewpoint of improvement of heat insulation conditions (not shown).

The cooling device 20 is a device for cooling the bulk magnet structure 50. As the cooling device 20, for example, a refrigerant such as liquid helium or liquid neon, a GM freezer (Gifford-McMahon cooler), or a pulse tube freezer or the like can be used. The cooling device 20 is controlled and driven by the temperature controller 30. The temperature controller 30 controls the cooling device 20 so that the temperature of the bulk magnet structure 50 reaches a desired temperature according to each step of magnetization.

In addition, the vacuum heat insulation container 10 shown in FIGS. 1 and 2 is composed of a first container 10a, a second container 10b and a third container 10c. Each container is provided with a flange for connection with another container, and a sealing material such as an O ring 11 for vacuum sealing is appropriately provided between the flanges to be connected. These flanges are connected by screwing or the like (not shown). As shown in FIG. 1, a space 40 (52c) is provided inside the second container 10b. This space 40 (52c) is provided from the sample insertion port provided on the lateral surface of the second container 10b to the inside, communicates with the external space, and does not communicate with the vacuum heat insulating layer in the vacuum heat insulation container 10. That is, the space 40 (52c) is provided for placing a sample or the like in the magnetic field space formed by the bulk magnet structure 50 from the outside of the system 1. In addition, although the space 40 shown in FIGS. 1 and 2 penetrates the second container 10b in the horizontal direction, the present invention is not limited to this example, and the space 40 does not have to penetrate.

Incidentally, among directions perpendicular to the central axial direction of the bulk magnet structure 50, a direction from the sample insertion port communicating the space 40 with the external space, toward the axis is defined as a first direction D1, and a direction orthogonal to the direction D1 is defined as a second direction D2.

<Magnetization Process>

Next, an example of the magnetization process of the bulk magnet structure 50 according to this embodiment will be described with reference to FIG. 3 and FIGS. 4A to 4C. Magnetization of the bulk magnet structure 50 can be performed by, for example, a magnetic field generating device which houses a tubular superconducting magnet. Such a magnetic field generating device is provided in a so-called magnetizing station, and after the bulk magnet structure 50 included in the system 1 is magnetized in the magnetizing station, the system 1 is supplied to the user.

Figure 3:
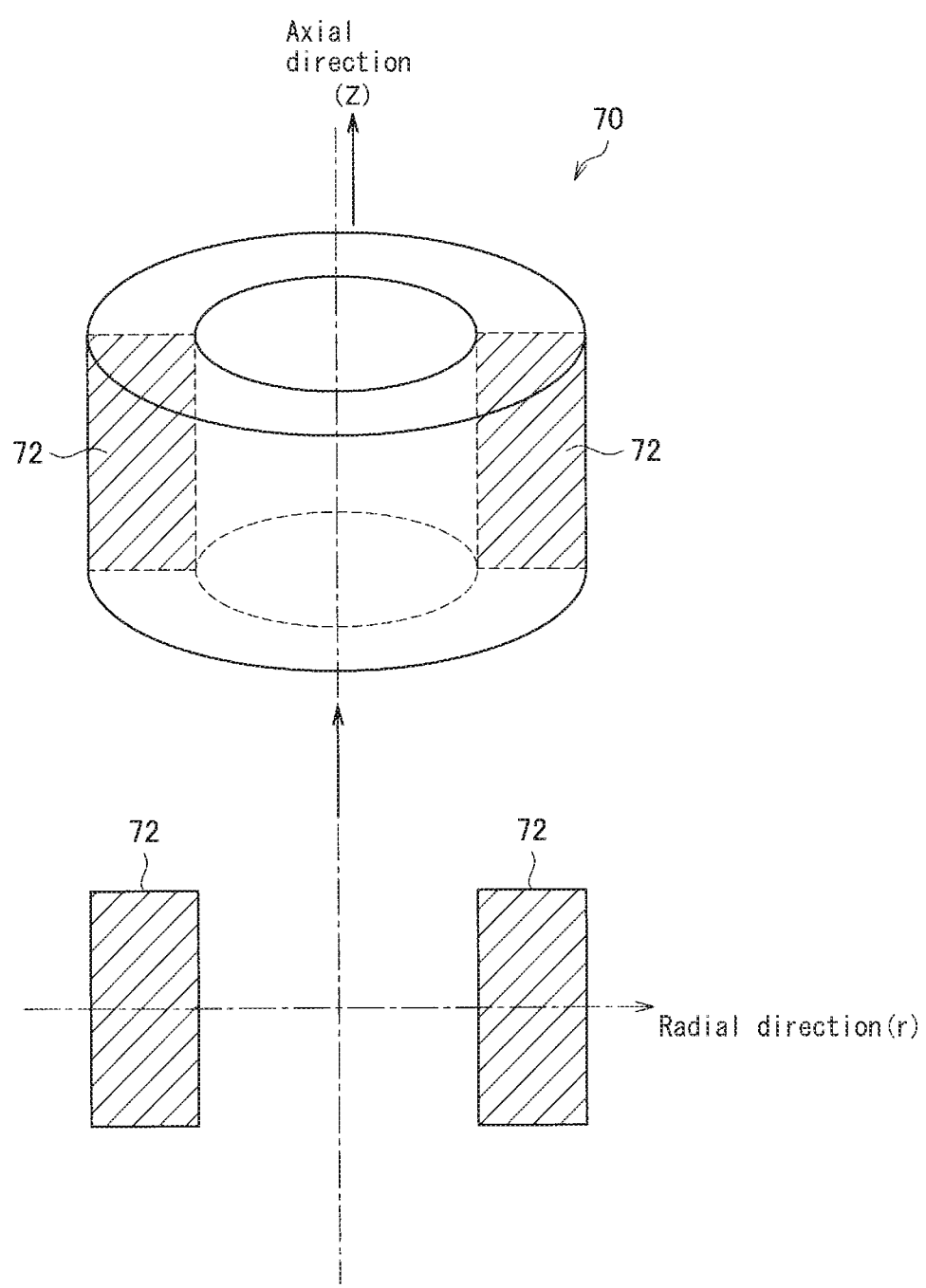
FIG. 3 is an explanatory view showing an external view and a cross-sectional view of a ring-shaped oxide superconducting bulk body.
Figure 4A:
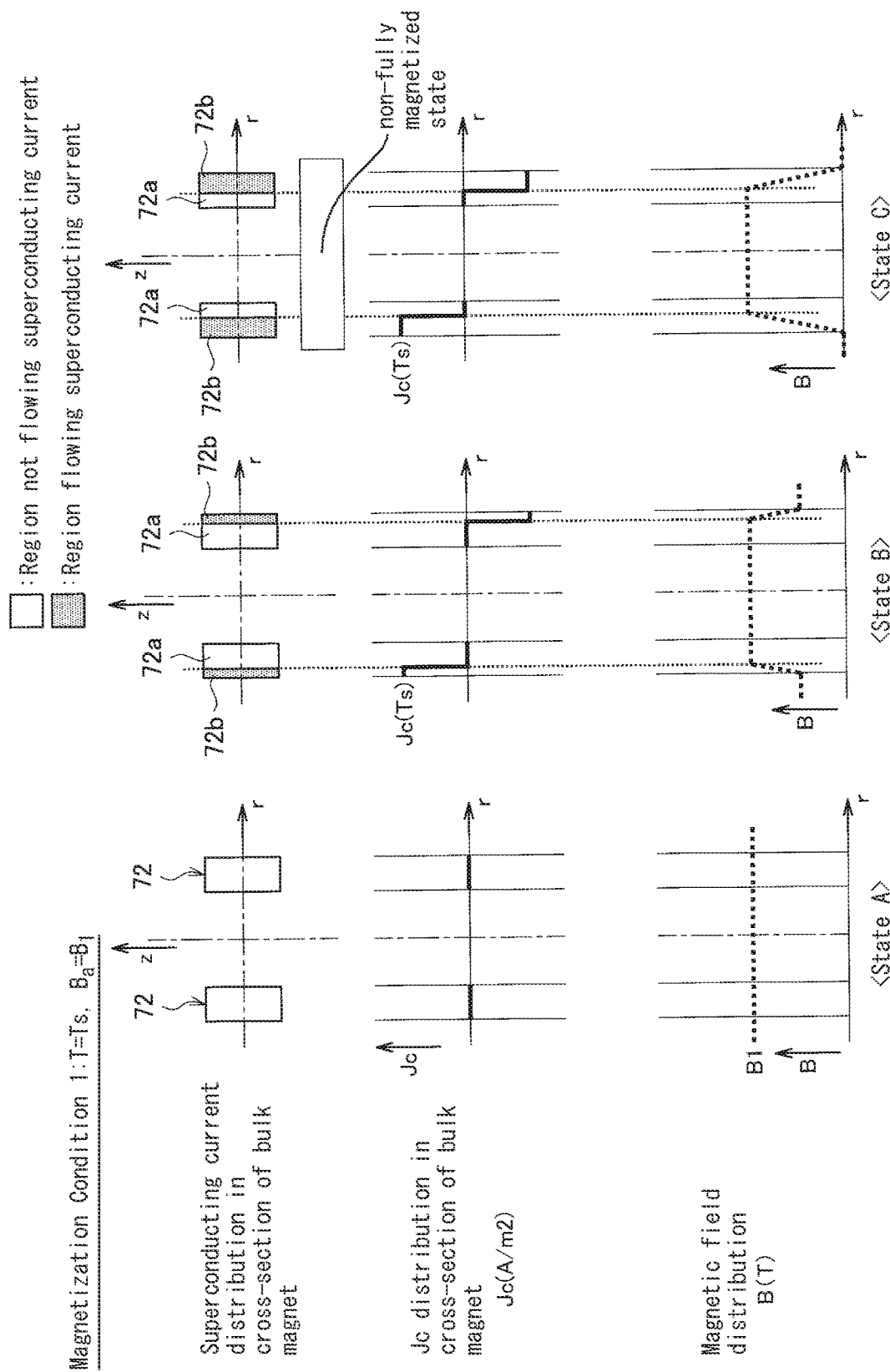
FIG. 4A is a conceptual diagram of a current distribution and a magnetic field distribution of an oxide superconducting bulk body under magnetization condition 1.
Figure 4C:
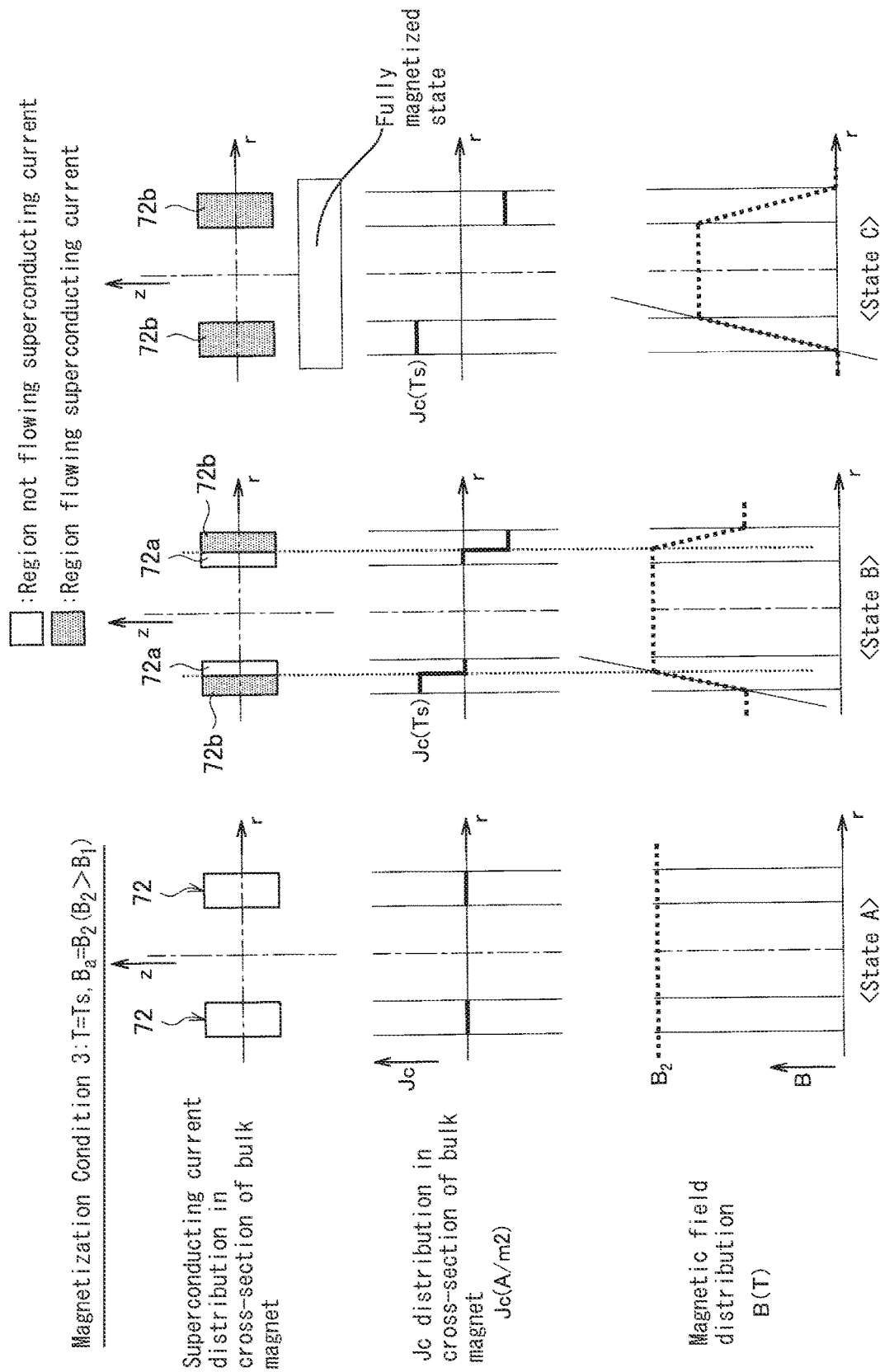
FIG. 4C is a conceptual diagram of a current distribution and a magnetic field distribution of an oxide superconducting bulk body under magnetization condition 3.

In this case, for example, the magnetized state of the ring-shaped oxide superconducting bulk body 70 as shown in FIG. 3 is considered under several magnetization conditions. FIGS. 4A to 4C are diagrams showing magnetized states in the bulk magnet structure in the basic magnetization step: under the respective magnetization conditions, the magnetic field applied to the bulk magnet structure in the normal conduction state is brought to a superconductive state by cooling the bulk magnet structure, and then the applied magnetic field is removed. In FIGS. 4A to 4C, a region 72a where the superconducting current does not flow and a region 72b where the superconducting current flows are shown, using the cross-sectional view 72 of the superconducting bulk body 70 along the axial direction and the radial direction shown in FIG. 3, along with the critical current density distribution and the magnetic field distribution in the cross-section.

Here, as a uniformity evaluation index of the magnetic field distribution, a ratio of the difference between the maximum magnetic field strength and the minimum magnetic field strength with respect to the average magnetic field strength in a certain region is expressed in ppm. In MRI magnets, high magnetic field uniformity as high as about ppm order is often required as a uniformity evaluation index of the applied magnetic field distribution in a region where it is desired to make the magnetic field distribution uniformized (that is, the magnetic field uniformization region). On the other hand, the uniformity of the magnetic field which can be generated by a magnetic field generator which is not mainly intended to generate a highly uniform magnetic field such as by NMR or MRI is relatively low, and the magnetic field uniformity required in the magnetic field uniformization region is often 100 ppm or more as indicated by the uniformity evaluation index of the applied magnetic field distribution.

Incidentally, the magnetic field strength at a certain point can be roughly evaluated based on Hall element or a highly-sensitive magnetic field measuring device (for example, Teslameter (manufactured by Metrolab)), the half value width of NMR signal, and the like. In addition, the maximum magnetic field strength and the minimum magnetic field strength are the highest magnetic field strength value and the lowest magnetic field strength value in a certain region, and the average magnetic field strength is the average value of the maximum magnetic field strength and the minimum magnetic field strength.

(Magnetization Condition 1: $T=T_S$, $B_a=B_1$)

First, as the magnetization condition 1, a ring-shaped oxide superconducting bulk body in a normal conduction state was placed in a magnetic field $B_1$, cooled it to a temperature Ts not higher than the superconducting transition temperature (Tc), and then the applied magnetic field was gradually decreased. The superconducting current distribution and magnetic field distribution in the oxide superconducting bulk body at this time are shown in FIG. 4A. The state A is in a state before demagnetization, and no superconducting current flows in the oxide superconducting bulk body. As the applied magnetic field is gradually reduced, as shown in the state B, a region 72b in which the superconducting current having the value of the critical current density Jc (Ts) flows appears from the outer circumferential portion in the ring-shaped oxide superconducting bulk body. After a further reduction of the applied magnetic field, if the applied magnetic field is reduced to zero, the region 72 b in which the superconducting current having the critical current density Jc (Ts) flows further expands inward as shown in the state C, as shown in the state C. In the magnetization condition 1, as shown in the state C, even when the applied magnetic field becomes zero, there is a region 72a in which no superconducting current flows in the cross section of the oxide superconducting bulk body. Such a state is hereinafter referred to as a "non-fully magnetized state".

(Magnetization Condition 2: $T=T_h$ ($T_h>T_S$), $B_a=$

Next, in the magnetization condition 2, the applied magnetic field is the same as the magnetization condition 1, but the oxide superconducting bulk body was brought to temperature $T_h$ higher than the temperature $T_S$ under the magnetization condition 1. In the magnetization condition 2 where the temperature is higher than that in the magnetization condition 1 and the critical current density Jc is low, as shown in FIG. 4B, in the state A before demagnetization, like the magnetization condition 1, no superconducting current flows in the oxide superconducting bulk body. As the applied magnetic field is gradually reduced, as shown in the state B, a region 72b in which the superconducting current having the value of the critical current density Jc (Ts) flows appears from the outer circumferential portion in the ring-shaped oxide superconducting bulk body. At this time, a region 72b in which the superconducting current flows expands to the inner portion at an earlier stage than in the magnetization condition 1. Then, in the state C where, after a further reduction of the applied magnetic field, the applied magnetic field is reduced to zero, a superconducting current flows through the entire cross section of the oxide superconducting bulk body. Such a state is hereinafter referred to as a "fully magnetized state".

(Magnetization Condition 3: $T=T_S$, $B_a=B_2$ ($B_2>B_1$))

On the other hand, in the magnetization condition 3, the magnetization temperature was the same as in the magnetization condition 1, but the applied magnetic field was made higher than in the magnetization condition 1. Under such magnetization conditions, superconducting current does not flow in the oxide superconducting bulk body as in the magnetization conditions 1 and 2 in the state A before demagnetization, as shown in FIG. 4C. As the applied magnetic field is gradually reduced, as shown in the state B, a region 72b in which the superconducting current having the value of the critical current density Jc (Ts) flows appears from the outer circumferential portion in the ring-shaped oxide superconducting bulk body. At this time, like in the magnetization condition 2, a region 72b in which the superconducting current flows expands to the inner portion at an earlier stage than in the magnetization condition 1. Then, in the state C where, after a further reduction of the applied magnetic field, the applied magnetic field is reduced to zero, a superconducting current flows through the entire cross-section of the oxide superconducting bulk body, and is in the fully magnetized state.

Further, when paying attention to the gradient of the magnetic flux density in the cross-section of the oxide superconducting bulk body, it can be seen from FIG. 4B and FIG. 4C that the gradient of the magnetic flux density is proportional to the critical current density Jc.

Incidentally, in FIGS. 4A to 4C, three magnetization conditions are shown assuming that the critical current density Jc is constant (that is, it does not change), with respect to a temperature. However, in fact, it may decrease logarithmically with time. Therefore, the magnetic flux captured in the ring-shaped oxide superconducting bulk body may decrease with time. This phenomenon that gradually decreases with time is called creep.

However, in the case of the non-fully magnetized state as in the magnetization condition 1, even if the critical current density Jc decreases due to creep, the superconducting current will start to flow in the region where the superconducting current has not yet flowed to compensate the flow reduction of the critical current density Jc. Therefore, the magnetic flux inside the oxide superconducting bulk body decreases only slightly as the current distribution changes.

On the other hand, in the case of the magnetization conditions 2 and 3, all the reduction in the critical current density Jc due to creep leads to a change in the magnetic flux density in the oxide superconducting bulk body, and significant creep of the magnetic field occurs.

Furthermore, in FIGS. 4A to 4C, a conceptual view of a ring-shaped oxide superconducting bulk body that is sufficiently long in the axial direction is shown, but since the actual length in the axial direction is finite. Therefore, a bulk magnet located at the end in the axial direction does not have an adjacent bulk magnet on one side. Therefore, since the magnetic field rapidly decreases and the magnetic field gradient increases. Then, a large critical current flows, and accordingly, a region where the critical current flows expands to the inner circumference side. As a result, the critical current density Jc distribution in the cross-section of the oxide superconducting bulk body penetrates more inwardly at the upper and lower end portions, and the magnetic field strength captured at the upper and lower end portions decreases.

In the actual magnetization process for the bulk magnet structure 50, the magnetization process is controlled, so that a desired magnetized state is obtained in consideration of the creep, the change in the distribution of the critical current density Jc at the end of the cross-section, and a reduction in the decrease of the magnetic field strength.

An example of the magnetization process of the bulk magnet structure 50 according to this embodiment has been described above.

Hereinafter, a specific configuration example of the bulk magnet structure 50 according to this embodiment will be described.

First Embodiment

Figure 5A:
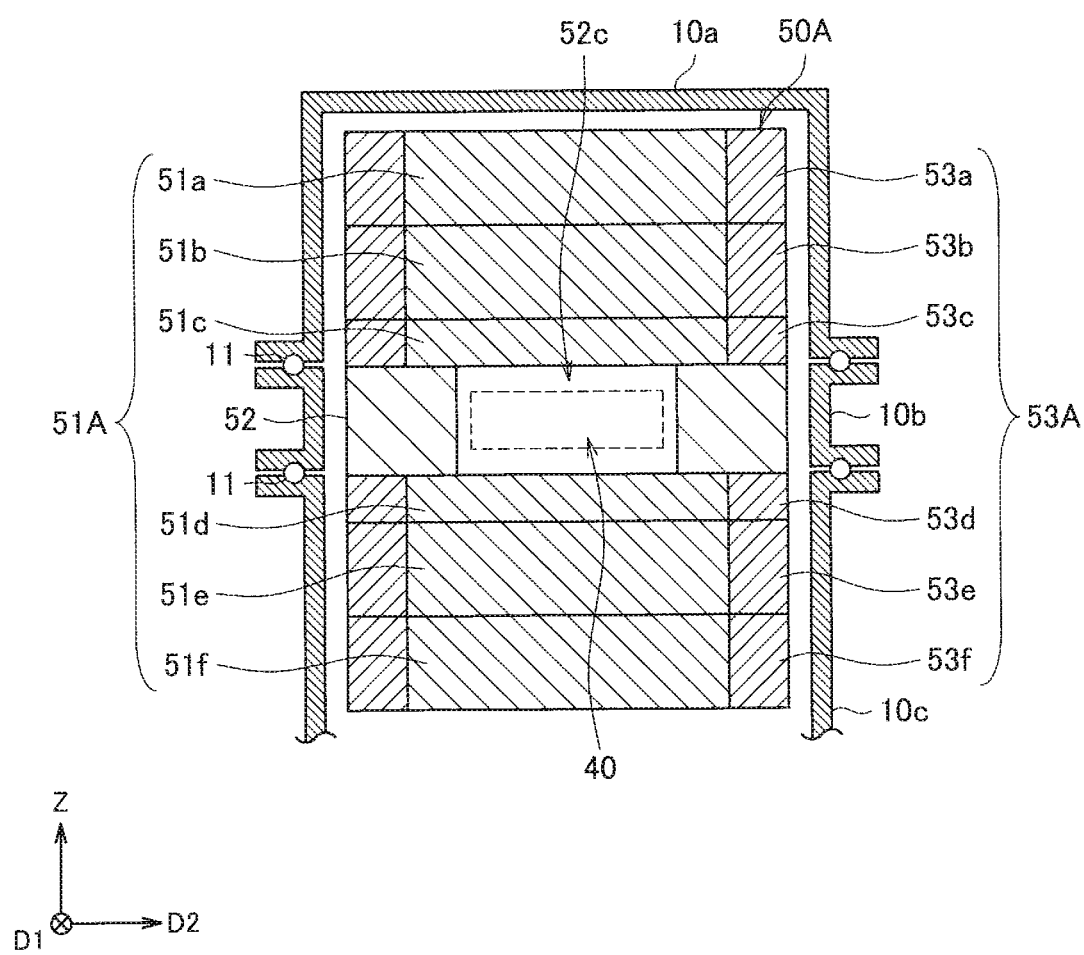
FIG. 5A is a cross-sectional view (viewpoint from a first direction) showing an example of a bulk magnet structure according to a first embodiment of the present invention.
Figure 5B:
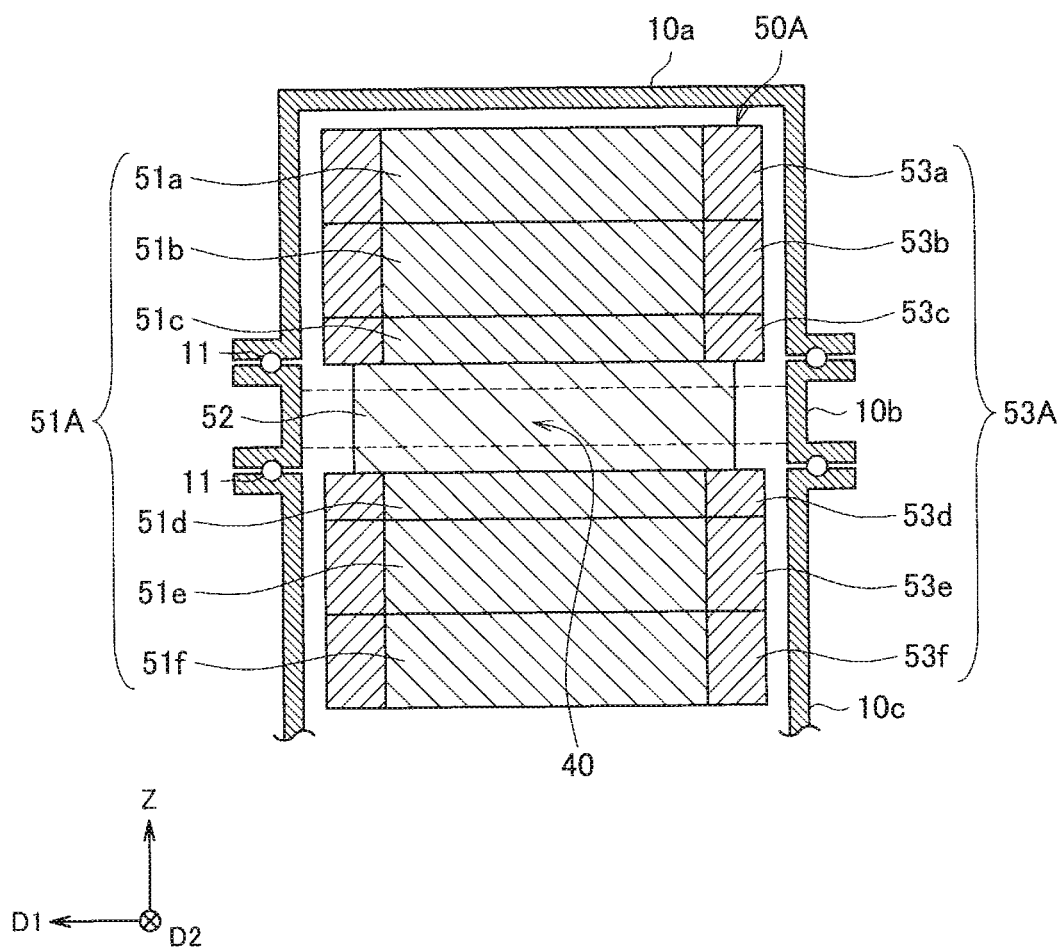
FIG. 5B is a cross-sectional view (viewpoint from a second direction) showing an example of a bulk magnet structure according to the same embodiment.
Figure 5C:
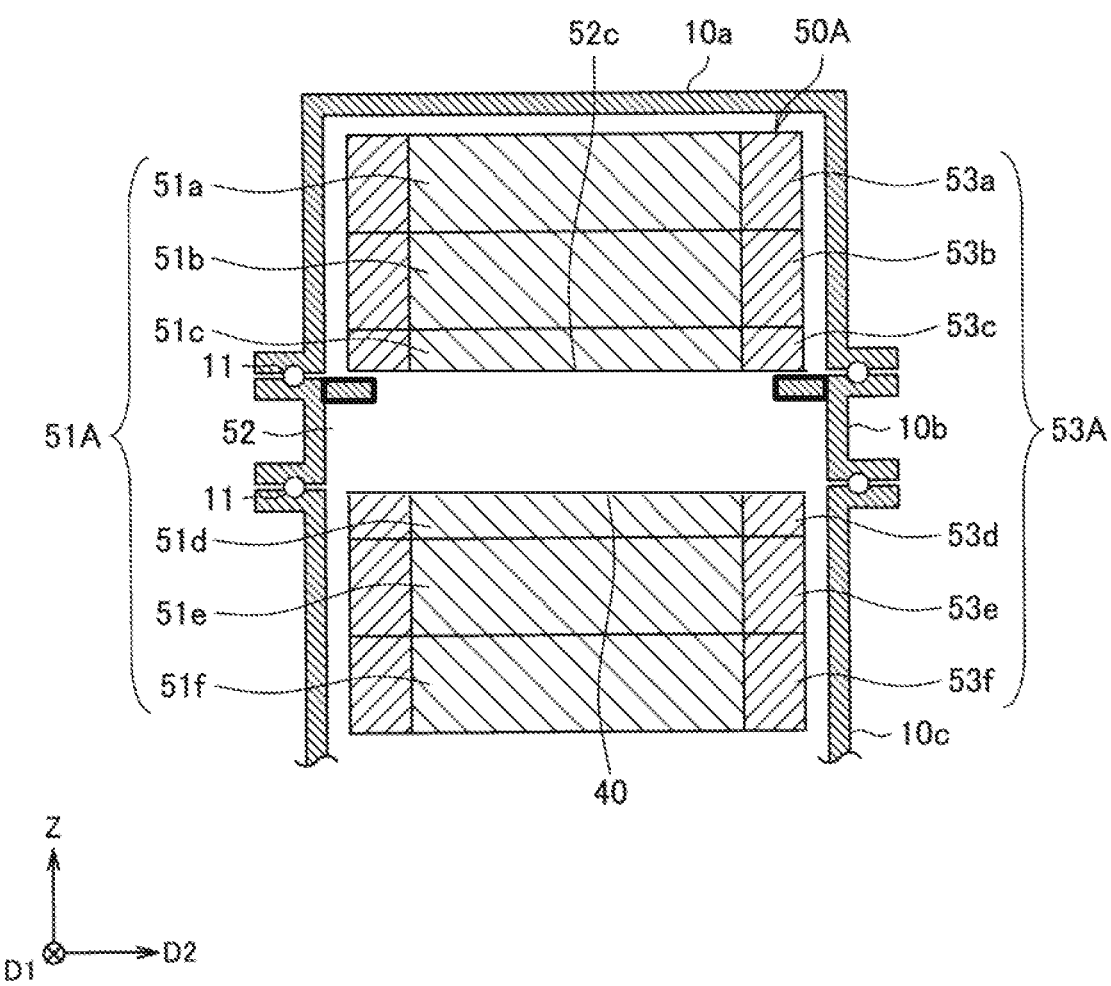
FIG. 5C is a cross-sectional view (when no spacer is used) showing an example of a bulk magnet structure according to the same embodiment.

FIGS. 5A, 5B and 5C are cross-sectional views showing an example of a bulk magnet structure 50A according to a first embodiment of the present invention. FIG. 5A is a cross-sectional view as seen from the first direction D1, and FIG. 5B is a cross-sectional view as seen from the second direction D2. As shown in FIGS. 5A and 5B, the bulk magnet structure 50A according to this embodiment comprises a bulk body portion 51A composed of a plurality of columnar bulk bodies 51a-51f, a space 52c, 40 (which may be formed by the spacer 52) between bulk bodies 51a-51c and bulk bodies 51d-51f, and an outer circumferential reinforcing ring portion 53A composed of outer circumferential reinforcing rings 53a-53f fitted to the outer circumferential surface of each of the bulk bodies 51a-51f. It is preferable to use solder for bonding each of the outer circumferential reinforcing rings 53a-53f and each of the bulk bodies 51a-51f. In this case, it is more preferable to deposit silver on the outer circumferential surface of each of the bulk bodies 51a-51f in advance so as to improve the spread of the solder and to reduce the electrical contact resistance. Incidentally, in the following description, the configuration in which the bulk body and the outer circumferential reinforcing ring are integrated is sometimes referred to as "bulk magnet".

The bulk magnet structure 50A is formed by layering the respective bulk bodies 51a-51f such that their central axes are aligned to each other. The outer diameters of the respective bulk bodies 51a-51f are desirably the same in design. As shown in FIGS. 5A and 5B, the thickness of the bulk bodies 51a, 51b, 51e and 51f in the axial direction may be larger than the thickness in the axial direction of the bulk bodies 51c and 51d, but such thicknesses are not particularly limited. In addition, the number of layering of the bulk bodies shown in FIGS. 5A, 5B and 5C is an example, and the number thereof is not particularly limited.

As shown in FIGS. 5A and 5B, the spacer 52 according to this embodiment is layered together with the respective bulk bodies such that the spacer is disposed between the bulk bodies 51a-51c and the bulk bodies 51d-51f. That is, the spacer 52 is disposed in the central portion in the layering direction of the bulk magnet structure 50A. In addition, the second container 10b is disposed at a position corresponding to the spacer 52.

Incidentally, as shown in FIG. 5C, without using the spacer 52, the upper bulk body portions 51a-51c and the outer circumferential reinforcing rings 53a-53c, and the lower bulk body portions 51d-51f and the outer circumferential reinforcing rings 53d-53f may be spaced apart from each other. This may be realized by supporting the upper bulk body portions 51a-51c and the outer circumferential reinforcing rings 53a-53c with the flange above the second container 10b, which protrudes in the direction of the central axis. In this case, the lower bulk body portions 51d-51f can be cooled in a state of being placed on the cold head 21 of the cooling device 20. The upper bulk body portions 51a-51c may be cooled by using a refrigerant (helium gas or the like) after forming the outer wall in a double structure and providing a vacuum heat insulation layer between the double outer walls.

Figure 6A:
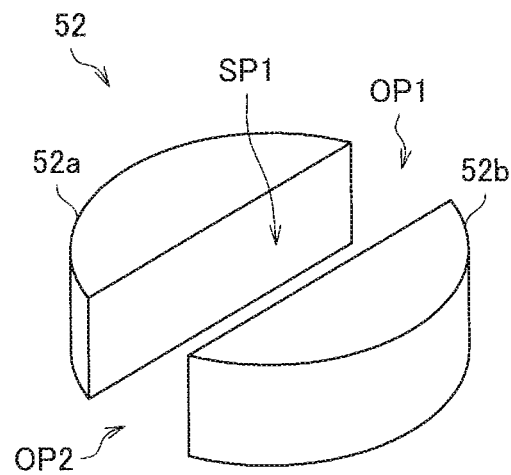
FIG. 6A is a schematic diagram showing an example of a spacer according to the same embodiment.

FIG. 6A is a schematic diagram showing an example of the spacer 52 according to this embodiment. As shown in FIG. 6A, the spacer 52 is configured by two opposed spacer members 52a and 52b. Between the two opposing spacer members 52a and 52b, a space SP1 is formed where at least a part of the lateral circumferential portion is opened. That is, the spacer 52 opens a part of the lateral circumferential portion and forms a space SP2 connecting the opening portions OP1 and OP2 from the lateral circumferential portion to the inside. As shown in FIGS. 5A and 5B, for example, such spacer members 52a and 52b can be formed from a columnar member having the same diameter as the outer diameter of the outer circumferential reinforcing ring, for example, by removing the portion penetrating the member in the in-plane direction of the edge surface of the member.

Figure 7:
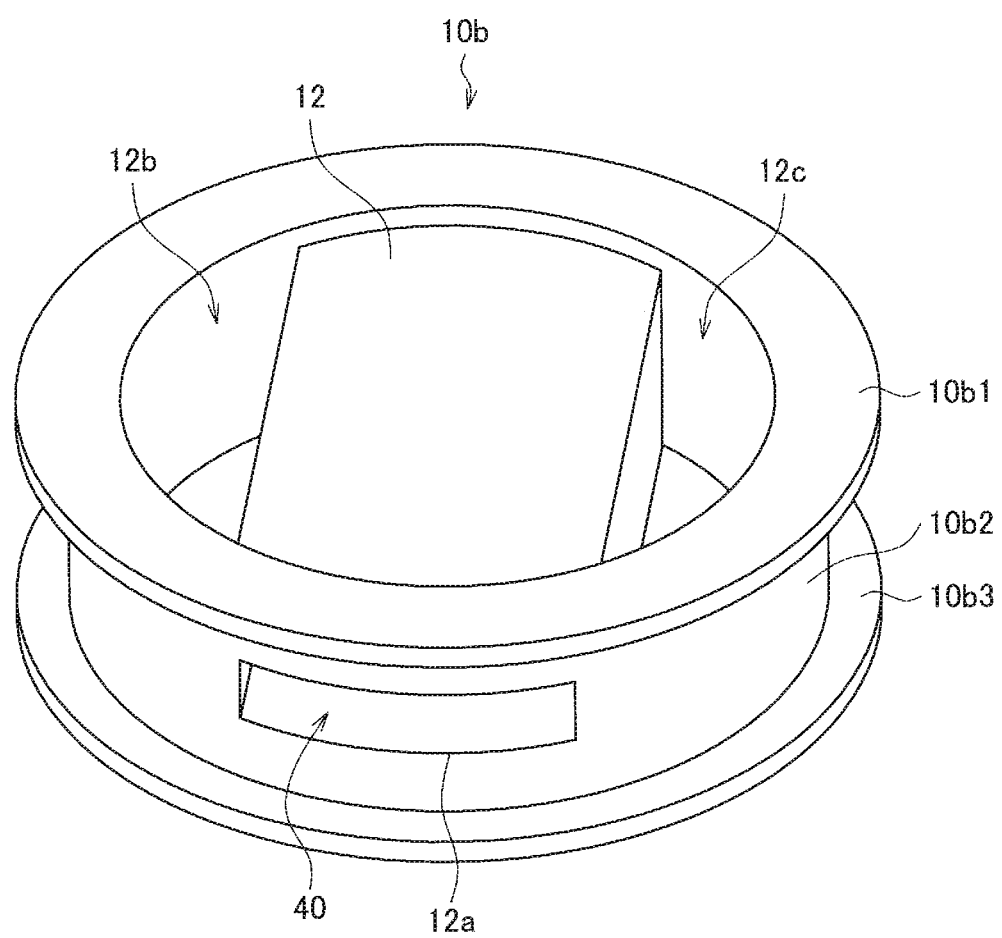
FIG. 7 is a schematic view showing an example of a second container according to the same embodiment.

FIG. 7 is a schematic view showing an example of the second container 10b. As shown in FIG. 7, the second container 10b is composed of an upper flange 10b1, a tubular portion 10b2 and a lower flange 10b3. The upper flange 10b1 and the lower flange 10b3 are connected to the upper surface and the lower surface of the tubular portion 10b2. In columnar portion 10b2, there is provided a tubular connecting member 12 which connects the opening 12a provided on the lateral surface of the columnar portion 10b2 and the other opening (not shown). A space 40 is formed inside the connecting member 12. Between the connecting member 12 and the columnar portion 10b2, housing spaces 12b and 12c are formed, and these spaces can accommodate the space 52c or the spacer members 52a and 52b.

Referring again to FIGS. 5A and 5B, a first space 52c enclosed by the bulk bodies 51c and 51d directly above and directly below thereof is formed inside the spacers 52 accommodated in the housing spaces 12b and 12c of the second container 10b. The spacer members 52a and 52b are arranged so that the first space 52c passes through the central axis (rotational symmetric axis) of the bulk magnet structure 50A. That is, in the bulk magnet structure 50A, the spacer 52 is formed so that the outer surface on the arc side of the spacer members 52a and 52b is continuous with the outer circumferential surface of the outer circumferential reinforcing ring 53C and the space between the spacer members 52a and 52b is arranged so as to pass through the central axis of the bulk magnet structure 50A. Then, the second container 10b is arranged so that the connecting member 12 of the second container 10b longitudinally crosses the first space 52c. In FIG. 5C, the spacer 52 is not used and a larger space 52c can be used.

When the bulk magnet structure 50A is magnetized in an external magnetic field, various magnetic field spaces can be generated by the bulk magnet structure 50A depending on the magnetization conditions. The magnetic field distribution in such a magnetic field space is appropriately adjusted by the strength distribution of the applied external magnetic field, the cooling temperature of the bulk magnet structure 50A, the thickness of the space 52c or the spacer 52 in the axial direction, the outer diameter of the bulk body portion 51A or layering conditions.

With the configuration of the bulk magnet structure 50 A shown in FIGS. 5A, 5B and 5C, the magnetic field space formed in the central portion of the bulk magnet structure 50A can be laterally accessible, not from axial direction of the bulk magnet structure 50A (For example, from the first direction D1 orthogonal to the axial direction). It is possible to realize a so-called split type bulk magnet structure. This makes it possible to further increase the modes of use of the magnetic field space at room temperature than in the prior art. For example, when the bulk magnet structure 50A is used as an NMR device, it is possible to flexibly set a selection of types of sample to be inserted into the space 40 and methods of inserting a sample.

In addition, with such a configuration, a physical space around the magnetic field space formed in the central portion of the bulk magnet structure 50A is formed to be large. Thereby, it is possible to secure a wide work space for using the magnetic field space. For example, when the bulk magnet structure 50A is used for an NMR device, various devices such as a correction magnetic field coil, a signal detection coil or an electromagnetic wave irradiation coil can be arranged with higher flexibility in such a work space. That is, it is possible to further enhance the functions of the NMR device. In this way, it is possible to realize further modes of use of the bulk magnet structure.

Basically, when forming a magnetic field from above and below in the axial direction, a flexibility in shape and arrangement of the measurement sample, electromagnetic wave irradiation coil, antenna coil, magnetic field correction coil (Room temperature shim) increases, since the external space can freely be accessed in a front-back direction and a crosswise direction perpendicular to the axis. As a more specific example, 1) it is easy to make the positional relationship such that a sample penetrates a solenoid type detection antenna and a signal detection efficiency determined by the shape of the coil and the sample positional relationship can be enhanced, and measurement with a higher sensitivity than with the conventional NMR analysis device becomes possible. 2) A sample can be exchanged simply by moving the sample continuously in one direction from the lateral face, and thus measurement efficiency can be improved. 3) By allowing access to the sample space from the axial direction (the magnetic field direction) and the direction perpendicular to the axis, it is easy to irradiate a light to a photoactive sample and observe scattered light and transmitted light. The above described implementations of mode of use are examples of the effect of the present invention. These effects are achieved by accessibility from a horizontal direction (a perpendicular direction to the axial direction). However, when trying to allow access from the horizontal direction, it was difficult to realize uniformity of the magnetic field. According to the present invention, it is possible to realize a wider uniform magnetic field space in addition to enabling access from the horizontal direction.

In addition, as shown in FIG. 6A, the space of the spacer 52 is formed so as to penetrate from a portion of the lateral circumferential portion of the spacer 52 to another portion, and then the magnetic field space can be accessed from two directions. When the spacer 52 is not used, a larger space 52c can be formed and it is easier to access to the space. Consequently, the convenience of the bulk magnet structure 50A is improved.

The shape of the space 52c or the spacer 52 according to this embodiment is appropriately determined, depending on the size of the required work space and the size of the bulk body 51B and the like. As the space to be formed becomes larger, it becomes possible to secure the aforementioned larger working space. However, the contact area between the space 52 c or the spacer 52 and the upper and lower bulk bodies 51c and 51d and the outer circumferential reinforcing rings 53c and 53d contacting the space 52c or the spacer 52 is decreased, whereby the cooling efficiency from the cold head 21 to the bulk magnet structure 50A decreases. Therefore, the shape of the space 52c or the spacer 52 should be determined in view of such a balance.

For example, although the spacer 52 according to this embodiment is formed of the two separated spacer members 52a and 52b as shown in FIG. 6A, such a separated form is not limited to the example shown in FIG. 6A. For example, the spacer 52 may be separated into three or more spacer members. In addition, the spacer 52 may be ring-shaped. Further, it is possible to form a larger space 52c without using the spacer 52.

Figure 6B:
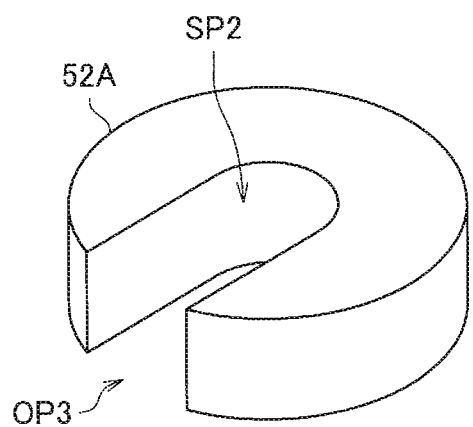
FIG. 6B is a schematic diagram showing a modified example of a spacer according to the same embodiment.

In addition, the spacer 52 may have a form as shown in FIG. 6B. FIG. 6B is a schematic diagram showing a modified example of the spacer 52 according to this embodiment. As shown in FIG. 6B, the spacer 52A may be formed by one member and may have a form having a space SP2 formed from the opening portion OP3 provided on the lateral portion to the inside the magnet structure. The spacer 52A may be arranged so that the space passes through the center axis of the bulk magnet structure 50A in the layered structure of the bulk magnet structure 50A.

In addition, the spacer 52 is preferably formed by a non-superconducting bulk body. From the viewpoint of transfer and absorption of heat generated in the superconducting material, the thermal conductivity of such a non-superconducting bulk body is 20 W/(m·K) or more, in a temperature range of 20K to 70K in which a strong magnetic field can be stably generated by freezer cooling or the like, more preferably 100 W/(m·K) or more. Specifically, the spacer 52 is preferably formed by a metal having a high thermal conductivity and a high electric conductivity, such as copper, copper alloy, aluminum, aluminum alloy, silver, silver alloy or the like.

Incidentally, such a bulk magnet structure 50A shown in FIGS. 5A, 5B and 5C is cooled by a refrigerant or a freezer. For example, the bulk magnet structure 50A may be mounted on the cold head 21 as shown in FIG. 2, and the vacuum insulation container 10 for forming the vacuum insulation layer may be provided around the bulk magnet structure 50A. Alternatively, the bulk magnet structure 50 may be cooled by using a refrigerant (helium gas or the like) after providing the double walled outer wall and a vacuum heat insulation layer between the outer walls. After the external magnetic field is applied at a temperature equal to or higher than the critical temperature of the superconducting body, the bulk magnet structure 50A is cooled to a predetermined cooling temperature at which the bulk magnet structure 50A is brought into a superconducting state, and after reaching the cooling temperature, the applied external magnetic field is lowered. As a result, a superconducting current is induced inside the magnetic structure to magnetize it.

It is usually possible to reproduce the magnetic field distribution of the applied magnetic field in the bulk magnet structure 50A by magnetizing it so that the center of the magnetic field of the applied magnetic field is aligned with the center of the layering direction of the bulk magnet structure 50A. In this case, it is possible to copy a magnetic field distribution almost equal to the applied magnetic field by using a condition in which the cross-section of each bulk body does not become a fully magnetized state as the magnetization condition. Therefore, when a highly uniform high magnetic field is applied according to the above condition, a highly uniform and high strength magnetic field can be reproduced in the bulk magnet structure 50A, and thus it can be applied as a magnet for NMR.

Second Embodiment

Figure 8A:
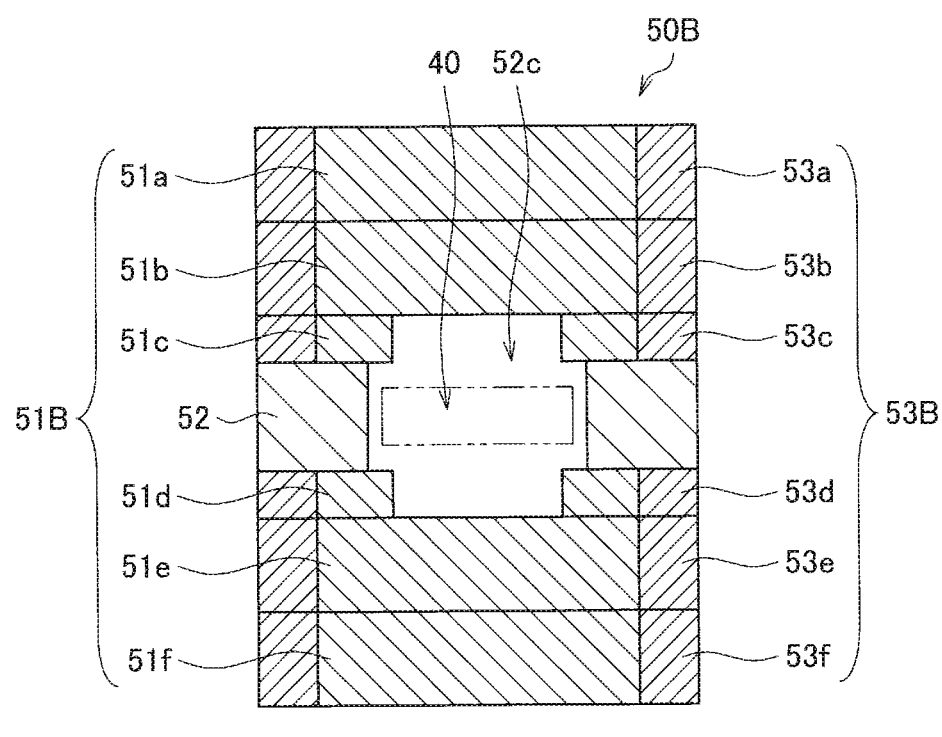
FIG. 8A is a cross-sectional view (viewpoint from a first direction) showing an example of a bulk magnet structure according to a second embodiment of the present invention.
Figure 8B:
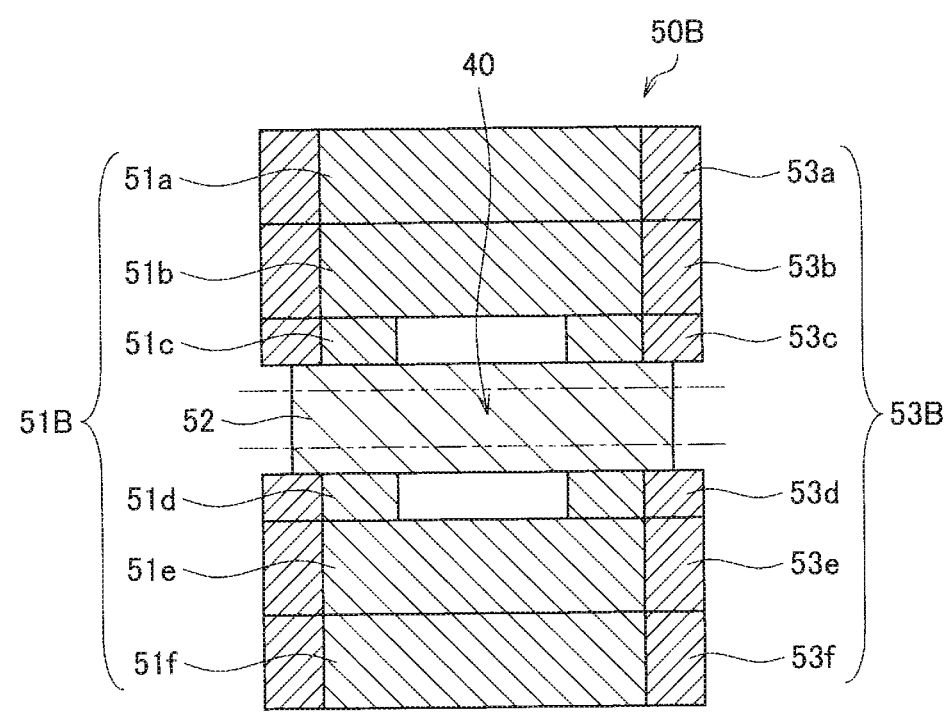
FIG. 8B is a cross-sectional view (viewpoint from a second direction) showing an example of a bulk magnet structure according to the same embodiment.

FIGS. 8A and 8B are cross-sectional views showing an example of a bulk magnet structure 50B according to a second embodiment of the present invention. FIG. 8A is a cross-sectional view as seen from the first direction D1, and FIG. 8B is a cross-sectional view as seen from the second direction D2.

As shown in FIGS. 8A and 8B, the bulk magnet structure 50B according to this embodiment comprises a bulk body portion 51B comprising a plurality of columnar bulk bodies 51a, 51b, 51e and 51f and ring-shaped bulk bodies 51c and 51d, spaces 52c and 40 (which may be formed by spacer 52) between the bulk bodies 51a-51c and the bulk bodies 51d-51f and an outer circumferential ring portion 53B comprising the outer circumferential rings 53a-53f fitted to the outer circumferential surface of each of the bulk bodies 51a-51f. That is, the bulk magnet structure 50B according to this embodiment differs from the bulk magnet structure 50A according to the first embodiment in that bulk bodies disposed directly above and directly under the spaces 40 and 52c or the spacers 52 are the ring-shaped bulk bodies 51c and 51d, respectively. The bulk magnet structure 50B is formed by layering the bulk bodies 51a-51f such that their central axes are aligned to each other. The spacer 52 has a shape shown in FIG. 6A, and it is layered together with the bulk bodies 51a-51f and the outer circumferential reinforcing rings 53a-53f as the bulk magnet structure 50A according to the first embodiment. Incidentally, the upper bulk body portions 51a-51c and the outer circumferential reinforcing rings 53a-53c and the lower bulk body portions 51d-51f and the outer circumferential reinforcing rings 53d-53f may be spaced apart from each other without using the spacer 52. Although this is not shown, a second container 10b similar to that of the first embodiment is prepared and the upper flange is projected in the direction of the central axis so that the upper bulk portions 51a-51c and the outer circumferential reinforcing rings 53a-53c may be supported or the like. In this case, the lower bulk body portions 51d-51f can be cooled in a state of being placed on the cold head 21 of the cooling device 20. The upper bulk body portions 51a-51c may be cooled by using a refrigerant (helium gas or the like) after forming the outer wall in a double structure and providing a vacuum heat insulation layer between the double outer walls.

With such a configuration, as shown in FIGS. 8A and 8B, it is possible to secure a wider space in the central portion of the bulk magnet structure 50B. Specifically, the physical space 52c provided in the central portion of the bulk magnet structure 50B further extends to the space inside the ring-shaped bulk bodies 51c and 51d. Therefore, a wider working space can be secured.

Incidentally, while in the examples shown in FIGS. 8A and 8B, one ring-shaped bulk body 51c and one ring-shaped bulk body 51d are respectively provided on the upper portion and the lower portion of the spacer 52, the present invention is not limited to this example. For example, a plurality of ring-shaped bulk bodies may be sequentially layered on at least one of the top and bottom of the spacer 52. Further, the ring-shaped bulk body may be arranged only on one of the upper portion and the lower portion of the space 52c or the spacer 52. In addition, the number of layers of the bulk bodies shown in FIGS. 8A and 8B is an example, and the number thereof is not particularly limited.

Third Embodiment

In addition, when a strong magnetic field is generated in the bulk magnet structure by magnetization of a strong magnetic field, a large electromagnetic force acts on both of the ring-shaped bulk body and the columnar bulk body. As a result, a ring-shaped bulk body and a columnar bulk may lead to a problem of cracking. In this case, in the bulk magnet structure in which a plurality of bulk magnets are layered, the greatest stress can act on the vicinity of the center or the inner circumferential surface of both the end surfaces in the layering direction of the bulk magnets arranged at the ends, and thus breakage is most likely to occur in this portion. Therefore, the superconducting bulk bodies at the both ends in the layering direction on which the highest stress acts as described above are constituted by a stack in which an oxide superconducting bulk body having a low thickness in the axial direction and a plane reinforcing member are alternately layered. It may be disposed at the end of the bulk magnet structure.

Figure 9A:
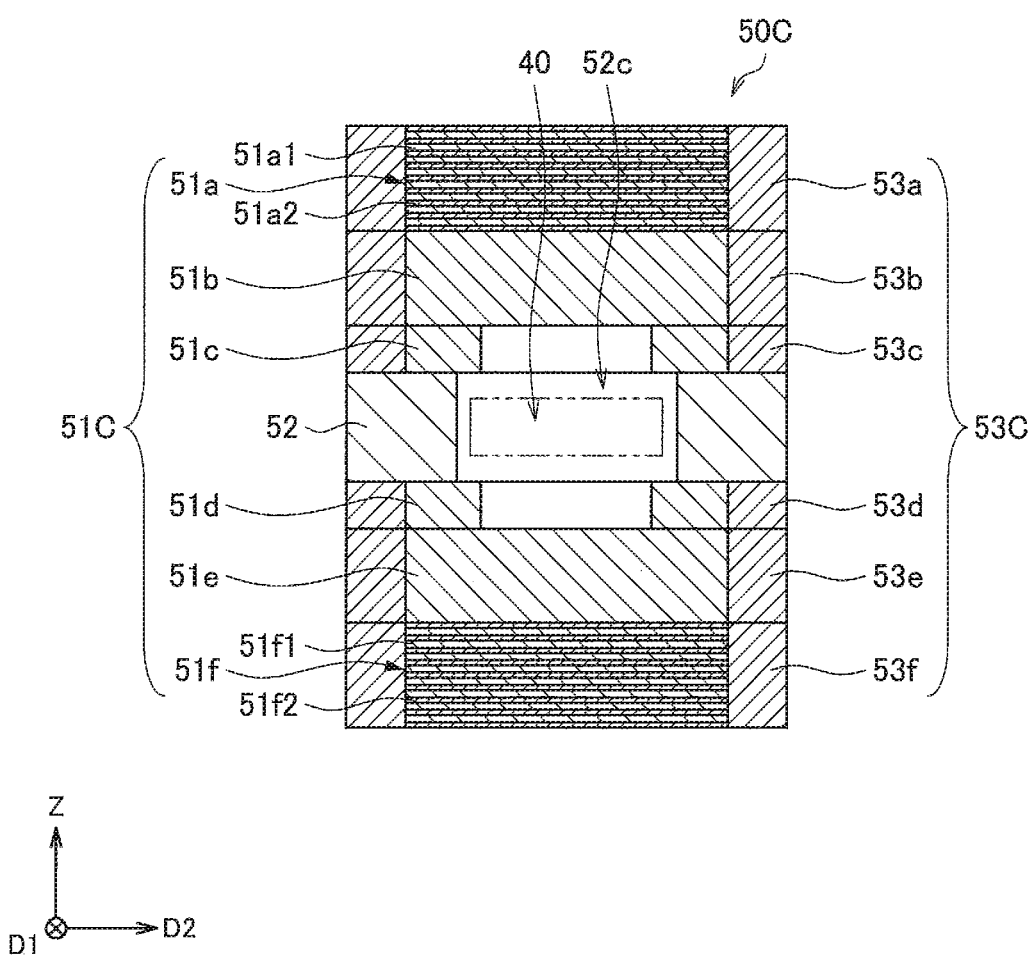
FIG. 9A is a cross-sectional view (viewpoint from a first direction) showing an example of a bulk magnet structure according to a third embodiment of the present invention.
Figure 9B:
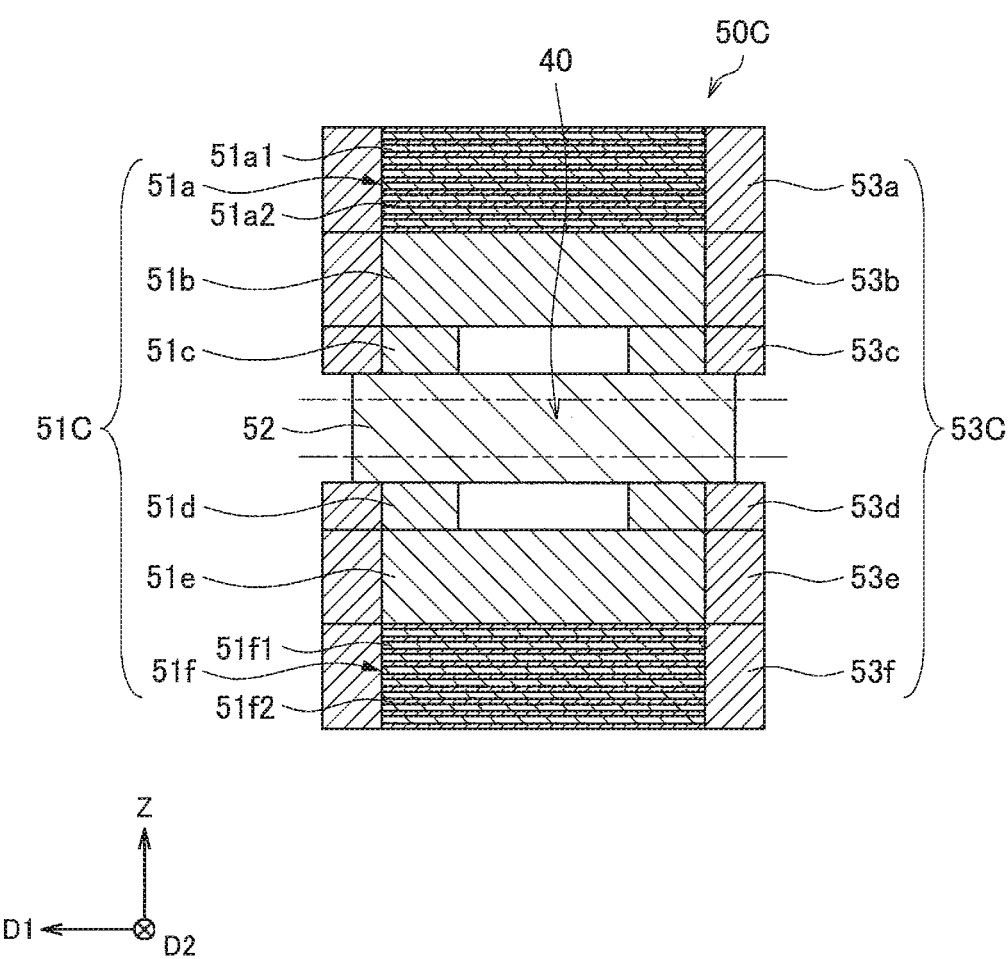
FIG. 9B is a cross-sectional view (viewpoint from a second direction) showing an example of a bulk magnet structure according to the same embodiment.

FIGS. 9A and 9B are cross-sectional views showing an example of a bulk magnet structure 50C according to a third embodiment of the present invention. FIG. 9A is a cross-sectional view as seen from the first direction D1, and FIG. 9B is a cross-sectional view as seen from the second direction D2.

As shown in FIGS. 9A and 9B, the bulk magnet structure 50C according to this embodiment comprises a bulk body portion 51C comprising columnar stacks 51a and 51f, columnar bulk bodies 51b and 51e, and ring-shaped bulk bodies 51c and 51d, a space 52c, 40 (which may be formed by the spacer 52) between the bulk bodies 51a-51c and the bulk bodies 51d-51f and an outer circumferential reinforcing ring portion 53C comprising outer circumferential reinforcing rings 53a-53f fitted to the outer circumferential surfaces of the respective bulk bodies 51a-51f. That is, the bulk magnet structure 50C according to this embodiment differs from the bulk magnet structure 50B according to the second embodiment, in that the columnar bulk bodies arranged at the end portions of the bulk magnet structure 50C is the columnar stacks 51a and 51f. The bulk magnet structure 50C is formed by layering the bulk bodies 51a-51f such that their central axes are aligned to each other. The spacer 52 has a shape shown in FIG. 6A, and it is layered together with the bulk bodies 51a-51f and the outer circumferential reinforcing rings 53a-53f like the bulk magnet structure 50B according to the second embodiment. Incidentally, the upper bulk body portions 51a-51c and the outer circumferential reinforcing rings 53a-53c and the lower bulk body portions 51d-51f and the outer circumferential reinforcing rings 53d-53f may be spaced apart from each other without using the spacer 52. Although this is not shown, a second container 10b similar to that of the first embodiment is prepared and the upper flange is projected in the direction of the central axis so that the upper bulk body portions 51a-51c and the outer circumferential reinforcing rings 53a-53c may be supported or the like. In this case, the lower bulk body portions 51d-51f can be cooled in a state of being placed on the cold head 21 of the cooling device 20. The upper bulk body portions 51a-51c may be cooled by using a refrigerant (helium gas or the like) after forming the outer wall in a double structure and providing a vacuum heat insulation layer between the double outer walls.

The columnar stack 51a (51f) is formed by alternately layering columnar oxide superconducting bulk bodies 51a1 (51f1) having a small thickness in the axial direction and planar reinforcing plates 51a2 (51f2). By disposing the columnar stacks 51a and 51f at the end portions of the bulk magnet structure 50C, it is possible to maintain sufficient mechanical strength in the vicinity of both end surfaces in the layering direction on which a large stress can act. In addition, when columnar bulk bodies other than at both ends in the layering direction are also provided in order to obtain a higher mechanical strength, it is preferable to use a columnar stack in which a columnar oxide superconducting bulk body having a low thickness in the axial direction and the planar reinforcing plate are alternately layered. The number of layering of columnar bulk bodies and planar reinforcing plates constituting the columnar stack shown in FIGS. 9A and 9B is an example, and the number thereof is not particularly limited.

Fourth Embodiment

Figure 10A:
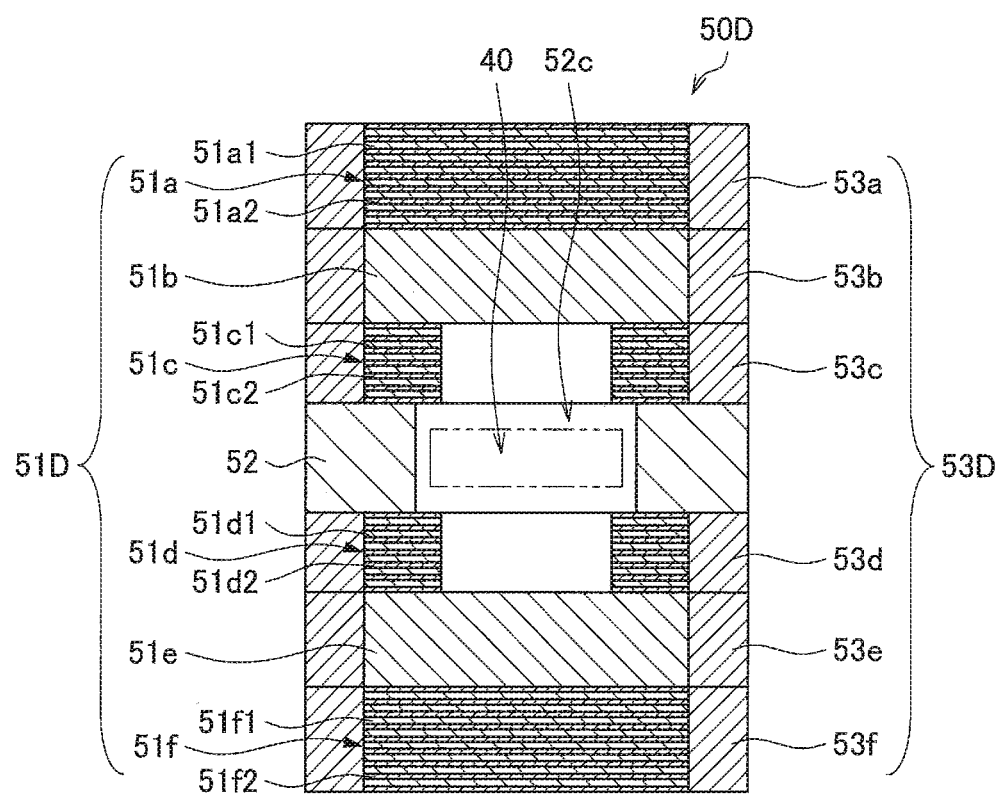
FIG. 10A is a cross-sectional view (viewpoint from a first direction) showing an example of a bulk magnet structure according to a fourth embodiment of the present invention.
Figure 10B:
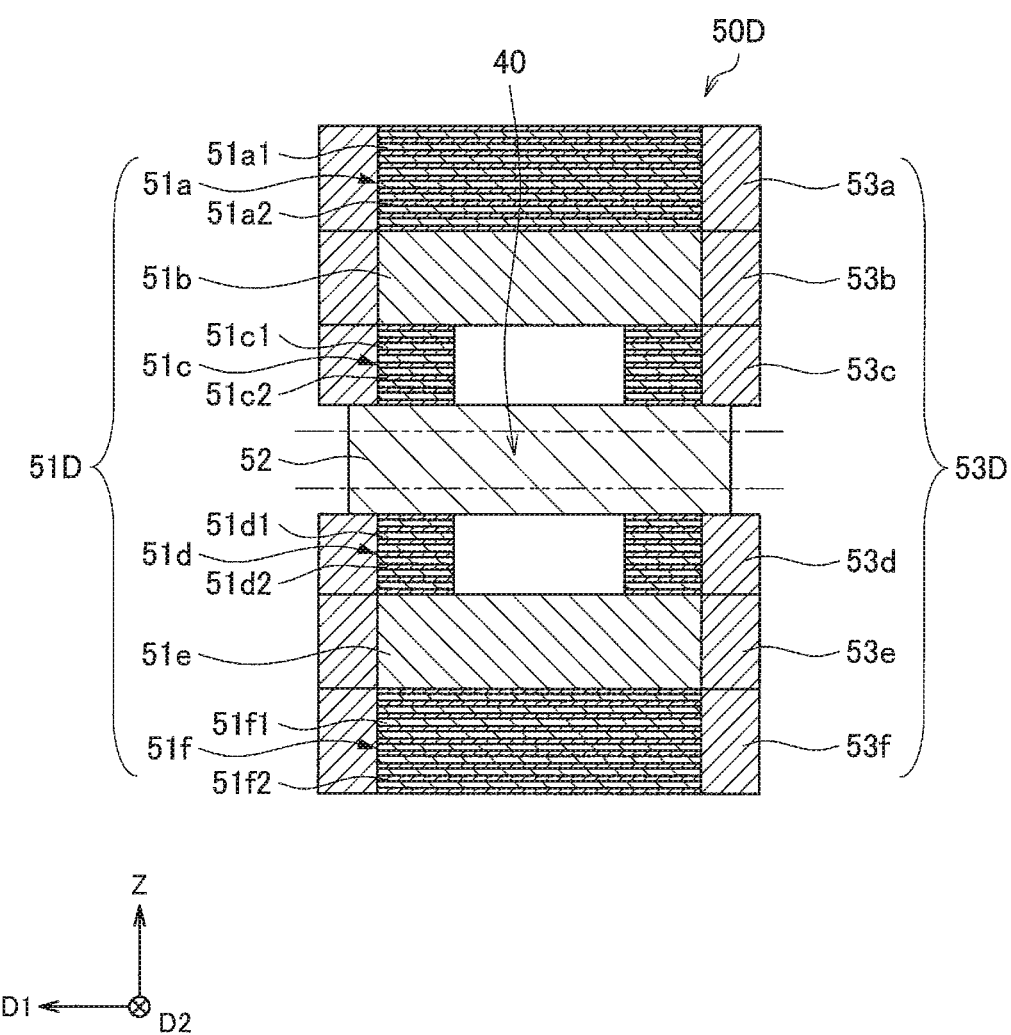
FIG. 10B is a cross-sectional view (viewpoint from a second direction) showing an example of a bulk magnet structure according to the same embodiment.

FIGS. 10A and 10B are cross-sectional views showing an example of a bulk magnet structure 50D according to a fourth embodiment of the present invention. FIG. 10A is a cross-sectional view as seen from the first direction D1, and FIG. 10B is a cross-sectional view as seen from the second direction D2.

As shown in FIG. 10A and FIG. 10B, the bulk magnet structure 50D according to this embodiment comprises a bulk body portion 51D comprising columnar stacks 51a and 51f, columnar bulk bodies 51b and 51e and ring-shaped stacks 51c and 51d, a space 52c, 40 (which may be formed by the spacer 52) between the bulk bodies 51a-51c and the bulk bodies 51d-51f, and an outer circumferential reinforcing ring portion 53D comprising outer circumferential reinforcing rings 53a-53f fitted to the outer circumferential surfaces of the respective bulk bodies 51a-51f. That is, the bulk magnet structure 50D according to this embodiment differs from the bulk magnet structure 50C according to the third embodiment in that the ring-shaped bulk bodies disposed directly above and below the spacer 52 are ring-shaped stacks 51c and 51d. The bulk magnet structure 50D is formed by layering the bulk bodies 51a-51f such that their central axes are aligned with each other. The spacer 52 has a shape shown in FIG. 6A, and it is layered together with the bulk bodies 51a-51f and the outer circumferential reinforcing rings 53a-53f like the bulk magnet structure 50C according to the third embodiment. Incidentally, the upper bulk body portions 51a-51c and the outer circumferential reinforcing rings 53a-53c and the lower bulk body portions 51d-51f and the outer circumferential reinforcing rings 53d-53f may be spaced apart from each other without using the spacer 52. Although this is not shown, a second container 10b similar to that of the first embodiment is prepared and the upper flange is projected in the direction of the central axis so that the upper bulk portions 51a-51c and the outer circumferential reinforcing rings 53a-53c may be supported or the like. In this case, the lower bulk body portions 51d-51f can be cooled in a state of being placed on the cold head 21 of the cooling device 20. The upper bulk body portions 51a-51c may be cooled by using a refrigerant (helium gas or the like) after forming the outer wall in a double structure and providing a vacuum heat insulation layer between the double outer walls.

Directly above and below the space 52c or the spacer 52 is a position corresponding to the end portions of the bulk body layered on the upper side or the lower side of the space 52c or the spacer 52. Therefore, a large electromagnetic force acts also on the bulk body directly above and below the space 52c or the spacer 52, and as a result, there is a problem that the bulk body may become cracked. Therefore, the bulk body directly above and below the space 52c or the spacer 52 on which such the highest stress acts may be formed by a stack in which an oxide superconducting bulk body having a low thickness in the axial direction and a planar reinforcing member are alternately layered.

The ring-shaped stack 51c (51d) is configured by alternately layering a ring-shaped oxide superconducting bulk body 51c1 (51d1) having a small thickness in the axial direction and a planar reinforcing ring 51c2 (51d2). By arranging the ring-shaped stacks 51c, 51d directly above and below the space 52c or the spacer 52, it becomes possible to maintain sufficient mechanical strength in the vicinity of the contact surface with the space 52c or the spacer 52 where high stress can act. In the case where a ring-shaped bulk body is also disposed other than those directly above and below the space 52c or the spacer 52 in order to obtain even higher mechanical strength, it is preferable to use a ring-shaped stack in which a ring-shaped oxide superconducting bulk body and a planar reinforcing ring are alternately layered. In addition, the number of layered ring-shaped bulk bodies and planar reinforcing rings constituting the ring-shaped stack shown in FIGS. 10A and 10B is an example, and the number thereof is not particularly limited.

Fifth Embodiment

In the above embodiment, the following configuration may be further added within a range that does not cause inconvenience.

Figure 11:
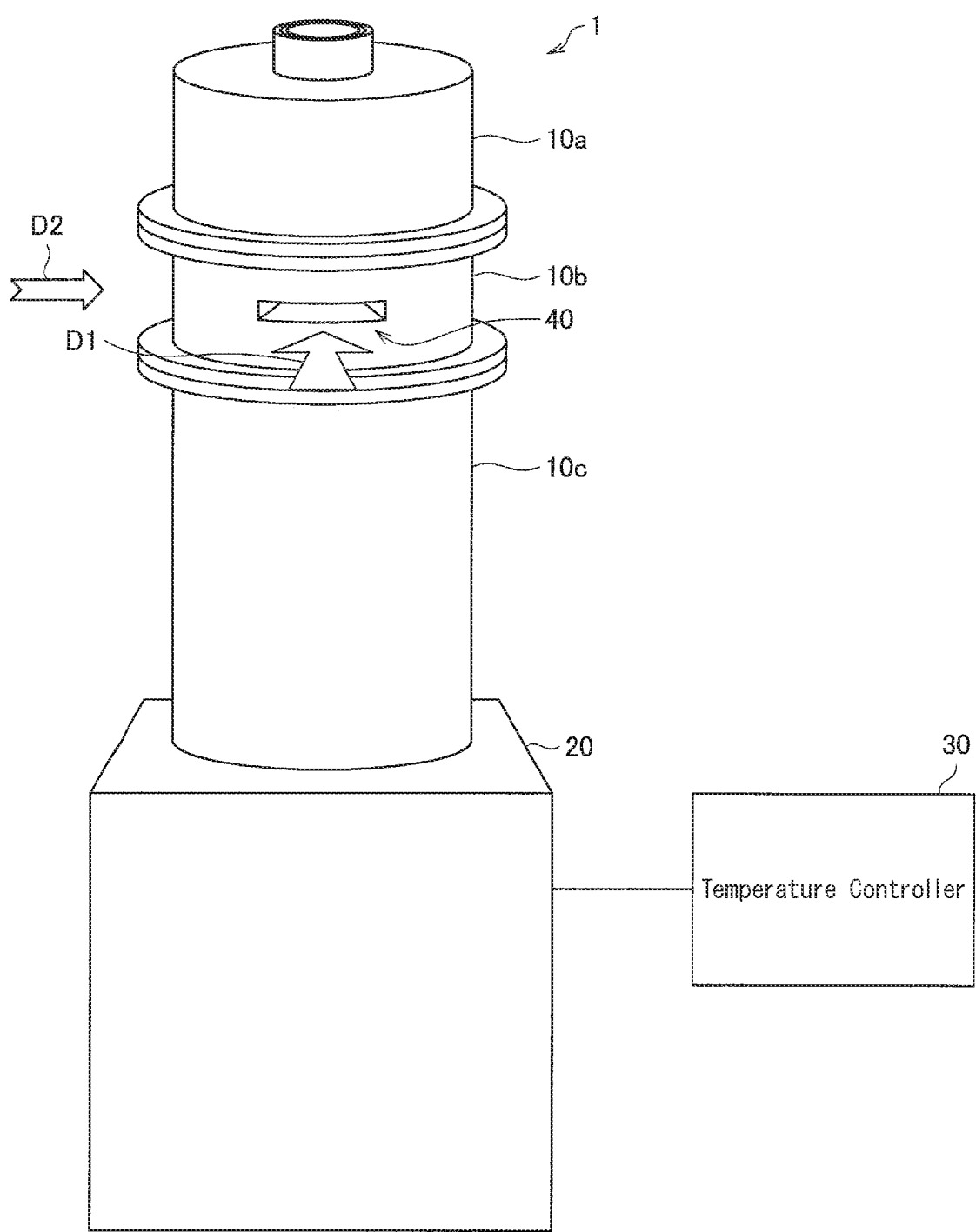
FIG. 11 is a schematic view showing an appearance of a bulk magnet system for NMR according to a fifth embodiment of the present invention.
Figure 12:
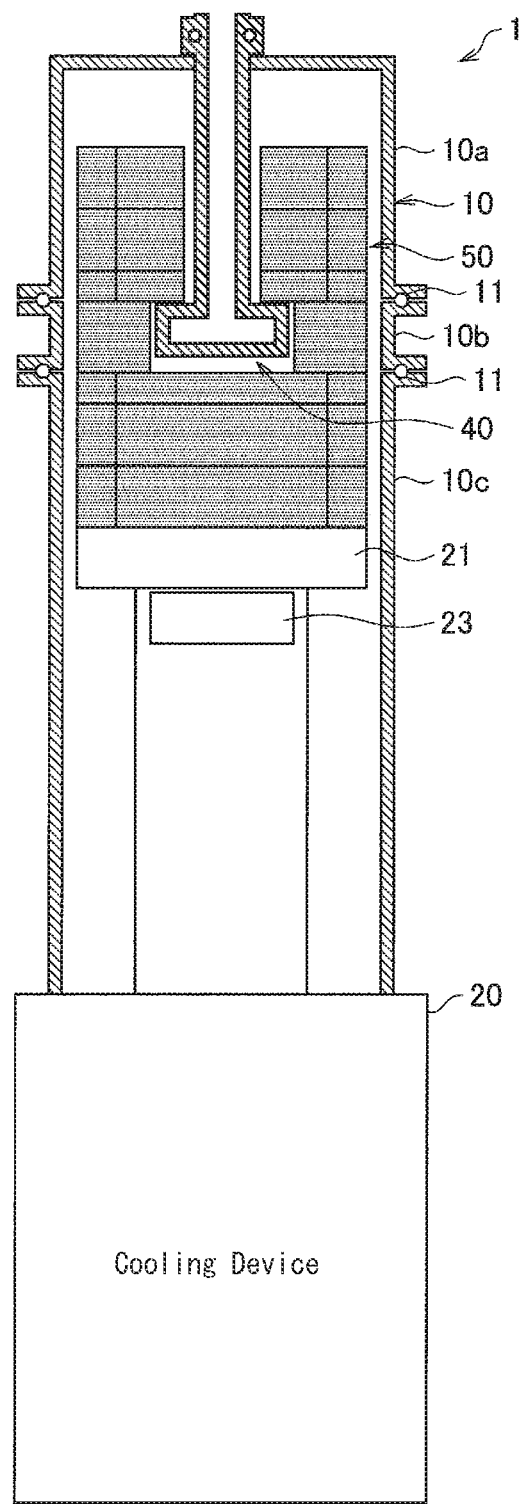
FIG. 12 is an explanatory view showing a schematic configuration of a bulk magnet system for NMR according to a fifth embodiment of the present invention.
Figure 13:
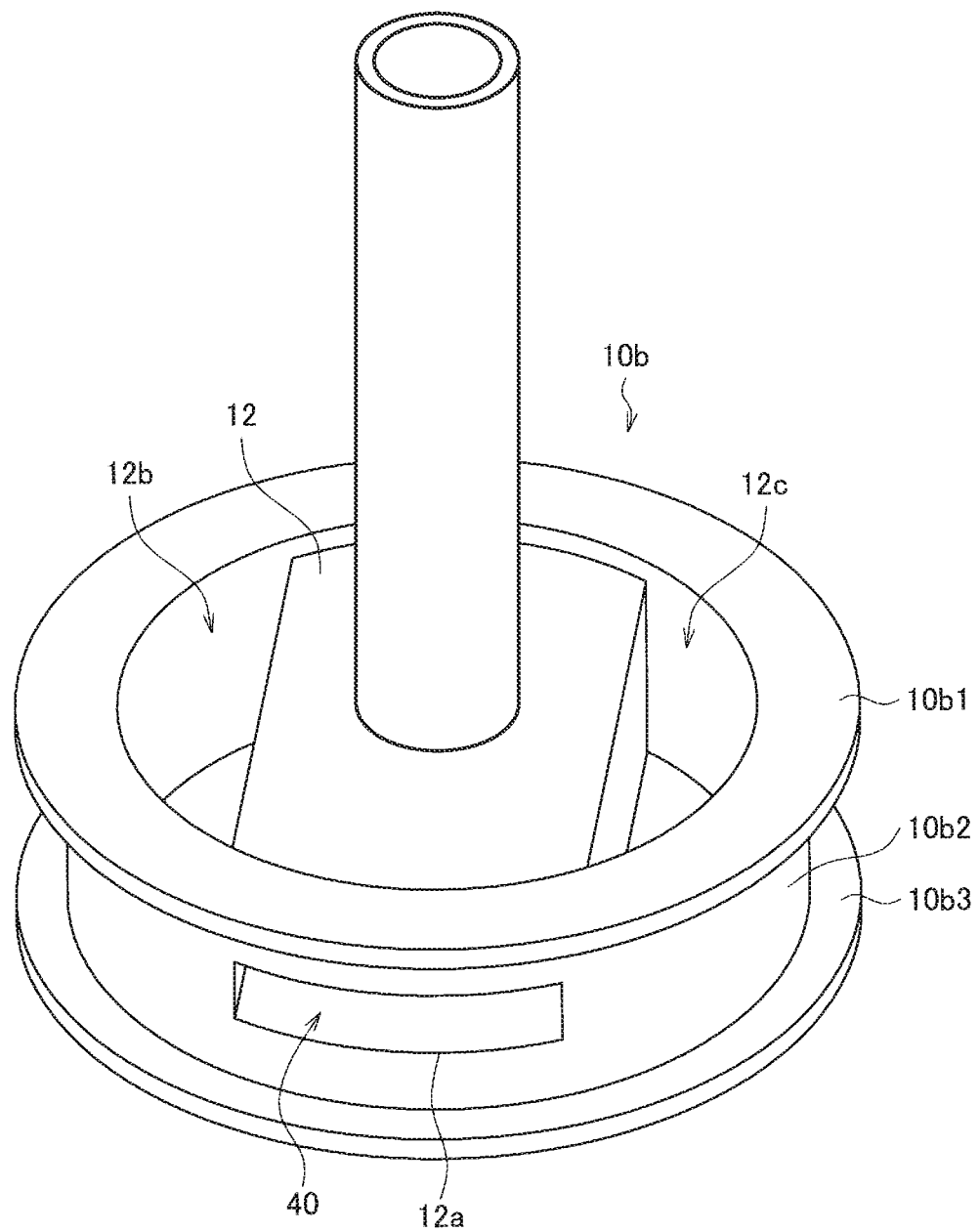
FIG. 13 is a schematic view showing an example of a second container according to a fifth embodiment of the present invention.

A ring-shaped bulk body Ma is arranged at one end of the bulk body of the bulk magnet structure 50 in the axial direction (synonymous with the layering direction), and ring-shaped bulk bodies 51*a*-51*c* may be sequentially layered. Inside the ring-shaped bulk bodies 51*a*-51*c*, a space communicating with the external space may be formed. On the other hand, columnar bulk bodies 51*e* and 51*f* may be layered and disposed at the other end of the axial direction of the bulk body of the bulk magnet structure 50. FIG. 11, FIG. 12 and FIG. 13 are respectively a schematic view showing an appearance of a bulk magnet system for NMR according to this embodiment, an explanatory view showing a schematic configuration of the bulk magnet system for NMR according to the same embodiment, and a schematic view showing an example of a second container according to the same embodiment.

By using not only a ring-shaped bulk body but also a columnar bulk body as the bulk body constituting the bulk magnet structure 50, the following advantages can be obtained as compared with the configuration using only the ring-shaped bulk body. That is, by using a columnar bulk body, it is not necessary to perform drilling like a ring-shaped bulk body, so the bulk magnet structure 50 can be produced at low cost. In addition, since the columnar bulk body does not have an inner circumferential surface that can be a starting point of cracking due to electromagnetic stress, breakage due to cracking is unlikely to occur.

At least one ring-shaped bulk body may be disposed on one axial end of the bulk magnet structure 50. With this configuration, it is possible to insert a sample or the like into the magnetic field space formed inside the ring-shaped bulk body from the Z axis direction (layering axial direction). By providing a probe or the like including a magnetic field correction coil, a signal detection coil and an electromagnetic wave irradiation coil, etc. in such a magnetic field space, it is possible to detect an NMR signal for a sample or the like. That is, it can be applied as a magnet for NMR.

In addition, a plurality of ring-shaped bulk bodies may be sequentially layered from one axial end to the central portion of the bulk magnet structure 50. With such a configuration, it is possible to utilize the space in the central portion of the bulk magnet structure 50 where a uniform magnetic field space is likely to be formed. For example, when applying such a bulk magnet structure 50 as a magnet for NMR, it is possible to place a sample or the like in a uniform magnetic field space.

At least one columnar bulk body may be disposed on the other axial end of the bulk magnet structure 50. With such a configuration, it is possible to increase resistance to cracking due to magnetic field stress that may be applied more strongly to the end portion of the bulk magnet structure 50. Therefore, breakage of the bulk magnet structure 50 can be prevented.

<Configuration Example of Stack>

Hereinafter, a specific configuration example of the ring-shaped stack in which a ring-shaped oxide superconducting bulk body having a small thickness in the axial direction and a planar reinforcing ring are alternately arranged as any one of the ring-shaped stacks 51*c* and 51*d* and the bulk bodies 51*b*-51*f* constituting the bulk magnet structure 50D according to the fourth embodiment shown in FIGS. 10A and 10B will be described with reference to FIGS. 14 to 21D.

First Configuration Example

Figure 14:
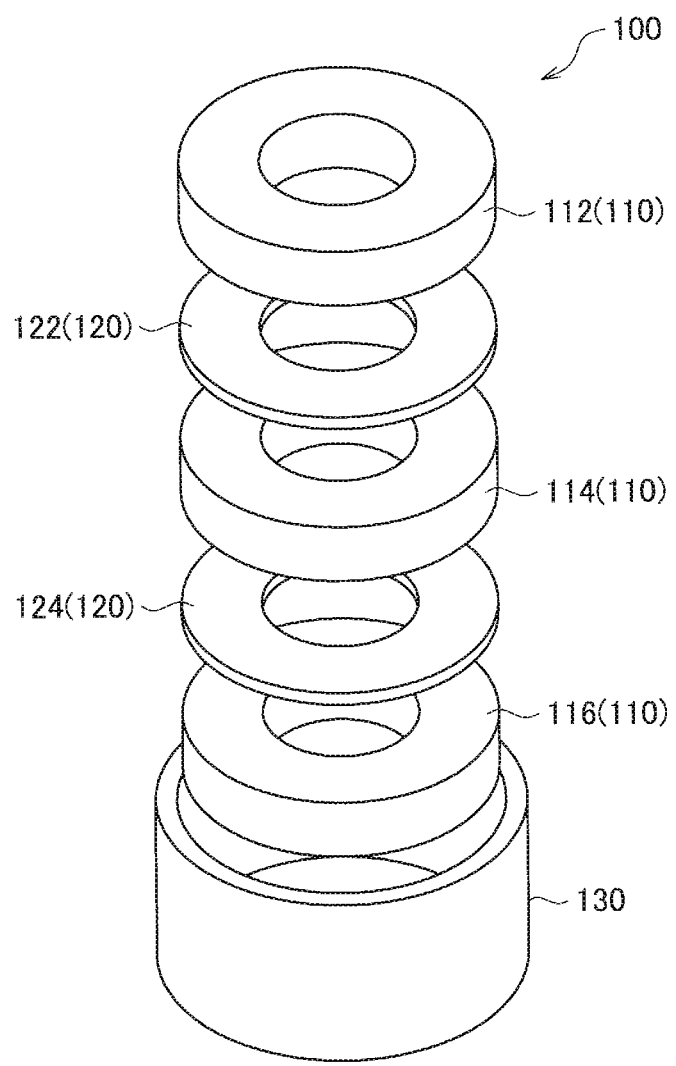
FIG. 14 is a schematic exploded perspective view showing a bulk magnet formed by a ring-shaped stack according to a first configuration example of a ring-shaped stack.

First, a first configuration example of a ring-shaped stack will be described with reference to FIG. 14. FIG. 14 is a schematic exploded perspective view showing a bulk magnet 100 constituted by the ring-shaped stack according to the first configuration example.

The bulk magnet 100 according to this configuration example comprises a ring-shaped bulk body 110 having a through-hole at the center of a circular plate, a planar reinforcing ring 120 having a through-hole at the center of a circular plate, and an outer circumferential reinforcing ring 130. In this embodiment, three ring-shaped bulk bodies 112, 114 and 116 are provided as the ring-shaped bulk body 110, and two planar reinforcing rings 122 and 124 are provided as the planar reinforcing ring 120. The ring-shaped bulk body 110 and the planar reinforcing ring 120 are alternately layered in the central axial direction of the ring of the bulk magnet. For example, the planar reinforcing ring 122 is disposed between the oxide superconducting bulk bodies 112 and 114, and the planar reinforcing ring 124 is disposed between the ring-shaped bulk bodies 114 and 116. The layered ring-shaped bulk body 110 and the planar reinforcing ring 120 are bonded or adhered, and to their outer circumferential surface, the outer circumferential reinforcing ring 130 made of a hollowed metal is fitted. Thus, a bulk magnet having a central through-hole is formed.

Bonding or adhesion between the ring-shaped bulk body 110 and the planar reinforcing ring 120 layered to each other in the central axial direction may be performed by, for example, resin or grease, more preferably by soldering for obtaining stronger bonding force. In the case of soldering, it is desirable to form an Ag thin film on the surface of the ring-shaped bulk body 110 by sputtering or the like, followed by annealing at 100° C. to 500° C. As a result, the Ag thin film and the surface of the ring-shaped bulk body are strongly matched. Since the solder itself has a function of improving thermal conductivity, soldering treatment is also desirable from the viewpoint of improving thermal conductivity and equalizing the temperature of the bulk magnet as a whole.

At this time, as a method of reinforcing against electromagnetic stress, the planar reinforcing ring 120 is preferably a metal such as a solderable aluminum alloy, Ni-based alloy, nichrome or stainless steel. Furthermore, nichrome is further desirable, since it has a linear expansion coefficient relatively close to that of the ring-shaped bulk body 110 and causes slight compression stress to act on the ring-shaped bulk body 110 upon cooling from room temperature. On the other hand, from the viewpoint of prevention of breakage by quenching, it is preferable to use a metal such as copper, copper alloy, aluminum, aluminum alloy, silver, silver alloy or the like having high thermal conductivity and high electric conductivity as the planar reinforcing ring 120. Incidentally, these metals are solderable. Further, oxygen-free copper, aluminum and silver are preferable from the viewpoint of thermal conductivity and electric conductivity. In addition, it is effective to use the planar reinforcing ring 120 having pores in order to restrain bubble entrainment and so on and permeate the solder uniformly when being bonded with solder or the like.

By the reinforcement by the planar reinforcing ring 120 made of such a high strength metal, due to the thermal conductivity as a whole, thermal stability as a bulk magnet is increased and quenching is less likely to occur, and high field magnetization in a lower temperature region, that is, in the high critical current density Jc region becomes possible. Since metals such as copper, aluminum and silver have high electrical conductivity, it is expected that, when a cradle causing local degradation of superconducting properties occurs, it can be expected to detour the superconducting current and have a quench suppressing effect. In this case, in order to enhance the quench suppressing effect, it is desirable that the contact resistance at the interface between the ring-shaped bulk body and the high electrically conductive planar reinforcing ring be small, and it is desirable to bond them with solder, etc., after forming a silver film on the surface of the ring-shaped bulk body.

In the practical design of a bulk magnet, since the proportion of the superconducting material decreases by the insertion of the planar reinforcing ring 120 made of a high strength metal, the proportion of the planar reinforcing ring 120 may be determined according to the intended use condition. From the above viewpoint, it is preferable that the planar reinforcing ring 120 be formed by combining a plurality of metals selected from a high strength metal having high strength and a high strength metal having high thermal conductivity and determining their ratio.

Further, a normal temperature tensile strength of the ring-shaped bulk body 110 is about 60 MPa, and a normal temperature tensile strength of the solder for attaching the planar reinforcing ring 120 to the ring-shaped bulk body 110 is usually less than 80 MPa. Accordingly, the planar reinforcing ring 120 having a normal temperature tensile strength of 80 MPa or more is effective as a reinforcing member. Therefore, the planar reinforcing ring 120 preferably has a normal temperature tensile strength of 80 MPa or more.

Further, from the viewpoint of transfer and absorption of heat generated in the superconducting material, the thermal conductivity of the high strength metal having a high thermal conductivity is preferably 20 W/(m·K) or more, and more preferably 100 W/(m·K) or more in the temperature range of 20 K to 70 K. In the case where a plurality of types of planar reinforcing rings are disposed between the ring-shaped bulk bodies 110 as the planar reinforcing ring 120, at least one of the planar reinforcing rings has a thermal conductivity of 20 W/(m·K) or more.

Also, the outer circumferential reinforcing ring 130 may be made of a material having a high thermal conductivity in order to enhance the quench suppressing effect. In this case, for example, a material containing a metal such as copper, aluminum, silver or the like having a high thermal conductivity as a main component can be used for the outer circumferential reinforcing ring 130. From the viewpoint of transfer and absorption of heat generated in the superconducting material, the thermal conductivity of the circumferential reinforcing ring 130 having a high thermal conductivity is preferably 20 W/(m·K) or more, and more preferably 100 W/(m·K) or more in the temperature range of 20 K to 70 K by which a strong magnetic field can be stably generated by a freezer cooling or the like.

In addition, the outer circumferential reinforcing ring 130 may be formed by concentrically arranging a plurality of rings. That is, one circumferential reinforcing ring is constituted as a whole in such a manner that the circumferential surfaces of the opposing rings are brought into contact with each other. In this case, it is sufficient that at least one of the rings constituting the outer circumferential reinforcing ring has a thermal conductivity of 20 W/(m·K) or more.

The processing of the planar reinforcing ring 120 and the outer circumferential reinforcing ring 130 is performed by a general machining method. The central axes of the inner and outer circumferences of each ring-shaped bulk body 110 are necessary for improving the strength of generated magnetic field and for improving uniformity (or symmetry) of the magnetic field. In addition, the diameter of the outer circumference and the diameter of the inner circumference of each ring-shaped bulk body 110 are design matters, and do not necessarily have to be matched. For example, in the case of a bulk magnet for NMR or MRI, it may be necessary to arrange a shim coil or the like for enhancing magnetic field uniformity in the vicinity of the center. In doing so, it is preferable to make the inner diameter greater near the center, which makes it easier to place the shim coil or the like. Regarding the diameter of the outer circumference, it is preferable to change the diameter of the outer circumferential portion to adjust the target magnetic field strength and its uniformity in order to increase the strength of the magnetic field at the center portion and to improve the uniformity of the magnetic field.

The shape (outer circumference and inner circumference) of the outer circumferential reinforcing ring 130 may be one such that the outer circumferential surface of the ring-shaped bulk body 110 is in close contact with the inner circumferential surface of the outer circumferential reinforcing ring 130. Although FIG. 14 shows an example of a bulk magnet comprising three ring-shaped bulk bodies, the gist of the present invention is that a ring-shaped bulk body having a relatively low strength and a planar reinforcing ring having a high strength are combined to make the resulting composite material have a high strength. Therefore, when the number of layers is increased, the composite effect is exhibited. The thickness of the ring-shaped bulk body is desirably 10 mm or less, more desirably 6 mm or less, and 0.3 mm or more, although it also depends on the diameter (outer diameter). The thickness of the bulk magnet 100 disposed at the end portion in the bulk magnet structure is about 30 mm or less, and when the thickness of the ring-shaped bulk body is 0.3 mm or less, deterioration of superconductivity occurs due to fluctuation in crystallinity of the oxide superconducting body. In addition, since the thickness of the bulk magnet 100 disposed at the end portion in the bulk magnet structure is about 30 mm or less, the thickness of the ring-shaped bulk body to be used is desirably 10 mm or less, the number of the ring-shaped bulk bodies is desirably three or more, and more desirably five or more.

In addition, the planar reinforcing ring adjusts the ratio of the planar reinforcing ring to the ring-shaped bulk body in the bulk magnet including the planar reinforcing ring to adjust the strength of the bulk magnet. For this reason, the thickness of the planar reinforcing ring may be adjusted according to the required strength of the bulk magnet, and is desirably 2 mm or less, and more desirably 1 mm or less.

The first configuration example of the ring-shaped stack according to this embodiment has been described above. According to this configuration example, the planar reinforcing ring 120 is disposed at least between the layered ring-shaped bulk bodies 110. In particular, by alternately layering the ring-shaped bulk body 110 having a relatively low strength against the tensile stress and the planar reinforcing ring 120 to obtain a composite material, it is possible to increase the strength of the material. Furthermore, by using a material having a high thermal conductivity for the planar reinforcing ring 120 and the outer circumferential reinforcing ring 130, occurrence of quenching can also be suppressed. As a result, breakage of the ring-shaped bulk body 110 can be prevented even under a high magnetic field strength condition, and a sufficient total magnetic flux amount can be obtained inside the bulk magnet, and a bulk magnet structure having an excellent magnetic field uniformity can be provided.

Second Configuration Example

Figure 15A:
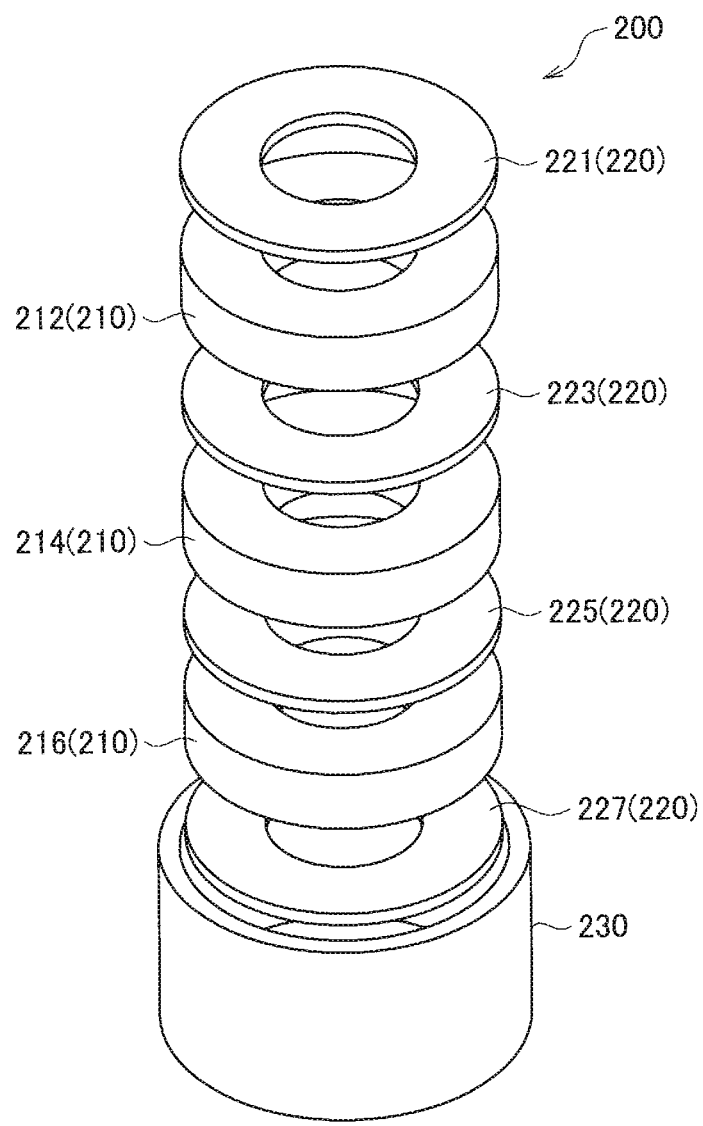
FIG. 15A is a schematic exploded perspective view showing a bulk magnet formed by a ring-shaped stack according to a second configuration example of a ring-shaped stack.
Figure 15B:
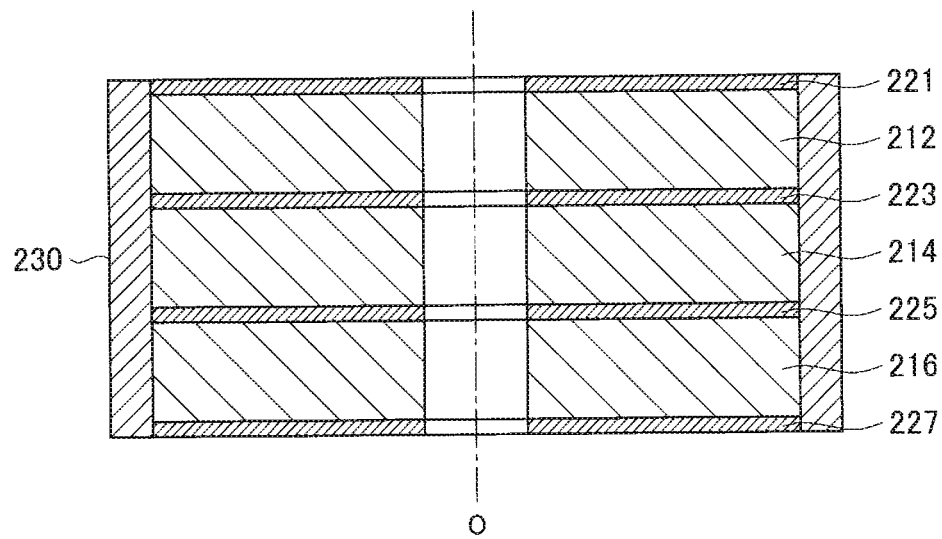
FIG. 15B shows a partial cross-sectional view of the bulk magnet shown in FIG. 15A.
Figure 15C:
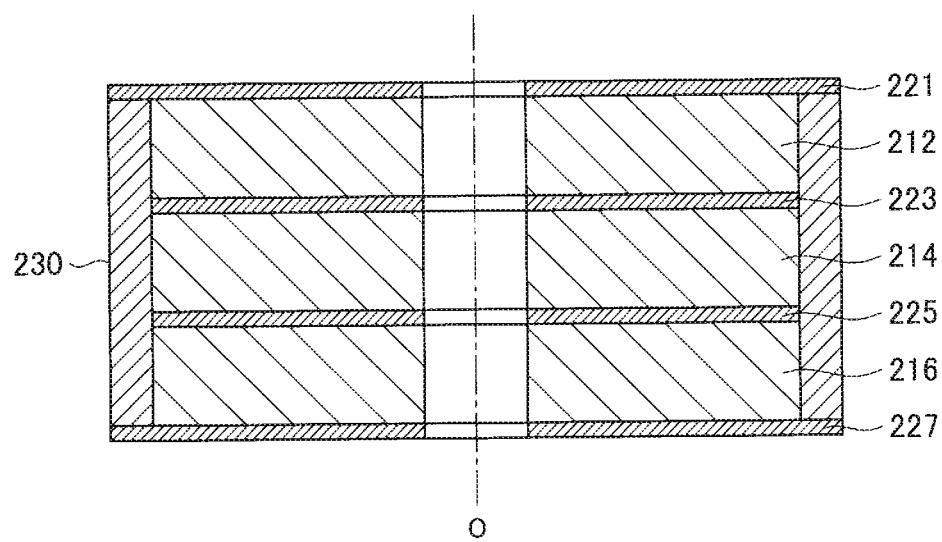
FIG. 15C shows a partial cross-sectional view of a modified example of the bulk magnet according to the same configuration example, taken along the center axis of the bulk magnet.

Next, the second configuration example of the ring-shaped stack of this embodiment will be described, with reference to FIGS. 15A to 15C. FIG. 15A is a schematic exploded perspective view showing a bulk magnet 200 formed by the ring-shaped stack according to this configuration example. FIG. 15B shows a partial cross-sectional view of the bulk magnet 200 shown in FIG. 15A. FIG. 15C shows a partial cross-sectional view of a modified example of the magnet according to this configuration example, taken along the center axis of the bulk magnet 200.

The ring-shaped stack according to this configuration example differs from the stack according to the first configuration example in that the planar reinforcing ring 220 is provided at the end in the central axial direction. As shown in FIG. 15A, the bulk magnet 200 comprises a ring-shaped bulk body 210, a planar reinforcing ring 220 and an outer circumferential reinforcing ring 230. In this configuration example, three ring-shaped bulk bodies 212, 214 and 216 are provided as the ring-shaped bulk body 210, and four planar reinforcing rings 221, 223, 225 and 227 are provided as the planar reinforcing ring 220. The ring-shaped bulk body 210 and the planar reinforcing ring 220 are alternately layered in the central axial direction of the rings. For example, as shown in FIG. 15A, the planar reinforcing ring 223 is disposed between the ring-shaped bulk bodies 212 and 214, and the planar reinforcing ring 225 is disposed between the ring-shaped bulk bodies 214 and 216.

Further, the ring-shaped bulk body 212 is provided with a planar reinforcing ring 221 on a surface opposite to the side on which the planar reinforcing ring 223 is disposed. Similarly, the ring-shaped bulk body 216 is provided with a planar reinforcing ring 227 on a surface opposite to the side on which the planar reinforcing ring 225 is disposed. In this case, as shown in FIG. 15B, the positional relationship of the planar reinforcing ring 221 at the very end portion and the planar reinforcing ring 227 at the other very end portion with the outer circumferential ring 230 is such that the planar reinforcing rings 221 and 227 may be accommodated in the outer circumferential reinforcing ring 230. Alternatively, as shown in FIG. 15C, the outer diameters of the planar reinforcing rings 221 and 227 are substantially equal to the outer diameter of the outer circumferential reinforcing ring 230 so that the edge faces of the outer circumferential reinforcing ring 230 can be covered with the planar reinforcing rings 221 and 227.

The layered ring-shaped bulk body 210 and the planar reinforcing ring 220 are bonded or adhered, and to their outer circumferential surface, an outer circumferential reinforcing ring 230 made of a hollowed metal is fitted. Thus, a bulk magnet having a central through-hole is formed. Incidentally, bonding or adhesion between the ring-shaped bulk body 210 and the planar reinforcing ring 220 layered to each other in the central axial direction may be carried out in the same manner as in the case of the stack according to the first configuration example.

In FIGS. 15A to 15C, an example wherein the planar reinforcing rings 221 and 227 are provided at both ends in the central axial direction of the bulk magnet 200 was shown, but the planar reinforcing rings 221 and 227 are not necessarily disposed at both ends. For example, by disposing a bulk magnet in which the high strength reinforcing member 227 is disposed only on the lowermost surface of FIG. 15A under the bulk magnet in which the planar reinforcing ring 221 is disposed only on the uppermost surface in FIG. 15A, it is possible to constitute, as a whole, a bulk magnet having the planar reinforcing rings 221 and 227 on both of the uppermost and lowermost surfaces.

The second configuration example of the ring-shaped stack according to this embodiment has been described above. According to this configuration example, the planar reinforcing ring 220 is disposed between the layered ring-shaped bulk bodies 210 and at the ends in the central axial direction. By alternately layering such a ring-shaped bulk body 210 and the planar reinforcing ring 220 to form a composite material, its strength can be enhanced. Furthermore, by using a material having a high thermal conductivity as the planar reinforcing ring 220 and the outer circumferential reinforcing ring 230, occurrence of quenching can also be suppressed. As a result, breakage of the ring-shaped bulk body 210 can be prevented even under a high magnetic field strength condition, a sufficient total magnetic flux amount can be obtained inside the bulk magnet, and a bulk magnet structure having excellent magnetic field uniformity can be provided.

Figure 15D:
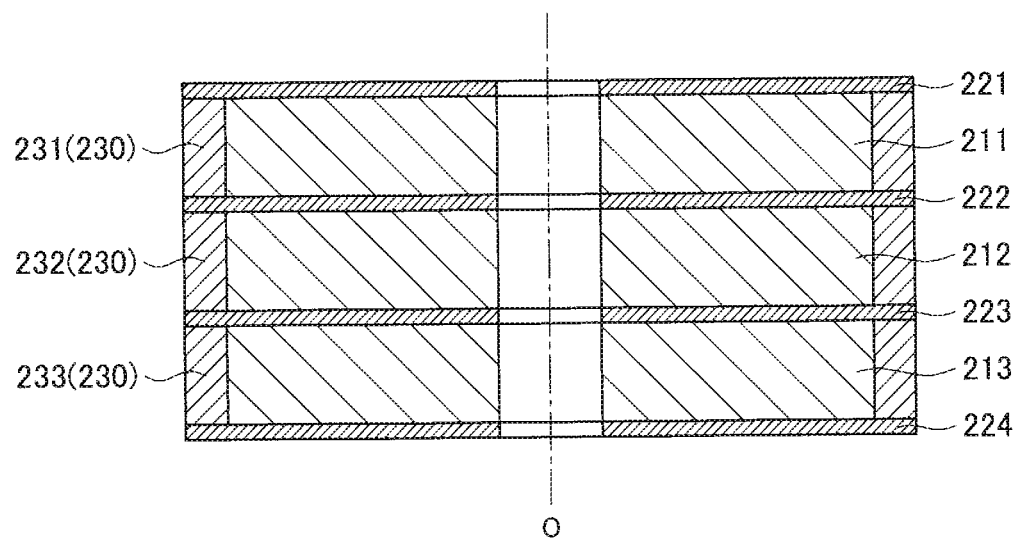
FIG. 15D shows a partial cross-sectional view of a modified example of the bulk magnet according to the same configuration example, taken along the central axis line of the bulk magnet.

Incidentally, in FIGS. 15A to 15C, the case where one outer circumferential reinforcing ring 230 is provided was shown, but the present invention is not limited to this example. For example, as shown in FIG. 15D, three divided outer circumferential reinforcing rings 231, 232 and 233 corresponding to three ring-shaped bulk bodies 212, 214 and 216 may be provided. In this case, the planar reinforcing rings 221, 223, 225 and 227 extended in the radial direction beyond the ring-shaped bulk bodies 212, 214 and 216 so that their outer diameters are aligned with the outer diameters of the outer circumferential reinforcing rings 231, 232 and 233.

Third Configuration Example

Figure 16:
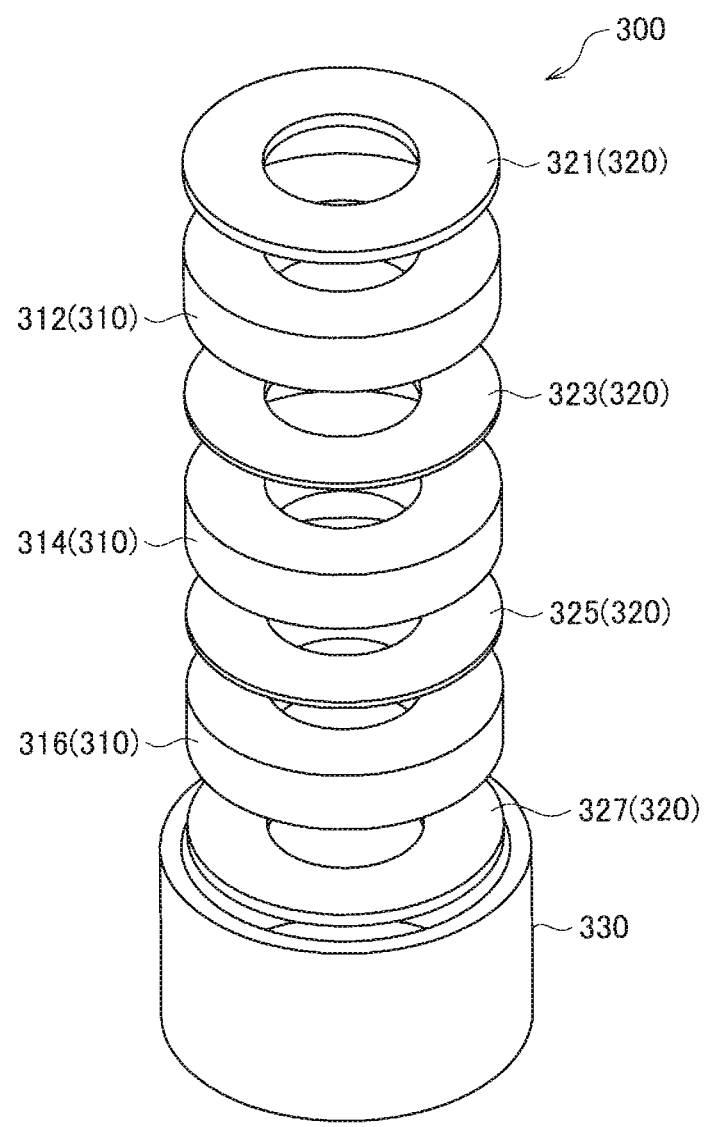
FIG. 16 is a schematic exploded perspective view showing a bulk magnet formed by a ring-shaped stack according to a third configuration example of a ring-shape stack.

Next, the third configuration example of the ring-shaped stack according to this embodiment will be described with reference to FIG. 16. FIG. 16 is a schematic exploded perspective view showing an example of the bulk magnet constituted by the ring-shaped stack according to this configuration example.

As shown in FIG. 16, the bulk magnet 300, which is constituted by the ring-shaped stack according to this configuration example, comprises a ring-shaped bulk body 310, a planar reinforcing ring 320 and an outer circumferential reinforcing ring 330. In this configuration example, three ring-shaped bulk bodies 312, 314 and 316 are provided as the ring-shaped bulk body 310, and four planar ring reinforcing rings 321, 323, 325 and 327 are provided as the planar reinforcing ring 320.

The ring-shaped bulk body 310 and the planar reinforcing ring 320 are alternately layered in the central axial direction of the ring. For example, as shown in FIG. 16, the planar reinforcing ring 323 is disposed between the ring-shaped bulk bodies 312 and 314, and the planar reinforcing ring 325 is disposed between the ring-shaped bulk bodies 314 and 316. Further, the ring-shaped bulk body 312 is provided with a planar reinforcing ring 321 on the surface opposite to the side on which the planar reinforcing ring 323 is disposed. Similarly, a ring-shaped bulk body 316 is provided with a planar reinforcing ring 327 on a surface opposite to the side on which the planar reinforcing ring 325 is disposed. Incidentally, the bonding or adhesion between the ring-shaped bulk body 310 and the planar reinforcing ring 320 layered on each other in the central axial direction may be performed in the same manner as the ring-shaped stack according to the first configuration example.

The ring-shaped stack constituting the bulk magnet 300 according to this configuration example is different from the ring-shaped stack according to the second configuration example in that the thickness of at least one of the planar reinforcing rings 321 and 327 on the uppermost or lowermost surface in FIG. 16 is greater than the thickness of the other planar reinforcing rings 323 and 325. This is because the maximum stress is applied to the surfaces of the upper surface and the lower surface of the bulk magnet 300 during the magnetization process, and thus it is necessary to sufficiently reinforce this portion. Like the bulk magnet 300 according to this embodiment, by increasing the thickness of high strength reinforcing members 321 and 327 on the uppermost or lowermost surfaces of the bulk magnet 300, it is possible to ensure sufficient strength to withstand the maximum stress.

As in the case of the ring-shaped stack according to the second configuration example, for example, by arranging a bulk magnet in which the planar reinforcing ring 321 is disposed only on the uppermost surface in FIG. 16 and a bulk magnet in which the high strength reinforcing member 327 is disposed only on the lowermost surface in FIG. 16 to the bulk magnet structure, it is possible to constitute a bulk magnet structure in which the planar reinforcing rings 321 and 327 are disposed on both the uppermost and lowermost surfaces of the bulk magnet structure as a whole.

Fourth Configuration Example

Figure 17:
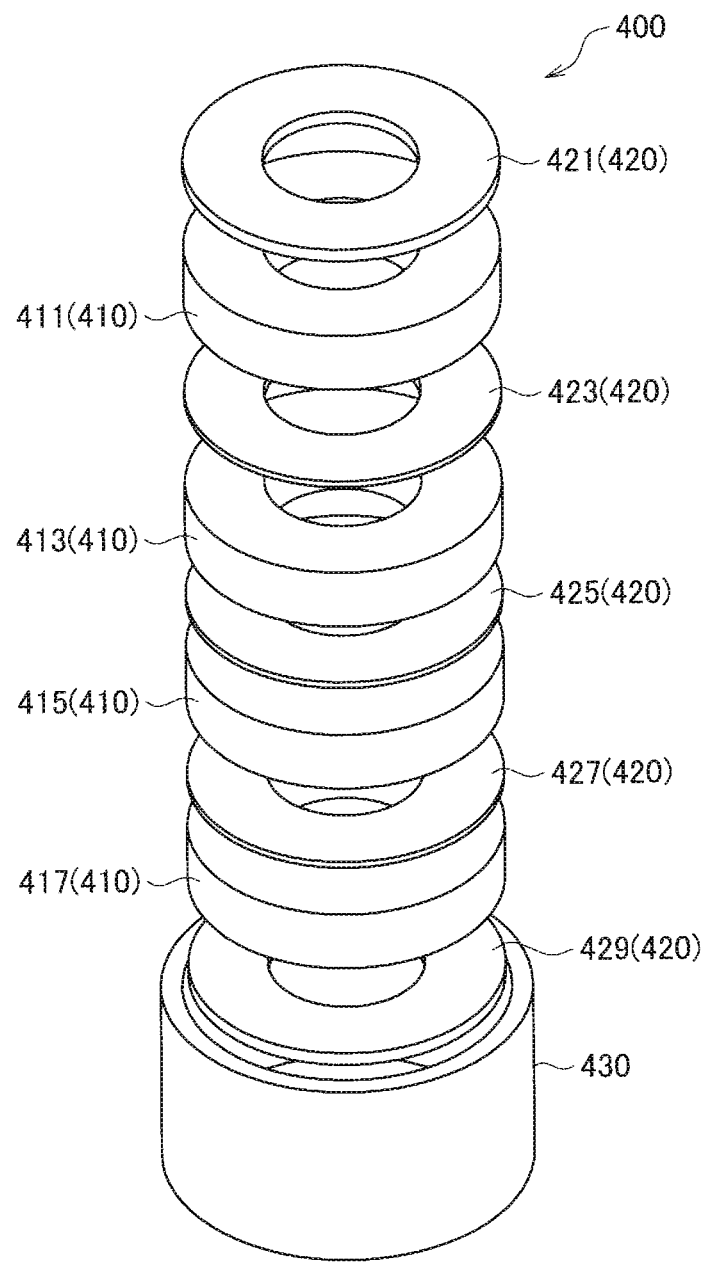
FIG. 17 is a schematic exploded perspective view showing a bulk magnet formed by a ring-shaped stack according to a fourth configuration example of a ring-shaped stack.

Next, the fourth configuration example of the ring-shaped stack according to this embodiment will be described with reference to FIG. 17. FIG. 17 is a schematic exploded perspective view showing the bulk magnet 400 constituted by the ring-shaped stack according to this embodiment.

The bulk magnet 400, which is constituted by a ring-shaped stack according to this configuration example, comprises a ring-shaped bulk body 410, a planar reinforcing ring 420 and an outer circumferential reinforcing ring 430. In the fourth ring-shaped stack, four ring-shaped bulk bodies 412, 414, 416 and 418 are provided as the ring-shaped bulk body 410, and five planar reinforcing rings 421, 423, 425, 427 and 429 are provided as the planar reinforcing ring 420.

Compared with the ring-shaped stacks according to the first configuration to the third configuration, the ring-shaped stack constituting the bulk magnet 400 according to this configuration example has a planar reinforcing ring 420 whose inner diameter is smaller than the inner diameter of the ring-shaped bulk body 410. The inner circumferential surface of the ring-shaped bulk body 410 is a portion where the stress concentrates in the magnetization process. When cracking occurs in the bulk magnet 400, it often occurs from this portion. By reducing the inner diameter of the planar reinforcing ring 420, the effect of suppressing the occurrence of cracks from the inner circumferential surface of the ring-shaped bulk body 410 can be enhanced. In addition, when the inner diameters of the ring-shaped bulk bodies 410 disposed above and under the planar reinforcing ring 420 are different from each other, the inner diameter of the planar reinforcing ring 420 needs to be smaller than the inner diameter of the ring-shaped bulk body having a smaller inner diameter. By strengthening the portion which may become a starting point of cracking, the reinforcing effect against the cracking can be enhanced. The starting point of cracking of the ring-shaped bulk body 410 may be on the inner circumferential surface, and it is particularly preferable to reinforce the intersection line portion between the upper surface or the lower surface and the inner circumferential surface. Therefore, by making the inner diameter of the planar reinforcing ring 420 smaller than the inner diameter of the ring-shaped bulk body 410 having a smaller inner diameter, it is possible to reinforce the ring-shaped bulk body 410 having a smaller inner diameter. Furthermore, by using a material having high thermal conductivity as the planar reinforcing ring 420 and the outer circumferential reinforcing ring 430, occurrence of quenching can be suppressed.

Fifth Configuration Example

Figure 18A:
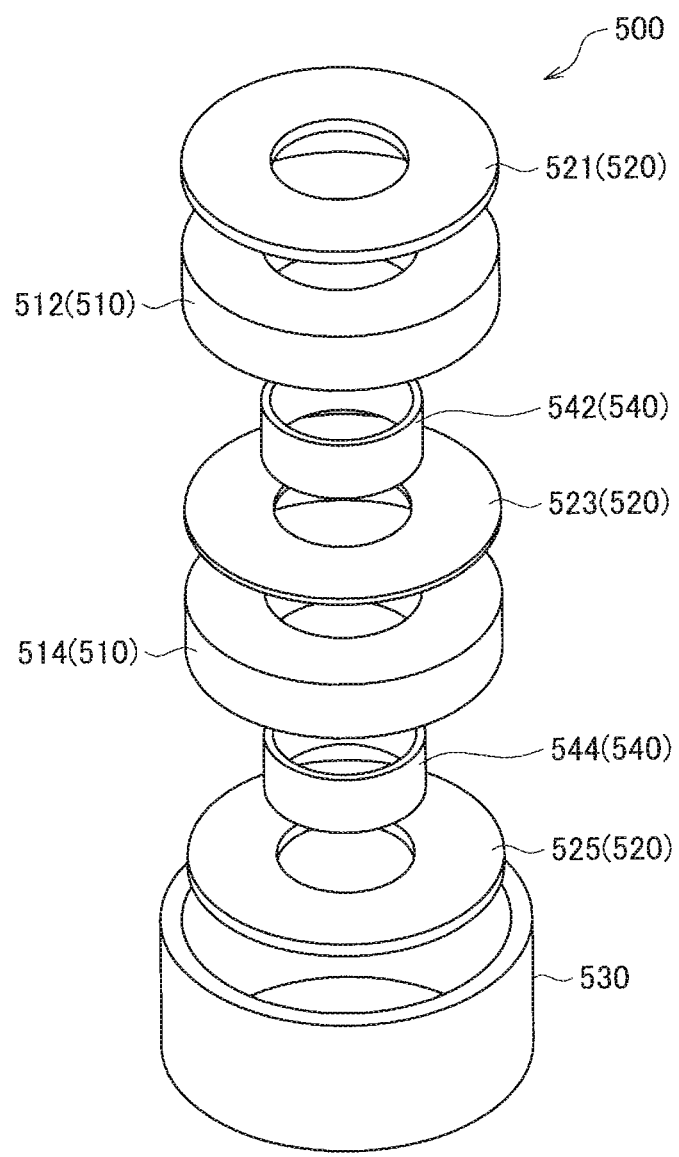
FIG. 18A is a schematic exploded perspective view showing a bulk magnet formed by a ring-shaped stack according to a fifth configuration example of a ring-shaped stack.

Next, the fifth configuration example of the ring-shaped stack according to this embodiment will be described with reference to FIGS. 18A to 18E. FIG. 18A is a schematic exploded perspective view showing a bulk magnet 500 constituted by the ring-shaped stack according to this embodiment. FIGS. 18B to 18E shows partial cross-sectional views of modified examples of the bulk magnet according to this embodiment, taken along the central axis of the bulk magnet 500.

The bulk magnet 500 constituted by the ring-shaped stack according to this configuration example, comprises a ring-shaped bulk body 510, a planar reinforcing ring 520, an outer circumferential reinforcing ring 530 and an inner circumferential reinforcing ring 540. In the example shown in FIG. 18A, two ring-shaped bulk bodies 512 and 514 are provided as the ring-shaped bulk body 510, and three planar reinforcing rings 521, 523 and 525 are provided as the planar reinforcing ring 520. Further, two inner circumferential reinforcing rings 542 and 544 are provided as the inner circumferential reinforcing ring 540.

Compared to the ring-shaped stacks according to the first configuration example to the fourth configuration example, the ring-shaped stack constituting the bulk magnet 500 according to this configuration example is different in that an inner circumferential reinforcing ring 540 for reinforcing the inner circumferential surface of the ring-shaped bulk body 510 is bonded or adhered to the inner circumferential surface of the ring-shaped bulk body 510. Since the inner circumferential reinforcing ring 540 is also bonded or adhered to the planar reinforcing ring 520, even when its linear expansion coefficient is larger than that of the ring-shaped bulk body 510, the inner circumferential reinforcing ring 540 can be firmly bonded to the inner circumferential surfaces of the ring-shaped bulk body 510 and the planar reinforcing ring 520. Therefore, these inner circumferential surfaces can be reinforced, which has an effect of suppressing cracking.

Furthermore, by using a material having high thermal conductivity as the planar reinforcing ring 520, the inner circumferential reinforcing ring 540 and the outer circumferential reinforcing ring 530, occurrence of quenching can be suppressed. In this case, the planar reinforcing ring 520 and the outer circumferential reinforcing ring 530 can be configured in the same manner as the ring-shaped stack according to the first configuration example. Also for the inner circumferential reinforcing ring 540, for example, a material containing a metal having a high thermal conductivity, such as copper, aluminum, silver or the like as a main component can be used in order to enhance the quench suppressing effect. From the viewpoint of transfer and absorption of heat generated in the superconducting material, the thermal conductivity of the inner circumferential reinforcing ring 540 having a high thermal conductivity is desirably 20 W/(m·K) or more, and more desirably 100 W/(m·K) or more at a temperature range of 20K to 70K at which temperature a strong magnetic field can be stably generated by a freezer or the like. In addition, the inner circumferential reinforcing ring 540 may be formed by disposing a plurality of rings concentrically. That is, one inner circumferential reinforcing ring can be constituted as a whole by bringing the opposed rings in contact with each other on their circumferential surfaces. In this case, it is sufficient that at least one of the rings constituting the inner circumferential reinforcing ring has a thermal conductivity of 20 W/(m·K) or more.

Figure 18B:
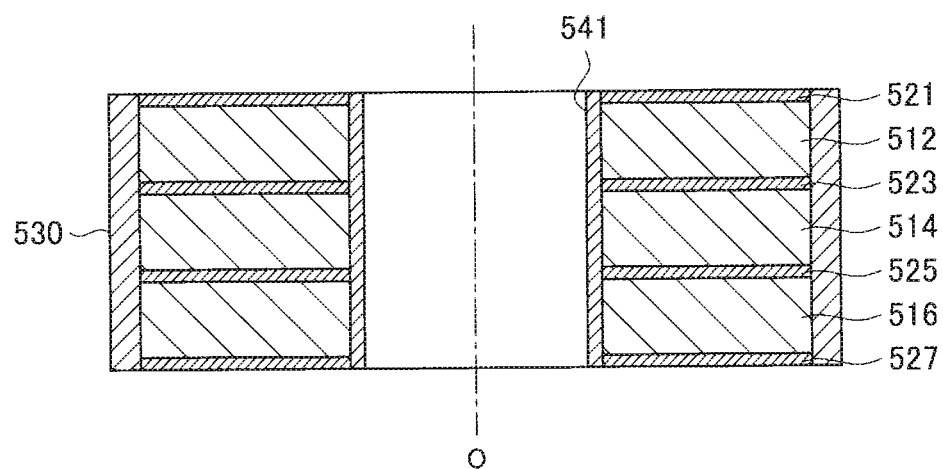
FIG. 18B shows a partial cross-sectional view of a modified example of the bulk magnet according to the same configuration example, taken along the center axis of the bulk magnet.

In this case, it is preferable to bring the inner circumferential surface of the ring-shaped bulk body 510 and the outer circumferential surface of the inner circumferential reinforcing ring 540 into close contact with each other. Further, as a basic positional relationship between the inner circumferential reinforcing ring 540 and the planar reinforcing ring 520, for example, as shown in FIG. 18B, the inner diameter of the ring-shaped bulk body 510 and the inner diameter of the planar reinforcing ring 520 are set to be the same so that one inner circumferential reinforcing ring 541 may be provided.

Figure 18C:
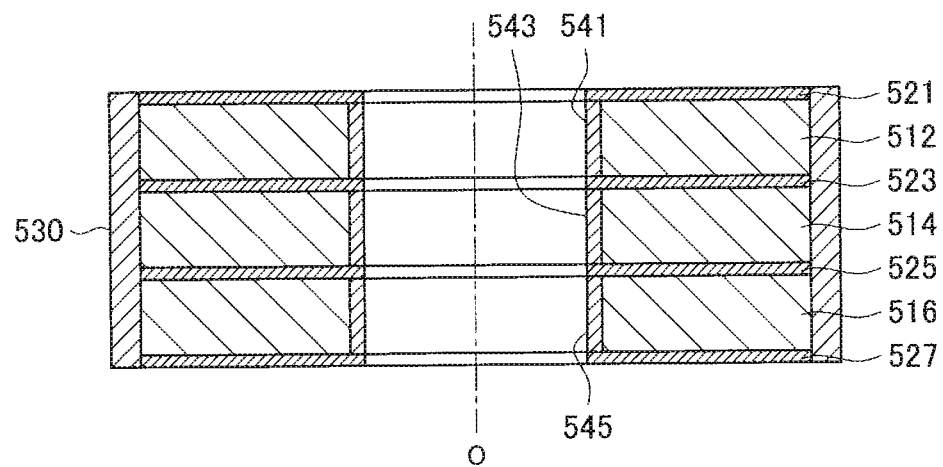
FIG. 18C shows a partial cross-sectional view of a modified example of the bulk magnet according to the same configuration example, taken along the center axis of the bulk magnet.
Figure 18D:
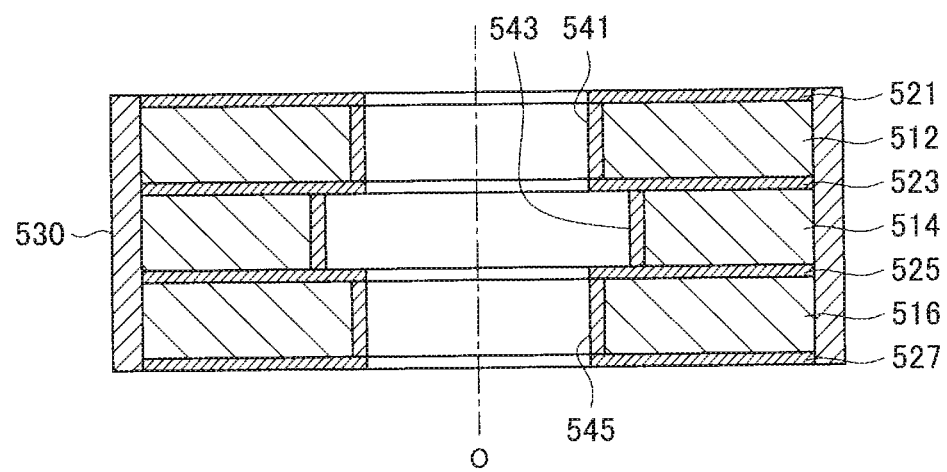
FIG. 18D shows a partial cross-sectional view of a modified example of the bulk magnet according to the same configuration example, taken along the center axis of the bulk magnet.

Alternatively, as shown in FIG. 18C, the inner diameter of the planar reinforcing ring 520 is slightly smaller than the inner diameter of the ring-shaped bulk body 510, and the inner circumferential surface of each of the ring-shaped bulk bodies 512, 514 and 516 may be provided with inner circumferential reinforcing rings 541, 543 and 545, respectively so that the inner diameters of the planar reinforcing rings 521, 523 and 525 and the inner diameters of the inner circumferential reinforcing rings 541, 543 and 545 are the same. In the case where the thickness of the inner circumferential reinforcing ring 540 is greater than the thickness of the planar reinforcing ring 520, it is preferable to constitute the structure shown in FIG. 18C from the viewpoint of strength. As a result, the contact area between the inner circumferential reinforcing ring 540 and the planar reinforcing ring 520 can be increased, and the strength of the connecting portion between the inner circumferential reinforcing ring 540 and the planar reinforcing ring 520 can be enhanced. Further, when the inner diameter of the ring-shaped bulk body 510 varies, the inner circumferential reinforcing ring 540 is desirably divided into the inner circumferential reinforcing rings 541, 543 and 545, as shown in FIG. 18D from the viewpoint of workability.

Figure 18E:
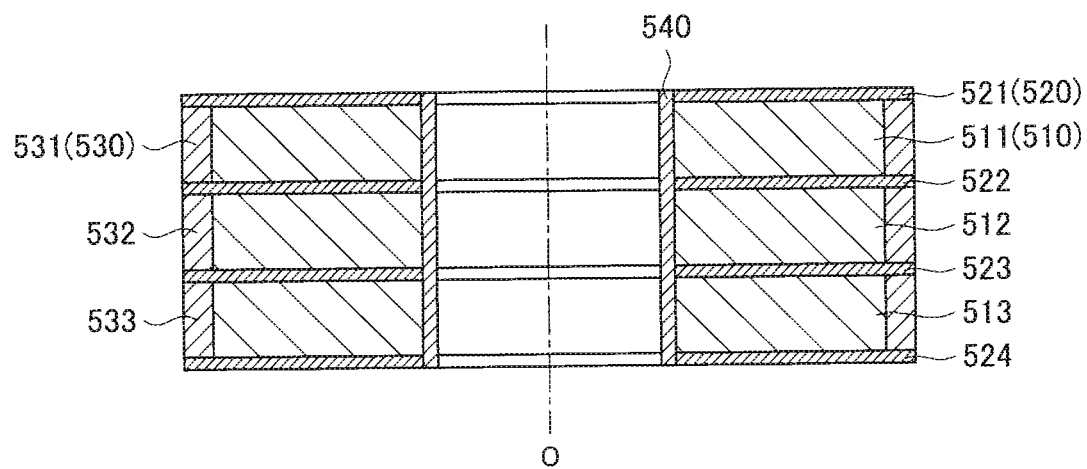
FIG. 18E shows a partial cross-sectional view of a modified example of the bulk magnet according to the same configuration example, taken along the center axis of the bulk magnet.

Incidentally, in FIGS. 18A to 18D, an example wherein one outer circumferential reinforcing ring 530 is provided is shown, but the present invention is not limited to this example. For example, as shown in FIG. 18E, three divided circumferential reinforcing rings 531, 532 and 533 corresponding to three ring shaped bulk bodies 512, 514 and 516 may be provided. In this case, the planar reinforcing rings 521, 523, 525 and 527 extend in the radial direction beyond the ring-shaped bulk bodies 512, 514, 516 so that the outer diameters of the planar reinforcing rings 521, 523, 525, 527 are aligned with the outer diameters of the outer circumferential reinforcing rings 531, 532 and 533.

Sixth Configuration Example

Figure 19A:
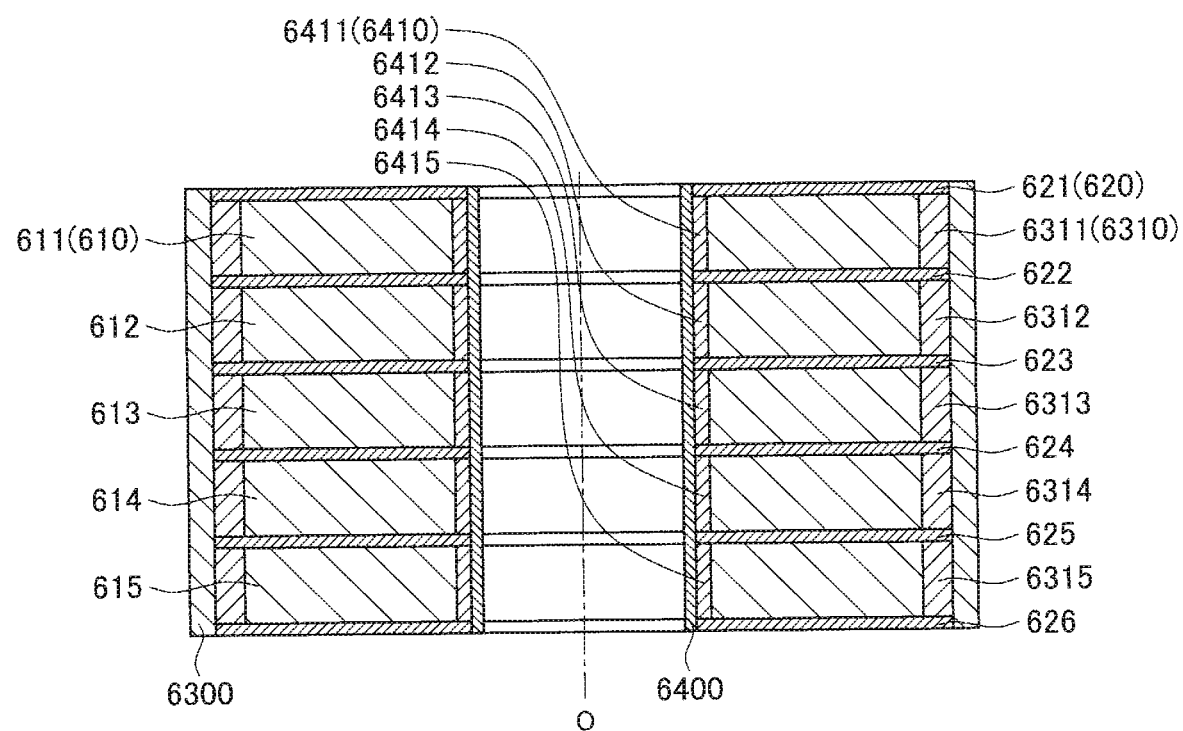
FIG. 19A shows a partial cross-sectional view of a bulk magnet formed by a ring-shaped stack according to a sixth configuration example of a ring-shaped stack, taken along the central axis of the bulk magnet.
Figure 19B:
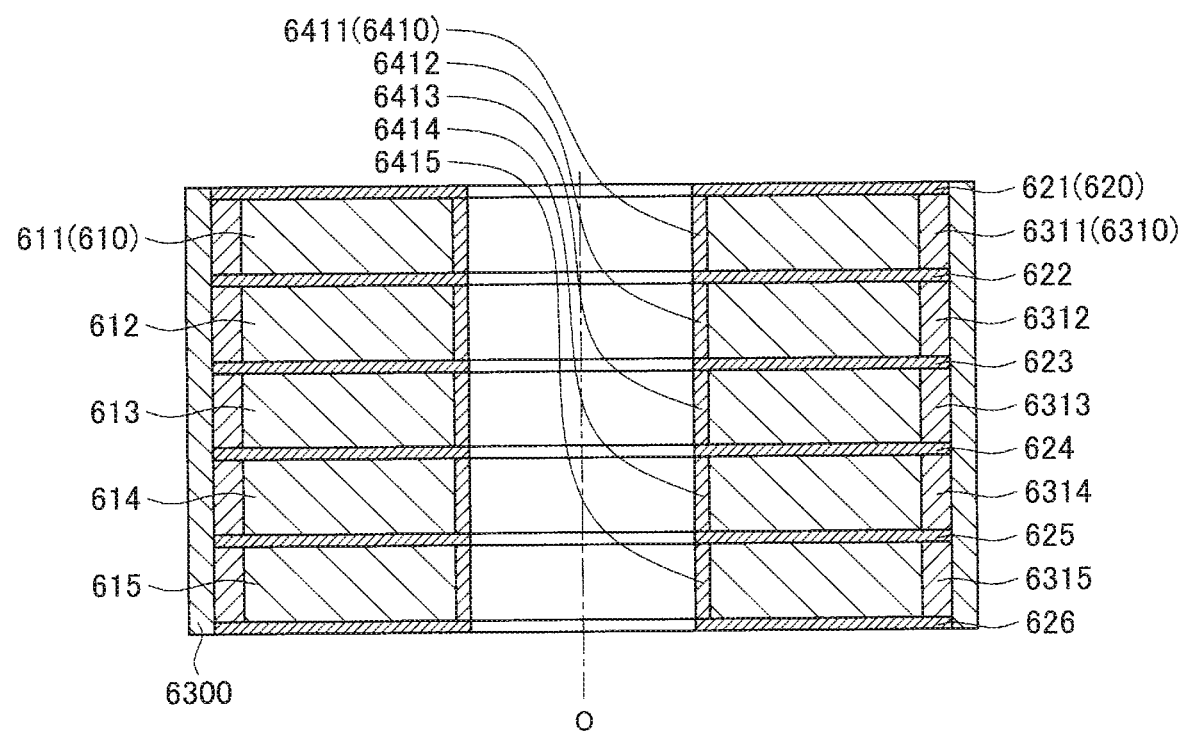
FIG. 19B shows a partial cross-sectional view of a modified example of a bulk magnet formed by a ring-shaped stack according to the same configuration example, taken along the central axis of the bulk magnet.
Figure 19C:
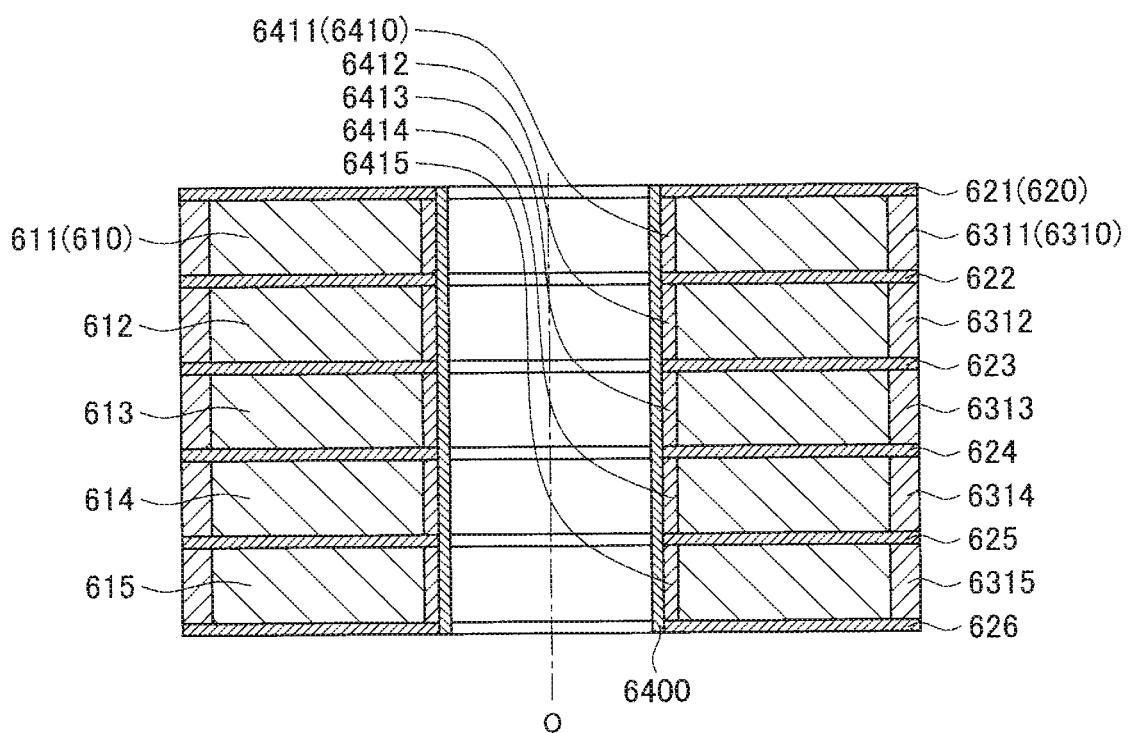
FIG. 19C shows a partial cross-sectional view of a modified example of a bulk magnet formed by a ring-shaped stack according to the same configuration example, taken along the central axis of the bulk magnet.

Next, the sixth configuration example of the ring-shaped stack according to this embodiment will be described with reference to FIGS. 19A to 19C. FIGS. 19A to 19C shows partial cross-sectional views of the bulk magnet 600 constituted by the ring-shaped stack according to this configuration example and its modified example, taken along the central axis thereof.

The bulk magnet 600 constituted by the ring-shaped stack according to this configuration example, comprises a ring-shaped bulk body 610, a planar reinforcing ring 620, an outer circumferential reinforcing ring 6300, a second outer circumferential reinforcing ring 6310, an inner circumferential reinforcing ring 6400 and a second inner circumferential reinforcing ring 6410. In the example shown in FIG. 19A, five ring-shaped bulk bodies 611-615 are provided as the ring-shaped bulk body 610, and six planar reinforcing rings 621-626 are provided as the planar reinforcing ring 620. In addition, on the inner circumferential surface and the outer circumferential surface of each of the ring-shaped bulk bodies 611-615, second outer reinforcing rings 6311-6315 and second inner reinforcing rings 6411-6415 are provided.

Compared with the ring-shaped stack according to the first configuration example to the configuration example, the ring-shaped stack constituting the bulk magnet 600 according to this configuration example is different in that the outer circumferential end portion of the planar reinforcing ring 620 is bonded with the second outer circumferential reinforcing ring and the outer circumferential reinforcing ring and the inner circumferential end portion of the planar reinforcing ring 620 is bonded with the second inner circumferential reinforcing ring and the inner circumferential reinforcing ring. Here, since the second outer circumferential reinforcing ring, the outer circumferential reinforcing ring, the second inner circumferential reinforcing ring and the inner circumferential reinforcing ring are made of metal, they can be firmly connected to the metal planar reinforcing ring with solder or the like. Therefore, the ring-shaped bulk bodies 611-615 can be fastened and firmly connected from the lateral surface and the upper and lower surfaces in two directions by double structures of the second inner circumferential reinforcing ring and the inner circumferential reinforcing ring, and of the second outer circumferential reinforcing ring and the outer circumferential reinforcing ring. By this effect, the ring-shaped bulk body 610 can be firmly bonded to the surrounding planar reinforcing ring, the second inner circumferential reinforcing ring and the second circumferential reinforcing ring, and has a remarkable effect of suppressing cracking.

Further, by using a material having a high thermal conductivity for the planar reinforcing ring 620, the double structure of the second inner circumferential reinforcing ring 6410 and the inner circumferential reinforcing ring 6400, and the double structure of the outer circumferential reinforcing ring 6300 and the second circumferential reinforcing ring 6310, the occurrence of quenching can be suppressed. In this case, the planar reinforcing ring 620, the outer circumferential reinforcing ring 6300 and the second outer circumferential reinforcing ring 6310 can be configured in the same manner as the ring-shaped stack according to first configuration example. For the second inner circumferential reinforcing ring 6410 and the inner circumferential reinforcing ring 6400, for example, a material containing a metal having a high thermal conductivity such as copper, aluminum, silver or the like as a main component is used in order to enhance the quench suppressing effect. The thermal conductivity of the second inner circumferential reinforcing ring 6410 and the inner circumferential reinforcing ring 6400 having a high thermal conductivity is desirably 20 W/(m·K) or more, and more desirably 100 W/(m·K) or more at a temperature range of 20K to 70K at which temperature a strong magnetic field can be stably generated by a freezer or the like, from the viewpoint of the transfer and absorption of heat generated in the superconducting material.

Further, the second inner circumferential reinforcing ring 6410 and the inner circumferential reinforcing ring 6400 may be formed by arranging a plurality of rings concentrically. That is, one second inner circumferential reinforcing ring 6410 and one inner circumferential reinforcing ring 6400 as a whole are formed so that the circumferential surfaces of the opposing rings are brought into contact with each other. In this case, at least one of the materials constituting the second inner circumferential reinforcing ring 6410 or the inner circumferential reinforcing ring 6400 may have a thermal conductivity of 20 W/(m·K) or more.

FIG. 19B shows an example of a case where the outer circumferential end portion of the planar reinforcing ring is bonded from the lateral surface and the upper and lower surfaces by a double ring structure only in the outer circumference as a modified example of FIG. 19A. This is because the inner circumferential end portion of the planar reinforcing ring may be bonded only on its upper and lower surfaces by the inner circumferential reinforcing ring, for example, in the case where it is necessary to ensure a certain inner diameter in terms of design. Similarly, FIG. 19C shows an example of a case where the inner circumferential end portion of the planar reinforcing ring is bonded from the lateral surface and the upper and lower surfaces by a double ring structure only in the inner circumference. This is because the outer circumferential end portion of the planar reinforcing ring may be bonded only on its upper and lower surfaces by the outer circumferential reinforcing ring, for example, in the case where the selection of the outer diameter is limited in terms of design.

Seventh Configuration Example

Figure 20:
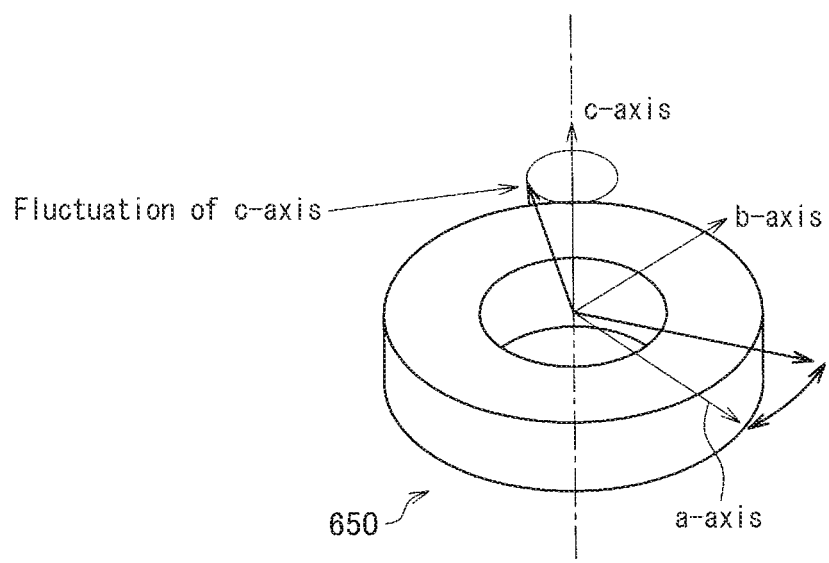
FIG. 20 is an explanatory view showing a fluctuation of a crystallographic orientation of a ring-shaped bulk body constituting a ring-shaped stack according to a seventh configuration example of a ring-shaped stack.

Next, the seventh configuration example of the ring-shaped stack according to this embodiment will be described with reference to FIG. 20. FIG. 20 is an explanatory diagram showing the fluctuation of the crystallographic orientation of the ring-shaped bulk body 650.

Since the ring-shaped bulk body 650 is a monocrystalline material, the anisotropy of the crystal orientation appears as disturbance of the captured magnetic flux density distribution (deviation from axial symmetry). In order to average the anisotropy of this crystal orientation, the ring-shaped bulk bodies 650 may be layered while shifting the crystal orientation of the ring-shaped bulk bodies 650.

When layering a plurality of ring-shaped bulk bodies 650, with respect to the relative crystal axis, it is preferable to arrange them so that the c-axis direction substantially coincides with the inner circumferential axis of each ring and at the same time shift the orientation of the a-axis. The ring-shaped bulk body 650 in which $RE_2BaCuO_5$ is finely dispersed in a monocrystalline $RE_1Ba_2Cu_3O_y$, generally has fluctuation in the crystal orientation of the monocrystalline $RE_1 Ba_2 Cu_3O_y$. The magnitude of the fluctuation in the c-axis direction is about ±15°. Herein, the fact that the c-axis direction substantially coincides with the inner circumferential axis of each ring means that the deviation of the monocrystalline crystal orientation is about ±15°. Although the angle of shifting the a-axis depends on the number of layering, it is preferable that the angle not be of quadruple symmetry, such as 180°, 90° or the like.

In this way, by layering the ring-shaped bulk bodies 650 while shifting the crystal orientation of the ring-shaped bulk bodies 650, the anisotropy of the crystal orientation can be averaged.

Eighth Configuration Example

Figure 21A:
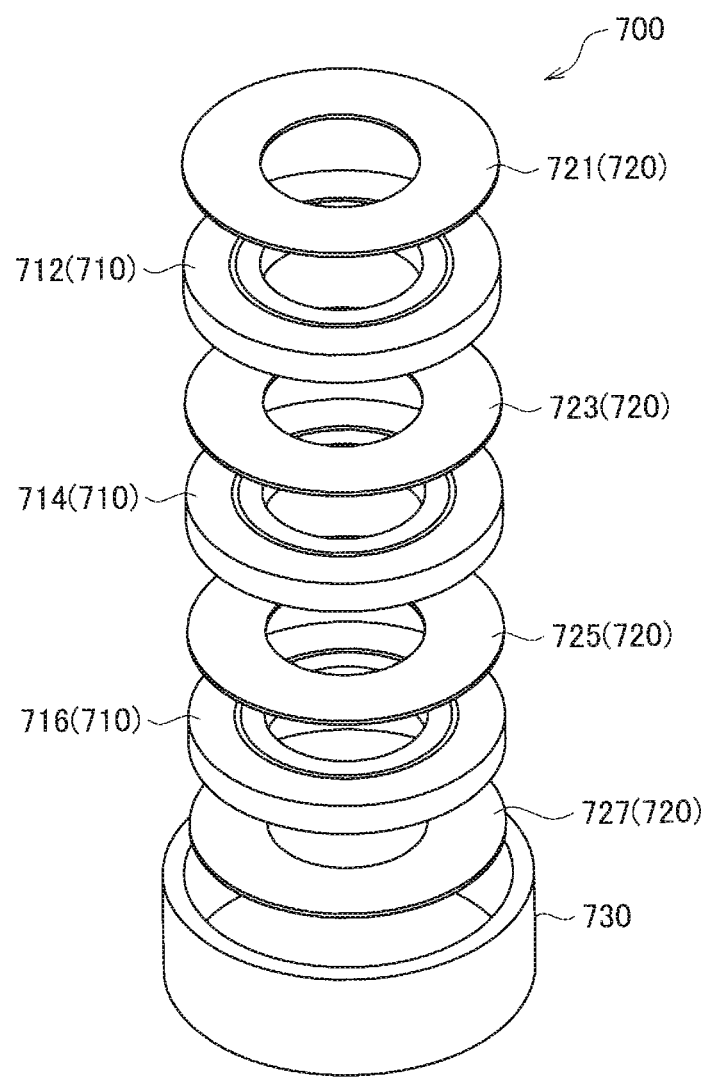
FIG. 21A is a schematic exploded perspective view showing a bulk magnet formed by a ring-shaped stack according to an eighth configuration example of a ring-shaped stack.
Figure 21B:
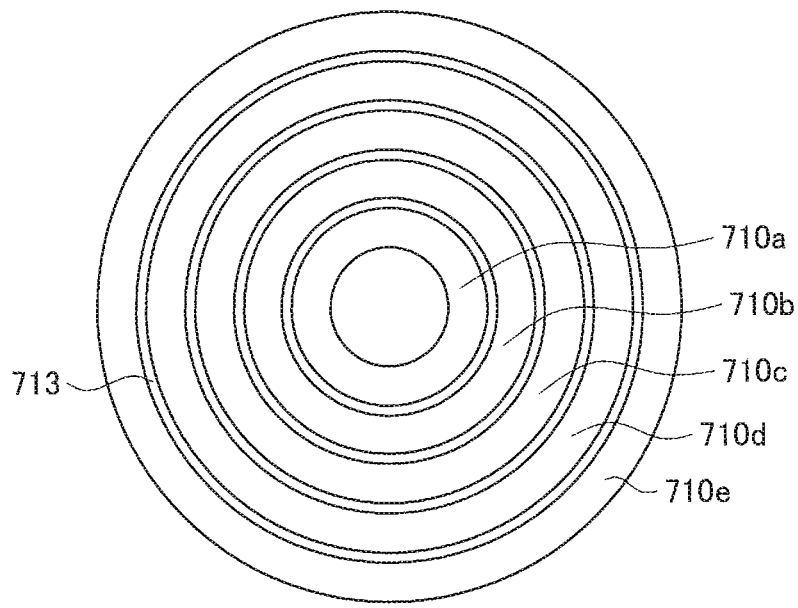
FIG. 21B shows a plan view of an example of a ring-shaped bulk body constituting a ring-shaped stack according to the same configuration example.
Figure 21C:
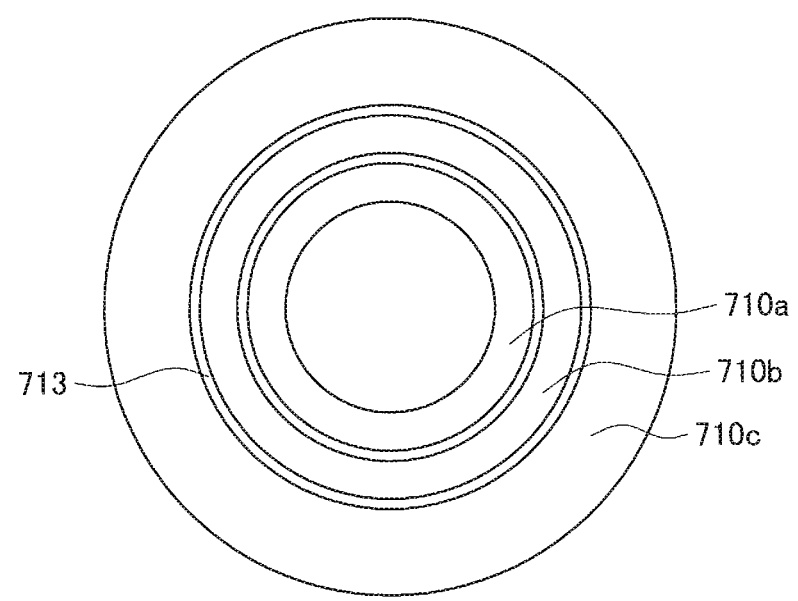
FIG. 21C shows a plan view of an example of a ring-shaped bulk body constituting a ring-shaped stack according to the same configuration example.
Figure 21D:
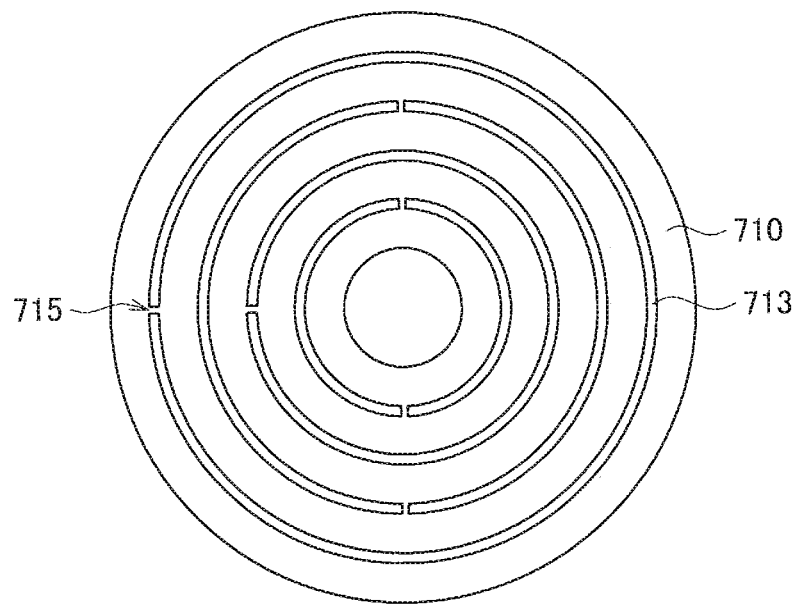
FIG. 21D shows a plan view of an example of a ring-shaped bulk body constituting a ring-shaped stack according to the same configuration example.

Next, the eighth configuration example of the ring-shaped stack according to this embodiment will be described with reference to FIGS. 21A to 21D. FIG. 21A is a schematic exploded perspective view showing an example of the bulk magnet 700 constituted by the ring-shaped stack according to this configuration example. FIGS. 21B to 21D shows plan views of examples of the ring-shaped bulk bodies 710 constituting the ring-shaped stack according to this configuration example.

As compared to the ring-shaped stack according to the first configuration example to the seventh configuration example, the bulk magnet 700 constituted by the ring-shaped stack according to this configuration example is different in that the oxide superconducting bulk body 710 has a multiple ring structure in the radial direction. The multiple ring structure is not a single ring in the radial direction but a structure in which a plurality of rings are concentrically arranged. For example, as shown in FIG. 21B, the ring-shaped bulk body 710 has ring-shaped bulk bodies 710a-710e having different inner and outer diameters and substantially the same radial widths, with a predetermined gap 713 in the radial direction, which may be a concentrically arranged quintuple ring structure.

Further, as shown in FIG. 21C, the ring-shaped bulk body 710 may be a concentrically arranged quadruple ring structure, in which the ring-shaped bulk bodies 710a-710c having different inner and outer diameters are comprised with a predetermined gap 713 in the radial direction. In this case, the radial width of the ring-shaped bulk body 710c may be greater than the radial width of the other ring-shaped bulk bodies 710a and 710b. The width of each ring is a design matter.

By layering the ring-shaped bulk bodies 710 having such a multiple ring structure, the ring-shaped bulk bodies 710 have a tendency that a quadruple symmetry is slightly reflected also in the superconducting current distribution due to crystal growth accompanying quadruple symmetry. However, by forming a concentric multiple ring, there is an effect that brings the flow path of superconducting current induced by magnetization close to axisymmetric one. This effect improves the uniformity of the captured magnetic field. The bulk magnet 700 having such characteristics is suitable for NMR and MRI application, particularly where a high magnetic field uniformity is required.

Further, as shown in FIG. 21D, for example, the ring-shaped bulk body 710 can be formed by forming concentric circular arc-shaped gaps 713 in one ring and forming a plurality of seams 715 in the circumferential direction of the gap 713 on the same circumference. By doing so, the work of assembling the bulk magnet 700 can be simplified.

(Configuration Example of Columnar Stack)

The configuration example of the ring-shaped stack according to the fourth embodiment has been described above. Incidentally, the columnar stack according to the third and fourth embodiments can have the same configuration as each of the constitutional examples of the ring-shaped stack described above. Specifically, the configurations as shown in FIGS. 6 to 15D (except the inner circumferential reinforcing ring and the second inner circumferential reinforcing ring) can be applied to the columnar stack. Main configuration examples of the columnar stack will be described below.

First Configuration Example

Figure 22:
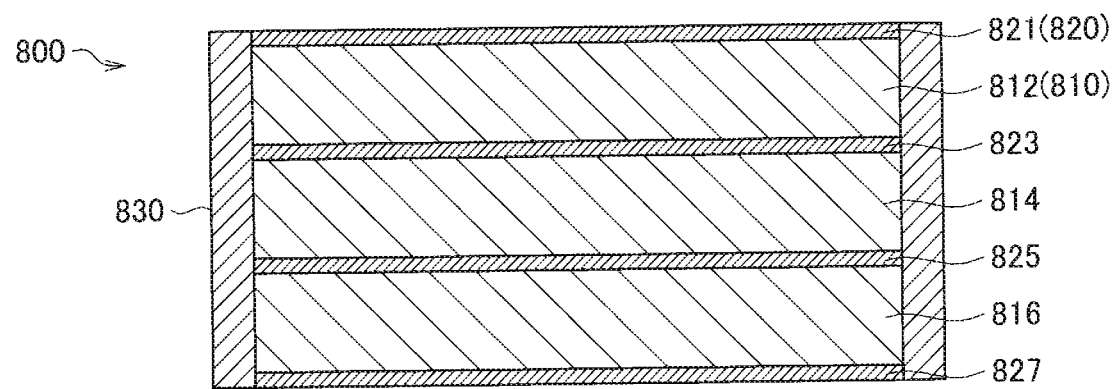
FIG. 22 shows a partial cross-sectional view of a bulk magnet formed by a columnar stack according to a first configuration example of a columnar stack, taken along the central axis of the bulk magnet.

First, a first configuration example of a columnar stack according to this embodiment will be described with reference to FIG. 22. FIG. 22 shows a partial cross-sectional view taken along a central axis of the bulk magnet 800 constituted by the columnar stack according to this configuration example. The layered structure of the columnar stack shown in FIG. 22 corresponds to the layered structure of the ring-shaped stack shown in FIG. 15B (that is, the second configuration example of the ring-shaped stack).

In the bulk magnet 800 according to this configuration example, three columnar bulk bodies 812, 814 and 816 are provided as the columnar bulk body 810 made of an oxide superconducting body, and four planar reinforcing plates 821, 823, 825 and 827 are provided as the planar reinforcing plate 820. The columnar bulk body 810 and the planar reinforcing plate 820 are alternately layered in the central axis direction of the column. For example, as shown in FIG. 22, a planar reinforcing plate 823 is disposed between the columnar bulk bodies 812 and 814, and a planar reinforcing plate 825 is disposed between the columnar bulk bodies 814 and 816.

Further, on the columnar bulk body 812, a planar reinforcing plate 821 is provided on the surface opposite to the side on which the planar reinforcing plate 823 is disposed. Similarly, a planar reinforcing plate 827 is provided on the columnar bulk body 816 on the surface opposite to the side on which the planar reinforcing plate 825 is disposed. At this time, as shown in FIG. 22, the positional relationship between the planar reinforcing plate 821 at the very end portion and the planar reinforcing plate 827 at the other very end portion, is such that the planar reinforcing plates 821 and 827 may be contained in the reinforcing ring 830. Alternatively, the outer diameter of the planar reinforcing plates 821 and 827 may be substantially equal to the outer diameter of the outer circumferential reinforcing ring 830, and the end faces of the outer circumferential reinforcing ring 830 may be covered with the planar reinforcing plates 821 and 827.

According to this configuration example, the planar reinforcing plate 820 is disposed between the layered columnar bulk bodies 810 and the end portions in the central axis direction. By alternately layering the columnar bulk body 810 and the planar reinforcing plate 820 to form a composite material, it is possible to increase its strength as with the ring-shaped stack. Furthermore, by using a material having high thermal conductivity as the planar reinforcing plate 820 and the outer circumferential reinforcing ring 830, the occurrence of quenching can be suppressed. This makes it possible to prevent breakage of the columnar bulk body 810 even under a high magnetic field strength condition, to obtain a sufficient total magnetic flux amount inside the bulk magnet, and to provide a bulk magnet structure having excellent magnetic field uniformity.

Incidentally, although FIG. 22 shows a case where one outer circumferential reinforcing ring 830 is provided, the present invention is not limited to this example. For example, a plurality of the divided outer circumferential reinforcing rings corresponding to a plurality of columnar bulk bodies may be provided (see FIG. 15D). At this time, the planar reinforcing plate extends in the radial direction beyond the columnar bulk body so that the outer circumferential reinforcing ring and the reinforcing plate have the same outer diameter.

Second Configuration Example

Next, a second configuration example of the columnar stack according to this embodiment will be described with reference to FIG. 23. FIG. 23 shows a partial cross-sectional view taken along the central axis of the bulk magnet 900 constituted by the columnar stack according to this configuration example.

The bulk magnet 900 constituted by the columnar stack according to this configuration example comprises a columnar bulk member 910, a planar reinforcing plate 920, an outer circumferential reinforcing ring 9300, and a second outer circumferential reinforcing ring 9310. In the example shown in FIG. 23, three columnar bulk bodies 912, 914 and 916 are provided as the columnar bulk body 910, and four planar reinforcing plates 921, 923, 925 and 927 are provided as the planar reinforcing plate 920. Further, second outer circumferential reinforcing rings 9312, 9314 and 9316 are provided on the outer circumferential surfaces of the columnar bulk bodies 912, 914 and 916.

Compared to the columnar stack according to the first configuration example, the columnar stack constituting the bulk magnet 900 according to this configuration example is different in that the outer circumferential end portion of the planar reinforcing plate 920 is connected with the second outer circumferential reinforcing ring and the outer circumferential reinforcing ring Here, since the second outer circumferential reinforcing ring and the outer circumferential reinforcing ring can be made of a metal, they can be firmly connected to the planar metal reinforcing plate by soldering or the like. Therefore, the columnar bulk bodies 912, 914 and 916 can be fastened and firmly bonded from the lateral surface and the upper and lower surfaces in two directions by the second outer circumferential reinforcing ring and the outer circumferential reinforcing ring having a double structure. Due to this effect, the columnar bulk body 910 can be firmly bonded to the surrounding planar reinforcing plate and the second circumferential reinforcing ring, and has a remarkable effect of suppressing cracking.

(Others)

Incidentally, like the ring-shaped stack, by using a material having a high thermal conductivity as the planar reinforcing plate, the outer circumferential reinforcing ring and the second outer circumferential reinforcing ring constituting the columnar stack, it is possible to suppress the occurrence of quenching. In order to enhance the quench suppressing effect, for example, as each member, a material containing a metal having a high thermal conductivity, such as copper, aluminum, silver or the like as a main component can be used. The thermal conductivity of the planar reinforcing plate, the outer circumferential reinforcing ring and the second outer circumferential reinforcing ring having a high thermal conductivity is preferably 20 W/(m·K) or more, and more preferably 100 W/(m·K) or more in a temperature range of 20 K to 70K, at which temperature it is possible to stably generate a strong magnetic field by the freezer cooling or the like, from the viewpoint of transfer and absorption of heat generated in the superconducting material.

Further, the normal temperature tensile strength of the columnar bulk body is about 60 MPa, and usually normal temperature tensile strength of the solder for affixing the planar reinforcing plate to the columnar bulk body is usually less than 80 MPa. From this fact, the planar reinforcing plate having a normal temperature tensile strength of 80 MPa or more is effective as a reinforcing member. Therefore, it is preferable that the planar reinforcing plate have a normal temperature tensile strength of 80 MPa or more. In practical design of the bulk magnet, since the proportion of the superconducting material decreases by inserting the planar reinforcing plate made of a high-strength metal, the proportion of the planar reinforcing plate can be determined according to the intended use. From the above viewpoint, it is preferable that the planar reinforcing plate be formed by combining a plurality of high-strength metal having a high strength and a high-strength metal having high thermal conductivity in a certain ratio.

EXAMPLES

Examples of the present invention will be described below. The following examples are merely for demonstrating the effect of the present invention, and the present invention is not limited to them.

Example 1

In Example 1, the bulk magnet structure according to the above first embodiment was fabricated, the bulk magnet structure was magnetized by a superconducting magnet, and the magnetic field distribution on the central axis of the magnetized bulk magnet structure was measured using a probe inserted from the sample insertion port.

First, four columnar bulk bodies having an outer diameter of 70 mm and a thickness of 20 mm and having a structure in which $Gd_2BaCuO_5$ was finely dispersed in a monocrystalline $GdBa_2Cu_3O_y$, and two columnar bulk bodies having an outer diameter of 70 mm and a thickness of 10 mm having the same structure were prepared. These six bulk bodies were fitted into an outer circumferential reinforcing ring made of stainless steel (SUS 316 L) having an outer diameter of 90 mm and an inner diameter of 70 mm. At this time, solder was used for bonding each bulk body and the outer circumferential reinforcing ring.

In addition, a columnar member made of aluminum alloy having a thickness of 15 mm and an outer diameter of 90 mm was processed to produce the spacer shown in FIG. 6A. In addition, measurements were also made in the case where no spacer was used.

Next, as shown in FIGS. 5A and 5B, a bulk magnet structure was produced by layering bulk bodies, etc., and the bulk magnet structure was stored in a vacuum heat insulation container. Specifically, first, two columnar bulk magnets having a thickness of 20 mm and one columnar bulk magnet having a thickness of 10 mm were layered on the cold head 21, and the third container 10c was disposed. Next, the spacer 52 was placed on the columnar bulk magnet and the second container 10b was placed on the third container 10c. Next, one columnar bulk magnet having a thickness of 10 mm and two columnar bulk magnets having a thickness of 20 mm were layered on the spacer 52, and the first container 10a was placed on the second container 10b. In the case of using no spacer, the upper bulk magnet was supported by making the above flange of the second container 10b project in the direction of the central axis so that the upper bulk magnet and the lower bulk magnet were spaced apart from each other (See FIG. 5C). Each container was connected by screwing each flange.

The bulk magnet structure was fixed on the cold head, the vacuum heat insulation layer in the vacuum heat insulation container was evacuated and then cooled to 100K. The cold head portion of the cooling device was inserted into the room temperature bore of the superconducting magnet so that the central axis of the bulk magnet structure coincided with the central axis of the superconducting magnet (not shown). Thereafter, the superconducting magnet was energized to excite the superconducting magnet such that the center magnetic field of the superconducting magnet became about 5 T. Incidentally, when the spacer was not used, the lower bulk body portions 51d-51f were cooled in a state of being placed on the cold head 21 of the cooling device 20. The upper bulk body portions 51a-51c were cooled by using a refrigerant (helium gas or the like) after forming the outer wall in a double structure and providing a vacuum heat insulating layer between the double outer walls.

After completing excitation of the superconducting magnet, the bulk magnet structure was cooled to 25 K. After the temperature stabilized, the applied magnetic field of the superconducting magnet was demagnetized to zero magnetic field at 0.05 T/min and magnetization was performed. After magnetization, the cold head portion of the cooling device to which the bulk magnet structure was fixed was pulled out from the room temperature bore of the superconducting magnet, and the bulk magnet structure was further cooled from 25 K to 20 K. Thereafter, a probe was inserted into the space inside the connecting member 12 of the second container 10b, and the magnetic field distribution was measured.

As a result, it was confirmed that a magnetic field uniformity of 30 ppm was obtained in a space within the range of 5 mm in the axial direction from the center in the layering direction of the bulk magnet structure. Also, no breakage occurred in the bulk magnet structure. From the above fact, it was confirmed that it is possible to magnetize a bulk magnet structure with a strong magnetic field having a high magnetic field uniformity even for a so-called split type bulk magnet structure accessible to the magnetic field space from the lateral direction. In addition, insertion of a probe for measuring a magnetic field distribution was easy and precise measurement could be realized. That is, it was confirmed that access to the magnetic field space from the lateral direction was easy.

Example 2

In Example 2, the bulk magnet structure according to the above third embodiment was fabricated, the bulk magnet structure was magnetized by a superconducting magnet, and the magnetic field distribution on the central axis of the magnetized bulk magnet structure was measured using a probe inserted from the sample insertion port.

First, two columnar bulk bodies having an outer diameter of 70 mm and a thickness of 20 mm and having a structure in which $Eu_2BaCuO_5$ was finely dispersed in a monocrystalline $EuBa_2Cu_3O_y$, and two ring-shaped bulk bodies having an outer diameter of 70 mm, an inner diameter of 35 mm and a thickness of 10 mm and having the same structure were prepared. Then, each bulk body was fitted into an outer circumferential reinforcing ring made of stainless steel (SUS 316 L) having an outer diameter of 80 mm, an inner diameter of 70 mm and a thickness of 20 mm or 10 mm. Incidentally, soldering was used for bonding each bulk body and the outer circumferential reinforcing ring.

Eight columnar bulk bodies having an outer diameter of 70 mm and a thickness of 2 mm and having the same structure were fabricated and nine planar reinforcing plates made of stainless steel having an outer diameter of 70 mm and a thickness of 0.35 mm were alternately arranged with columnar bulk bodies to prepare two columnar stacks. These two columnar stacks were fitted into an outer circumferential reinforcing ring made of stainless steel (SUS 316L) having an outer diameter of 80 mm, an inner diameter of 70 mm and a thickness of 20 mm. At this time, the outer circumferential reinforcing ring, the columnar bulk bodies, and the planar reinforcing bodies were bonded by solder, respectively. Two such columnar stacks were prepared.

In addition, a columnar member made of aluminum alloy having a thickness of 15 mm and an outer diameter of 90 mm was processed to produce the spacer shown in FIG. 6A. In addition, measurements were also made in the case where no spacer was used.

Next, as shown in FIGS. 9A and 9B, a bulk magnet structure was prepared by layering bulk bodies, etc., and the bulk magnet structure was stored in a vacuum heat insulation container. Since the assembling is the same as that of Example 1, the description thereof will be omitted.

The bulk magnet structure was fixed on the cold head, the vacuum heat insulation layer in the vacuum heat insulation container was evacuated and then cooled to 100K. The cold head portion of the cooling device was inserted into the room temperature bore of the superconducting magnet so that the central axis of the bulk magnet structure coincided with the central axis of the superconducting magnet (not shown). Thereafter, the superconducting magnet was energized to excite the superconducting magnet so that the center magnetic field of the superconducting magnet became about 6.5 T. Incidentally, when the spacer was not used, the lower bulk body portions 51*d*-51*f* were cooled in a state of being placed on the cold head 21 of the cooling device 20. The upper bulk body portions 51*a*-51*c* are cooled by using a refrigerant (helium gas or the like) after forming the outer wall in a double structure and providing a vacuum heat insulating layer between the double outer walls.

After completing the excitation of the superconducting magnet, the bulk magnet structure was cooled to 30 K. After the temperature stabilized, the applied magnetic field of the superconducting magnet was demagnetized to zero magnetic field at 0.05 T/min and magnetization was performed. After magnetization, the cold head portion of the cooling device to which the bulk magnet structure was fixed was pulled out from the room temperature bore of the superconducting magnet, and the bulk magnet structure was further cooled from 30 K to 20 K. Thereafter, a probe was inserted into the space inside the connecting member 12 of the second container 10*b*, and the magnetic field distribution was measured.

As a result, it was confirmed that magnetic field uniformity of 15 ppm was obtained in a space within the range of 5 mm in the axial direction from the center in the layering direction of the bulk magnet structure. Also, no breakage occurred in the bulk magnet structure. From the above fact, it has been confirmed that it is possible to stably magnetize the bulk magnet structure with a strong magnetic field having a high magnetic field uniformity. In addition, insertion of a probe for measuring the magnetic field distribution was easy and precise measurement could be realized. That is, it was confirmed that access to the magnetic field space from the lateral direction was easy.

Example 3

In Example 3, a bulk magnet structure according to the above fourth embodiment was fabricated, the bulk magnet structure was magnetized with a superconducting magnet, and the magnetic field distribution on the central axis of the magnetized bulk magnet structure was measured using a probe inserted from the sample insertion port.

First, two columnar bulk bodies having an outer diameter of 70 mm and a thickness of 20 mm and having a structure in which $Eu_2BaCuO_5$ was finely dispersed in a monocrystalline $EuBa_2Cu_3O_y$, were prepared. Then, each bulk body was fitted into an outer circumferential reinforcing ring made of stainless (SUS 316 L) having an outer diameter of 80 mm, an inner diameter of 70 mm and a thickness of 20 mm. Incidentally, soldering was used for bonding each bulk body and the outer circumferential reinforcing ring.

Eight columnar bulk bodies having an outer diameter of 70 mm and a thickness of 2 mm having the same structure were fabricated and nine planar reinforcing plates made of stainless steel having an outer diameter of 70 mm and a thickness of 0.35 mm were alternately arranged with the columnar bulk bodies to prepare a columnar stack. The columnar stack was fitted into the outer circumferential reinforcing ring made of stainless steel (SUS 316 L) having an outer diameter of 80 mm, an inner diameter of 70 mm and a thickness of 20 mm. At this time, the outer circumferential reinforcing ring, the columnar bulk bodies, and the planar reinforcing body were bonded by solder, respectively. Two such columnar stacks were prepared.

Further, six ring-shaped bulk bodies having an outer diameter of 70 mm, an inner diameter of 35 mm and a thickness of 2 mm having the same structure were fabricated, and seven planar reinforcing rings made of stainless steel having an outer diameter of 70 mm, an inner diameter of 34 mm and a thickness of 0.4 mm were alternatingly arranged with the ring-shaped bulk bodies to prepare a ring-shaped stack. The ring-shaped stack was fitted into an outer circumferential reinforcing ring made of stainless steel (SUS 316L) having an outer diameter of 80 mm, an inner diameter of 70 mm and a thickness of 15 mm. At this time, the outer circumferential reinforcing ring, the ring-shaped bulk bodies and the planar reinforcing ring were bonded by solder, respectively. Two such ring-shaped stacks were prepared.

In addition, a columnar member made of aluminum alloy having a thickness of 15 mm and an outer diameter of 90 mm was processed to produce the spacer shown in FIG. 6A. In addition, measurements were also made in the case where no spacer was used.

Next, as shown in FIGS. 10A and 10B, a bulk magnet structure was produced by layering bulk bodies, etc., and the bulk magnet structure was stored in a vacuum heat insulation container. Since the assembling is the same as that of Example 1, the description thereof will be omitted.

The bulk magnet structure was fixed on the cold head, the vacuum heat insulation layer in the vacuum heat insulation container was evacuated and then cooled to 100K. The cold head portion of the cooling device was inserted into the room temperature bore of the superconducting magnet so that the central axis of the bulk magnet structure coincided with the central axis of the superconducting magnet (not shown). Thereafter, the superconducting magnet was energized to excite the superconducting magnet so that the center magnetic field of the superconducting magnet became about 6.5 T. Incidentally, when the spacer was not used, the lower bulk body portions 51*d*-51*f* were cooled in a state of being placed on the cold head 21 of the cooling device 20. The upper bulk body portions 51*a*-51*c* are cooled by using a refrigerant (helium gas or the like) after forming the outer wall in a double structure and providing a vacuum heat insulating layer between the double outer walls . . . .

After completing the excitation of the superconducting magnet, the bulk magnet structure was cooled to 50 K. After the temperature stabilized, the applied magnetic field of the superconducting magnet was demagnetized to zero magnetic field at 0.05 T/min and magnetization was performed. After magnetization, the cold head portion of the cooling device to which the bulk magnet structure was fixed was pulled out from the room temperature bore of the superconducting magnet, and the bulk magnet structure was further cooled from 50 K to 35 K. Thereafter, a probe was inserted into the space inside the connecting member 12 of the second container 10b, and the magnetic field distribution was measured.

As a result, it was confirmed that magnetic field uniformity of 14 ppm was obtained in a space within the range of 5 mm in the axial direction from the center in the layering direction of the bulk magnet structure. Also, no breakage occurred in the bulk magnet structure. From the above fact, it has been confirmed that it is possible to stably magnetize the bulk magnet structure with a high magnetic field having magnetic field uniformity. In addition, insertion of a probe for measuring a magnetic field distribution was easy and precise measurement could be realized. That is, it was confirmed that access to the magnetic field space from the lateral direction was easy.

Example 4

Figure 24A:
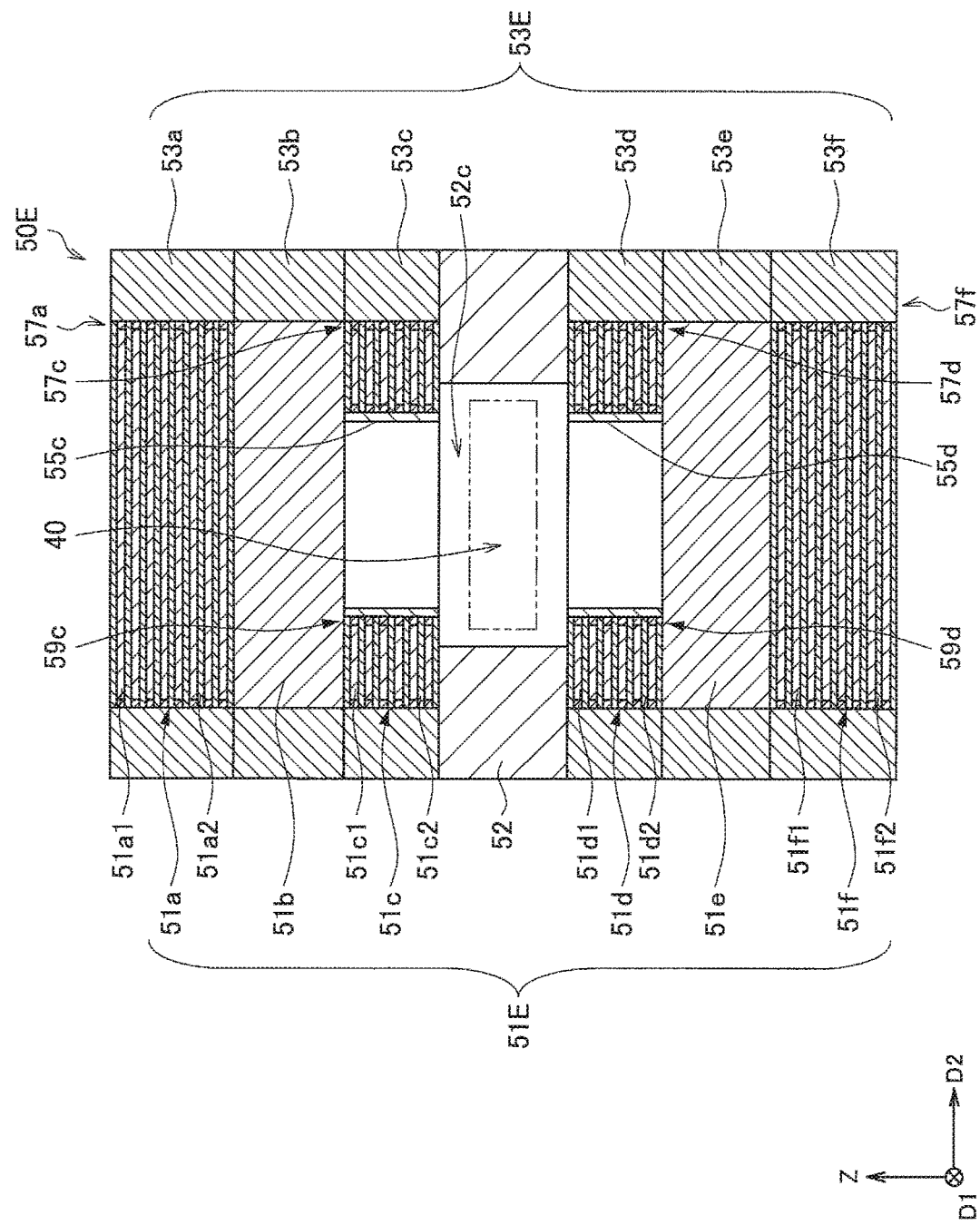
FIG. 24A is a cross-sectional view (viewpoint from a first direction) showing a bulk magnet structure according to Example 4.

In Example 4, the bulk magnet structure 50E shown in FIGS. 24A and 24B was fabricated, the bulk magnet structure was magnetized by the superconducting magnet, and the magnetic field distribution on the central axis of the magnetized bulk magnet structure was measured using a probe inserted from the sample insertion port.

Here, an example of the configuration of the bulk magnet structure 50E according to Example 4 will be described. FIGS. 24A and 24B are cross-sectional views showing an example of the bulk magnet structure 50E according to Example 4. FIG. FIG. 24A is a cross-sectional view as seen from the first direction D1, and FIG. 24 B is a cross-sectional view as seen from the second direction D2.

As shown in FIGS. 24A and 24B, the bulk magnet structure 50E comprises a bulk body portion ME comprising columnar stacks 51a and 51f, columnar bulk bodies Mb and Me and ring-shaped stacks 51c and 51d, a spacer 52, an outer circumferential reinforcing ring portion 53E comprising outer circumferential reinforcing rings 53a-53f respectively fitted to outer circumferential surface of each of the bulk bodies 51a-51f, and inner circumferential reinforcing rings 55c and 55d fitted inside the ring shaped stacks Mc and Md. The bulk magnet structure 50E is formed by layering the respective bulk bodies 51a-51f such that their central axes are aligned to each other. The spacer 52 has a shape shown in FIG. 6A, and it is layered together with the bulk bodies 51a-51f and the outer circumferential reinforcing rings 53a-53f like the bulk magnet structure 50 according to each embodiment.

The ring-shaped stack 51c (51d) is configured by alternately layering a ring-shaped oxide superconducting bulk body 51c1 (51d1) having a small thickness in the axial direction and a planar reinforcing ring 51c2 (51d2). Further, a second outer circumferential reinforcing ring 57c (57d) is disposed between the ring-shaped oxide superconducting bulk body 51c1 (51d1) and the outer circumferential reinforcing ring 53c (53d), and a second inner circumferential reinforcing ring 59 is disposed between the ring-shaped oxide superconducting bulk body 51c1 (51d1) and the inner circumferential reinforcing ring 55c (55d). Such a ring-shaped stack Ma is the same as the configuration according to the sixth configuration example of the above-described ring-shaped stack.

In addition, the columnar stack 51a (51f) is configured by alternately layering a columnar oxide superconducting bulk body 51a1 (51f1) having a small thickness in the axial direction and a plane reinforcing plate 51a2 (51f2). Further, a second outer circumferential reinforcing ring 57a (57f) is disposed between the columnar oxide superconducting bulk body 51a1 (51f1) and the outer circumferential reinforcing ring 53a (53f0). Such a columnar stack 51a (51f) is the same as the columnar stack according to the second configuration example of the above-described columnar stack.

Incidentally, the number of layered columnar bulk bodies and planar reinforcing plates constituting the columnar stack shown in FIGS. 24A and 24B and the number of layered ring-shaped bulk bodies and planar reinforcing rings constituting the ring-shaped stack are examples, and the numbers are not particularly limited.

Returning to the explanation of this example, first, two columnar bulk bodies having an outer diameter of 74 mm and a thickness of 20 mm having a structure in which $Gd_2BaCuO_5$ was finely dispersed in a monocrystalline $GdBa_2Cu_3O_y$, were prepared. Then, each of the ring-shaped bulk bodies was fitted into an outer circumferential reinforcing ring made of stainless steel (SUS 316 L) having an outer diameter of 84 mm, an inner diameter of 74 mm and a thickness of 20 mm. Incidentally, soldering was used for bonding each ring-shaped bulk body and the outer circumferential reinforcing ring.

In addition, eight columnar bulk bodies having an outer diameter of 70 mm and a thickness of 2 mm having the same structure, nine planar reinforcing plates made of stainless steel having an outer diameter of 74 mm and a thickness of 0.35 mm, and eight second outer circumferential rings made of stainless steel having an outer diameter of 74 mm, an inner diameter of 70 mm and a thickness 2 mm were produced and they were arranged in the inside of an outer circumferential reinforcement ring made of stainless steel (SUS 316 L) having an outer diameter of 84 mm, an inner diameter of 74 mm and a thickness of 20 mm so as to form the configuration shown in FIG. 19. At this time, the columnar bulk bodies, the planar reinforcing plates, the outer circumferential reinforcing ring and the second outer circumferential reinforcing rings were bonded by solder, respectively. In this example, two such columnar bulk bodies were fabricated.

Further, six ring-shaped bulk bodies having an outer diameter of 70 mm, an inner diameter of 35 mm and a thickness of 2 mm having the same structure, seven planar reinforcing rings made of stainless steel having an outer diameter of 74 mm, an inner diameter of 33 mm and a thickness of 0.4 mm, six second outer circumferential reinforcing rings made of stainless steel having an outer diameter of 74 mm, an inner diameter of 70 mm and a thickness of 2 mm, and six second inner circumferential reinforcing rings made of stainless steel having an outer diameter of 35 mm, an inner diameter of 33 mm and a thickness of 2 mm were produced. These were fitted between an outer circumferential reinforcing ring made of stainless steel (SUS 316 L) having an outer diameter of 84 mm, an inner diameter of 74 mm and a thickness of 16 mm, and an inner circumferential reinforcing ring made of stainless steel having an outer diameter of 33 mm, an inner diameter of 31 mm and a thickness of 16 mm so as to form the configuration shown in FIG. 19. At this time, the ring-shaped bulk bodies, the planar reinforcing rings, the outer circumferential reinforcing ring, the inner circumferential reinforcing ring, the second outer circumferential reinforcing rings and the second inner circumferential reinforcing rings were bonded by solder, respectively. In this example, two such ring-shaped bulk bodies were fabricated.

In addition, a columnar member made of aluminum alloy having a thickness of 15 mm and an outer diameter of 90 mm was processed to produce the spacer shown in FIG. 6A. In addition, measurements were also made in the case where no spacer was used.

Next, as shown in FIGS. 24A and 24B, a bulk magnet structure was produced by layering bulk bodies, etc., and the bulk magnet structure was stored in a vacuum heat insulation container. Since the assembling is the same as that of Example 1, the description thereof will be omitted.

The bulk magnet structure was fixed on the cold head, the vacuum heat insulation layer in the vacuum heat insulation container was evacuated and then cooled to 100K. The cold head portion of the cooling device was inserted into the room temperature bore of the superconducting magnet so that the central axis of the bulk magnet structure coincided with the central axis of the superconducting magnet (not shown). Thereafter, the superconducting magnet was energized to excite the superconductive magnet so that the central magnetic field of the superconducting magnet became about 6.5 T. When the spacer was not used, the lower bulk body portions 51*d*-51*f* were cooled in a state of being placed on the cold head 21 of the cooling device 20. The upper bulk body portions 51*a*-51*c* were cooled by using a refrigerant (helium gas or the like) after forming the outer wall in a double structure and providing a vacuum heat insulating layer between the double outer walls.

After completing the excitation of the superconducting magnet, the bulk magnet structure was cooled to 50 K. After the temperature stabilized, the applied magnetic field of the superconducting magnet was demagnetized to zero magnetic field at 0.05 T/min and magnetization was performed. After magnetization, the cold head portion of the cooling device to which the bulk magnet structure was fixed was pulled out from the room temperature bore of the superconducting magnet, and the bulk magnet structure was further cooled from 50 K to 35 K. Thereafter, a probe was inserted into the space inside the connecting member 12 of the second container 10*b*, and the magnetic field distribution was measured.

As a result, it was confirmed that magnetic field uniformity of 14 ppm was obtained in a space within the range of 5 mm in the axial direction from the center in the layering direction of the bulk magnet structure. Also, no breakage occurred in the bulk magnet structure. From the above fact, it has been confirmed that it is possible to stably magnetize the bulk magnet structure with a stronger magnetic field having a high magnetic field uniformity. In addition, insertion of a probe for measuring a magnetic field distribution was easy and precise measurement could be realized. That is, it was confirmed that access to the magnetic field space from the lateral direction was easy.

Comparative Example

In the case of using a coil formed by simply winding a superconducting wire instead of a bulk magnet, the dimensions (inner diameter, outer diameter, axial length) of the structure of this coil magnet were magnetized under the same conditions as in Example 1. The magnetic field distribution in the case was calculated. In this case, superconducting junctions are formed completely at both ends of the wire material of each coil magnet, and in the case of magnetizing under the same conditions, a permanent current flows in the coil magnet, and due to this permanent current, the coil magnet would be in a situation where it is magnetized. As a result of the calculation, the magnetic field non-uniformity was 10000 ppm or more in a space within the range of 5 mm in the axial direction from the center in the layering direction of the magnet structure, which was a very nonuniform distribution.

Figure 25:
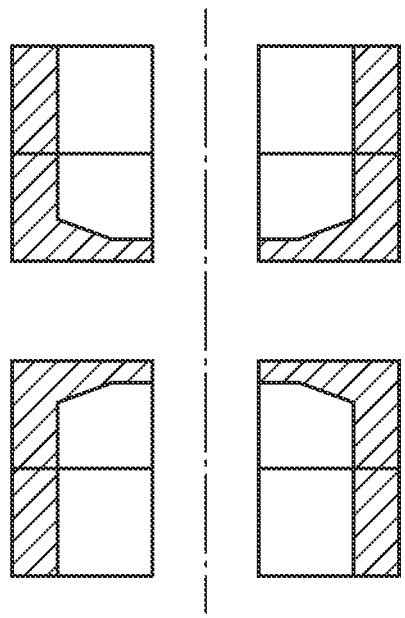
FIG. 25 is a schematic view showing a difference between superconducting current densities in a comparative example and an example of the present invention.
Figure 25:
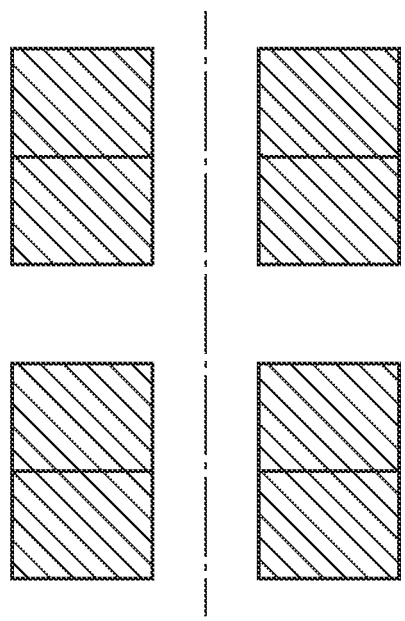

The fundamental significant difference between such a coil in which the wire material is coiled and the bulk magnet of the present invention is that in a coil magnet wherein a wire material is wound, the superconducting current density flowing in the circumferential direction in the coil magnet is equal at any cross-section of the magnet, whereas in the bulk magnet, as described in detail with reference to FIGS. 4A to 4C, the superconducting current density flowing in the circumferential direction in the bulk magnet varies in the cross-section of the magnet. Even in the fully magnetized state, the current density is not constant because the current density depends on a magnetic field. FIG. 25 schematically shows the difference between the superconducting current densities in Comparative Example and the example of the present invention. FIG. 25 (*a*) shows a mode in which the bulk magnets of the example of the present invention are spaced apart and magnetized. The superconducting current flows in the hatched region, and no superconducting current flows in the region not hatched. FIG. 25 (*b*) shows a case where the coil magnet of Comparative Example is magnetized. The superconducting current flows throughout the coil (cross-section).

As described above, the bulk magnet has a flexibility of the current distribution, and as compared to the coil magnet, it will have an enhanced function of maintaining the captured magnetic field distribution before the demagnetization.

Although the preferred embodiments of the present invention have been described in detail with reference to the accompanying drawings, the present invention is not limited to such examples. Those having ordinary knowledge in the technical field to which the present invention belongs can clearly conceive various modifications or variations within the scope of the technical idea described in the claims. It is understood that these are naturally also within the technical scope of the present invention.

REFERENCE SIGNS LIST

1 Bulk magnet system for NMR
10 Vacuum insulation container
10*a* First container
10 *b* Second container
10*c* Third container
11 O ring
12 Connecting member
20 Cooling device
21 Cold head
23 Heater
30 Temperature controller
50 Bulk magnet structure
51 Bulk body (stack)
51*a* Ring-shaped stack
51*a*1 Ring-shaped oxide superconducting bulk body
51*a*2 Planar reinforcing ring
Mg Columnar stack
51*g*1 Columnar oxide superconducting bulk body
51*g*2 Planar reinforcing plate
52 Spacer
52*a* Spacer member
52*b* Spacer member
53 Outer circumferential reinforcing ring
55 Inner circumferential reinforcing ring
57 Second outer circumferential reinforcing ring
59 Second inner circumferential reinforcing ring
100 Bulk Magnet 110 Ring-shaped bulk body
120 Planar reinforcing ring
130 Outer Circumferential reinforcing ring
200 Bulk Magnet
210 Ring-shaped bulk body
220 Planar reinforcing ring
230 Outer circumferential reinforcing ring
300 Bulk Magnet
310 Ring-shaped bulk body
320 Planar reinforcing ring
330 Outer circumferential reinforcing ring
400 Bulk Magnet
410 Ring-shaped bulk body
420 Planar reinforcing ring
430 Outer circumferential reinforcing ring
500 Bulk Magnet
510 Ring-shaped bulk body
520 Planar reinforcing ring
530 Outer circumferential reinforcing ring
540 Inner circumferential reinforcing ring
600 Bulk Magnet
610 Ring-shaped bulk body
620 Planar reinforcing ring
650 Ring-shaped bulk body
700 Bulk Magnet
710 Ring-shaped bulk body
800 Bulk Magnet
810 Columnar bulk body
820 Planar reinforcing plate
830 Outer circumferential reinforcing ring
900 Bulk Magnet
910 Columnar bulk body
920 Planar reinforcing plate
6300 Outer circumferential reinforcing ring
6310 Second outer circumferential reinforcing ring
6400 Inner circumferential reinforcing ring
6410 Second inner circumferential reinforcing ring
9300 Outer circumferential reinforcing ring
9310 Second outer circumferential reinforcing ring

The invention claimed is:

1. A bulk magnet structure comprising
a plurality of oxide superconducting bulk bodies arranged such that their central axes are on the same line, and
at least one outer circumferential reinforcing ring fitted to cover the outer circumferential surfaces of the plurality of oxide superconducting bulk bodies,
wherein the plurality of oxide superconducting bulk bodies comprise at least a columnar oxide superconducting bulk body or a ring-shaped oxide superconducting body,
wherein at least one pair of adjacent oxide superconducting bulk bodies are spaced apart from each other in the central axis direction and the bulk magnet structure has a space inside thereof through which the central axis passes, and
wherein the space penetrates from a portion of a lateral circumferential portion of the bulk magnet structure to another portion of the lateral circumferential portion, in a direction perpendicular to the central axis.

2. A bulk magnet structure comprising
a plurality of oxide superconducting bulk bodies, and
at least one outer circumferential reinforcing ring fitted to cover the outer circumferential surfaces of the plurality of layered oxide superconductive bulk bodies,
a spacer layered together with the oxide superconducting bulk bodies,
wherein the plurality of oxide superconducting bulk bodies comprise at least a columnar oxide superconducting bulk body or a ring-shaped oxide superconducting bulk body,
wherein the spacer has a space formed so as to penetrate from a portion of the lateral circumferential portion to another portion of the lateral circumferential portion, and the spacer is layered so that at least the central axis of the bulk magnet structure passes through the space, and
wherein the space penetrates from a portion of the lateral circumferential portion of the bulk magnet structure to another portion of the lateral circumferential portion, in a direction perpendicular to the layering direction of the layered oxide superconducting bulk bodies.

3. A bulk magnet structure comprising
a plurality of oxide superconducting bulk bodies,
at least one outer circumferential reinforcing ring fitted to cover the outer circumferential surfaces of the plurality of layered oxide superconducting bulk bodies, and
a space,
wherein the plurality of oxide superconducting bulk bodies comprise a ring-shaped oxide superconducting bulk body, and
wherein the space is capable of forming a magnetic field space by the bulk magnet structure, placing a sample and/or device and communicating with the outside of the bulk magnet structure, in two directions of a direction perpendicular to the layering direction and the layering direction.

4. The bulk magnet structure according to claim 1, wherein the plurality of oxide superconducting bulk bodies comprise a ring-shaped oxide superconducting body, and the space is capable of communicating with the outside of the bulk magnet structure, in a direction perpendicular to the central axis.

5. The bulk magnet structure according to claim 1, wherein the space may be disposed in a central portion in the layering direction of the bulk magnet structure.

6. The bulk magnet structure according to claim 2, wherein the spacer is formed by a non-superconducting bulk body, and the non-superconducting bulk body has a thermal conductivity of 20 W/(m K) or more.

7. The bulk magnet structure according to claim 1, wherein at least one of the oxide superconducting bulk bodies adjacent to the space in the layering direction of the bulk magnet structure is the ring-shaped oxide superconducting bulk body.

8. The bulk magnet structure according to claim 1, wherein at least one of the columnar oxide superconducting bulk bodies is a stack in which a columnar oxide superconducting bulk body and a planar reinforcing plate are alternately arranged.

9. The bulk magnet structure according to claim 1, wherein at least one of the ring-shaped oxide superconducting bulk bodies is a stack in which a ring-shaped oxide superconducting bulk body and a planar ring are alternately arranged.

10. The bulk magnet structure according to claim 9, wherein the ring-shaped oxide superconducting bulk body has an inner circumferential reinforcing ring inside the body.

11. The bulk magnet structure according to claim 10, wherein a second inner circumferential reinforcing ring is provided between the ring-shaped oxide superconducting bulk body and the inner circumferential reinforcing ring.

12. The bulk magnet structure according to claim 1, wherein a second outer circumferential reinforcing ring is provided between the oxide superconducting bulk body and the outer circumferential reinforcing ring.

13. The bulk magnet structure according to claim 1, wherein the oxide superconducting bulk body contains an oxide having a structure in which $RE_2BaCuO_5$ is dispersed in a monocrystalline $REBa_2Cu_3 O_y$, wherein RE is one or two or more elements selected from rare earth elements, and $6.8 \leq y \leq 7.1$.

14. A magnet system for NMR comprising
a bulk magnet structure according to claim 1 housed in a vacuum container,
a cooling device for cooling the bulk magnet structure, and
a temperature controller for adjusting a temperature of the bulk magnet structure.

15. The magnet system for NMR according to claim 14, wherein the oxide superconducting bulk body constituting the bulk magnet structure is in a magnetized state.

16. The bulk magnet structure according to claim 2, wherein the plurality of oxide superconducting bulk bodies comprise a ring-shaped oxide superconducting body, and the space is capable of communicating with the outside of the bulk magnet structure, in the layering direction.

17. The bulk magnet structure according to claim 3, wherein the space penetrates from a portion of the lateral circumferential portion of the bulk magnet structure to another portion of the lateral circumferential portion.

18. The bulk magnet structure according to claim 2, wherein the space may be disposed in a central portion in the layering direction of the bulk magnet structure.

19. The bulk magnet structure according to claim 3, wherein the space may be disposed in a central portion in the layering direction of the bulk magnet structure.

20. The bulk magnet structure according to claim 4, wherein the space may be disposed in a central portion in the layering direction of the bulk magnet structure.

* * * * *